US010253377B2

(12) United States Patent
Akins et al.

(10) Patent No.: US 10,253,377 B2
(45) Date of Patent: Apr. 9, 2019

(54) SYSTEMS AND METHODS TO ASSESS MICROBIOMES AND TREATMENTS THEREOF

(71) Applicants: Robert A. Akins, Novi, MI (US); Jack D. Sobel, West Bloomfield, MI (US)

(72) Inventors: Robert A. Akins, Novi, MI (US); Jack D. Sobel, West Bloomfield, MI (US)

(73) Assignee: Wayne State University, Detroit, MI (US)

(*) Notice: Subject to any disclaimer, the term of this patent is extended or adjusted under 35 U.S.C. 154(b) by 494 days.

(21) Appl. No.: 14/782,449

(22) PCT Filed: Apr. 4, 2014

(86) PCT No.: PCT/US2014/033055
§ 371 (c)(1),
(2) Date: Jan. 5, 2016

(87) PCT Pub. No.: WO2014/165810
PCT Pub. Date: Oct. 9, 2014

(65) Prior Publication Data
US 2016/0040216 A1    Feb. 11, 2016

Related U.S. Application Data

(60) Provisional application No. 61/809,071, filed on Apr. 5, 2013, provisional application No. 61/840,300, filed on Jun. 27, 2013.

(51) Int. Cl.
*C12P 19/34* (2006.01)
*C12Q 1/689* (2018.01)
*C12Q 1/6883* (2018.01)
*G06F 19/00* (2018.01)

(52) U.S. Cl.
CPC .......... *C12Q 1/689* (2013.01); *C12Q 1/6883* (2013.01); *G06F 19/00* (2013.01); *G06F 19/3456* (2013.01); *C12Q 2600/106* (2013.01); *C12Q 2600/158* (2013.01); *Y02A 90/26* (2018.01)

(58) Field of Classification Search
CPC .................. C12Q 1/6883; C12Q 1/689; C12Q 2600/106; C12Q 2600/158; G06F 19/3456; Y02A 90/26
USPC ....................................................... 435/91.2
See application file for complete search history.

(56) References Cited

U.S. PATENT DOCUMENTS

| 5,849,497 A | 12/1998 | Steinman |
| 2004/0072242 A1* | 4/2004 | Hunter et al. ......... C12Q 1/689 435/7.1 |
| 2004/0111221 A1* | 6/2004 | Beattie .................. G06F 19/20 702/20 |
| 2006/0172330 A1 | 8/2006 | Osborn et al. |
| 2007/0178495 A1 | 8/2007 | Fredricks et al. |
| 2011/0151462 A1 | 6/2011 | Tynan et al. |
| 2012/0264126 A1 | 10/2012 | Johnson et al. |

FOREIGN PATENT DOCUMENTS

WO    WO2012151560    11/2012

OTHER PUBLICATIONS

European Search Report dated Oct. 26, 2016 for European Patent Application No. 14778044.9.
Lambert, et al., "Novel PCR-Based Methods Enhance Characterization of Vaginal Microbiota in a Bacterial Vaginosis Patient before and after Treatment", AEM, vol. 79, No. 13, 2013, pp. 4181-4185.
Wintzingerode, et al, "Peptide Nucleic Acid-Mediated PCR Clamping as a Useful Supplement in the Determination of Microbial Diversity", AEM, vol. 66, No. 2, 2000, pp. 549-557.
Cheng, et al., "Rapid Detection and Identification of Clinically Important Bacteria by High-Resolution Melting Analysis after Broad-Range Ribosomal RNA Real-Time PCR", Clinical Chemistry, vol. 52, No. 11, 2006, pp. 1997-2004.
Gajer, et al., "Temporal Dynamics of the Human Vaginal Microbiota", Science Translational Medicine, vol. 4, No. 132, 2012, pp. 1-13.
GenBank_AY823503.1.
GenBank_JQ962733.2.
Lambert, et al., "Longitudinal Analysis of Vaginal Microbiome Dynamics in Women with Recurrent Bacterial Vaginosis: Recognition of the Converion Process", PLOS One, vol. 8, No. 12, 2013, pp. 1-10.
Search Report & Written Opinion dated Nov. 17, 2014 in International Application No. PCT/US2014/033055.

* cited by examiner

*Primary Examiner* — Cynthia B Wilder
(74) *Attorney, Agent, or Firm* — Lee & Hayes, P.C.; C. Rachal Winger; Tanya Harding

(57) ABSTRACT

Systems and methods to assess the health of various microbiomes and to identity species therein are disclosed. Described assessments and identifications can inform treatment decisions if a microbiome is determined to have a less than optimal balance of bacterial species within it; the presence of one or more negative species; and/or the absence of one or more positive species.

4 Claims, 29 Drawing Sheets

Specification includes a Sequence Listing.

| 1 | Gardnerella vaginalis |
|---|---|
| 2 | Atopobium vaginae |
| 3 | Eggerthella sp, Uncultured |
| 4 | Propionibacterium acnes |
| 5 | Corynebacterium sp, Uncultured |
| 6 | Corynebacterium thomssenii |
| 7 | Corynebacterium amycolatum |
| 8 | Corynebacterium coyleae |
| 9 | Corynebacterium pyruviciproducens |
| 10 | ~Corynebacterium ureicelerivorans |
| 11 | Brevibacterium sp |
| 12 | Actinomycetales bacterium, Uncultured |
| 13 | Lactobacillus iners |
| 14 | Lactobacillus jensenii |
| 15 | Lactobacillus gasseri |
| 16 | ~Lactobacillus sp |
| 17 | Aerococcus sp, Uncultured |
| 18 | ~Roseburia |
| 19 | ~Ruminococcus |
| 20 | Anaerococcus prevotii |
| 21 | Peptoniphilus sp |
| 22 | Dialister sp, Uncultured |
| 23 | Leptotrichia amnionii |
| 24 | Bacteroides sp, Uncultured |
| 25 | Prevotella bivia |
| 26 | ~Sphingomonas aerolata |
| 27 | Escherichia coli |
| 28 | Aggregatibacter sp |
| 29 | Pseudomonas fluorescens |
| 30 | Pseudomonas pseudoalcaligenes |
| 31 | Methylobacterium aminovorans |
| 32 | Janthinobacterium lividum |
| 34 | Arcobacter cryaerophilus |

FIG. 3 (cont'd)

1. Lactobacillaceae
2. Actinobacteridae
3. Bacteroidaceae/uc Prevotellaceae
4. Fusobacteria
5. uc Clostridiales (BVAB2&3 subset)
6. Mycoplasmatales
7. Streptococcus
8. Coriobacteridae
9. Lachnospiraceae group
10. Mobiluncus
11. Cross-family Clostridia
12. Clostridiales Incertae Sedis XII
13. Peptostreptococcaceae**
14. Megasphaera group
15. Staphylococcus
16. Betaproteobacteria
17. Enterobacteriales group

FIG. 10 (cont'd)

SYSTEMS AND METHODS TO ASSESS MICROBIOMES AND TREATMENTS THEREOF

CROSS-REFERENCE TO RELATED APPLICATIONS

This application is a U.S. national stage entry of PCT/US2014/033055 filed Apr. 4, 2014 which claims priority to U.S. Provisional Patent Application No. 61/809,071, filed on Apr. 5, 2013, and U.S. Provisional Patent Application No. 61/840,300, filed on Jun. 27, 2013, the entire contents of each of which is incorporated herein by reference.

FIELD OF THE DISCLOSURE

The disclosure relates to systems and methods to assess the health of microbiomes. The systems and methods can be used to rapidly assess microbiome health; determine individualized therapies for microbiome infections; predict failure of infection therapies, and/or monitor progress of infection therapies.

BACKGROUND OF THE DISCLOSURE

There are a number of distinct microbiomes associated with living organisms. Generally, healthy microbiomes have one or more dominant bacterial species. Conversely, a number of diseases or disorders are associated with perturbed bacterial populations within microbiomes when, for example, the prevalence of one or more non-dominant species increases, lowering the relative content of the dominant species associated with good microbial health. Rapid and economical detection, identification, and/or quantification of species within a microbiome are important aspects of disease diagnosis and prognosis.

SUMMARY OF THE DISCLOSURE

The disclosure relates to systems and methods to assess the health of microbiomes. The systems and methods can be used to rapidly assess microbiome health; determine individualized therapies for microbiome infections; predict success or failure of infection therapies, and/or monitor progress of infection therapies. The systems and methods can determine the relative content of a dominant bacterial species in a microbiome and can identify and/or categorize non-dominant species populations.

LISTING OF TABLES

Figure 1:
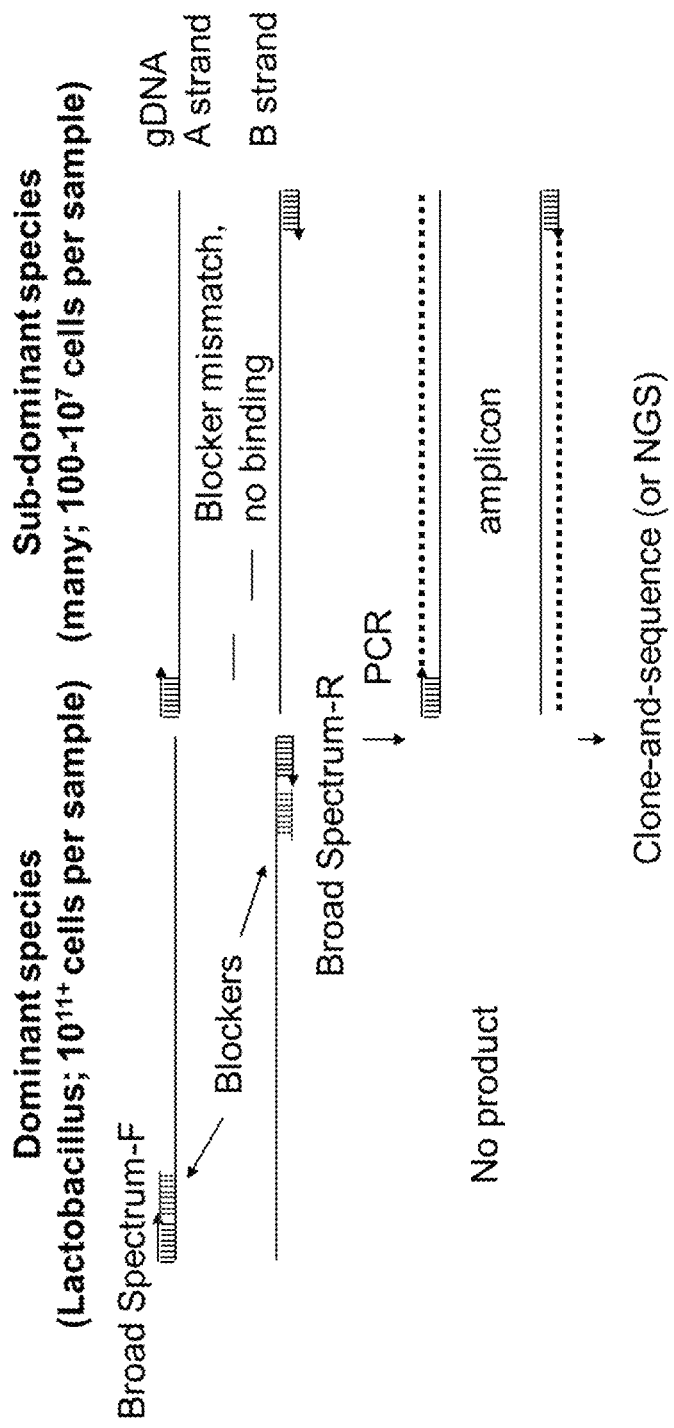
FIG. 1. Blocking amplification of a dominant species in a complex bacterial sample using target-specific oligomers.

Table 1. Percentage of RDP database entries with perfect complementarity to broad-spectrum primers used in vaginal studies.

Table 2. Primers useful for amplifying LB (LB) and non-LB species in vaginal samples.

Table 3. (A) Acute BV PBN-qPCR; (B) Post-tinidazole PC-qPCR; (C) Acute BV 16S-C&S; (D) Post tinidazole 16S-C&S; (E) In silicose performance.

Table 4. Richness and diversity parameters.

DETAILED DESCRIPTION

There are a number of distinct microbiomes associated with living organisms. Microbiomes include a large number of bacteria with a variety of bacterial species present. Rapid and economical detection, identification, and/or quantification of species within a microbiome are important aspects of disease diagnosis and prognosis.

Generally, healthy microbiomes have one or more dominant bacterial species. As used herein, the term "dominant species" refers to a bacterial species that is present in a microbiome at a higher number than other bacterial species. In certain embodiments, a single dominant genus or species comprises greater than 80%, greater than 85%, greater than 90%, greater than 95%, greater than 96%, greater than 97%, greater than 98% or greater than 99% of the total bacteria in the microbiome. For the purposes of this disclosure a dominant species can refer to a single species, or all species in a genus.

A number of diseases or disorders associated with perturbed bacterial microbiomes occur when the prevalence of one or more non-dominant species increases, lowering the relative content of the dominant species associated with good microbial health. As used herein, the term "non-dominant species" refers to all bacterial species and genera that are not classified as "dominant" as defined herein.

The current disclosure provides systems and methods for assessing the relative abundance or ratio of dominant versus non-dominant bacterial species within a bacterial microbiome sample. The systems and methods can also assess the relative abundance or ratio of a non-dominant bacterial species compared to another non-dominant bacterial species within a microbiome sample. The systems and methods also allow the identification and/or characterization of non-dominant species using melt curve analysis. The identification, characterization, relative abundance, or ratio of non-dominant species can be used to inform treatment decisions including whether to treat, the type of treatment, changing treatment and/or the length of treatment.

Based on the foregoing, the systems and methods disclosed herein can be used for assessing the health of a microbiome. As used herein, the term "microbiome" refers to the totality of bacterial microbes in a particular environment. The systems and methods allow for rapidly assessing microbiome health; determining an individualized therapy for bacterial infections; predicting success or failure of antibacterial therapy of infections; and/or monitoring progress of antibacterial therapy of infections. One embodiment includes determining the relative content of a dominant species in a biological sample and, in further embodiments, for categorizing non-dominant species populations in samples, including in unhealthy samples.

Bacterial vaginosis (BV) is the most common vaginal infection worldwide. BV refers to a condition in women where the normal balance of bacteria in the vagina is disrupted and replaced by an overgrowth of certain bacteria. BV is sometimes accompanied by discharge, odor, pain, itching, or burning. BV is the most common cause of vaginal symptoms among women, but it is not clear what role sexual activity plays in the development of BV. The prevalence in the United States is estimated to be 21.2 million (29.2%) among women ages 14-49. Most women found to have BV (84%) reported no symptoms. Women who have not had vaginal, oral, or anal sex can still be affected by BV (18.8%), as can pregnant women (25%), and women who have never been pregnant (31.7%). Prevalence of BV increases based on lifetime number of sexual partners. Non-white women have higher rates of BV (African-American 51%, Mexican Americans 32%) than white women (23%).

In many cases, BV causes no complications. There are some serious risks from BV, however, including increasing a woman's susceptibility to HIV infection if she is exposed to the HIV virus, increasing the chances that an HIV-infected woman can pass HIV to her sexual partner, increasing the risk of an infection following surgical procedures such as a hysterectomy or an abortion, increasing the risk for some complications of pregnancy, such as preterm delivery, and increasing a woman's susceptibility to other STDs, such as herpes simplex virus (HSV), chlamydia, and gonorrhea.

BV exhibits perplexingly high recurrence rates. Despite decades of analysis using microbiological and molecular tools, BV has no defined etiological basis. These difficulties result in part from the complex microbiota of the vagina, composed of dozens, perhaps hundreds of bacterial species, with titers ranging from billions to less than 100 cells, many of which are fastidious, unculturable, or difficult to identify.

Current technologies to diagnose bacterial load in the vagina include clinical criteria (Amsel score), microbiological assays (gram stain, Nugent score), and a molecular probe assay (AFFIRM™ VPIII Microbial Identification Test, Becton, Dickinson and Company) that detects *Candida* species, *Gardnerella vaginalis* and *Trichomonas vaginalis*. Additionally there are molecular assays based on PCR or quantitative PCR (qPCR) detection of individual BV-associated microbes.

Amsel and Nugent scoring are often inaccurate. Amsel scoring also does not recognize asymptomatic or presymptomatic BV and Nugent scores have an inherent drawback due to lack of specificity of morphotype species due to guessing. The AFFIRM™ assay relies on the oversimplified, and often inaccurate, assumption that high levels of *Gardnerella* are sufficient to diagnose BV and also exhibits many false positives and negatives. Other molecular assays rely on empirically optimized thresholds of specific BV-associated anaerobes, which vary significantly between individuals and upon the day of testing.

Two PCR-based strategies have been traditionally employed to characterize the vaginal microbiota. The 16S clone and sequence approach, 16S-C&S (culture and sensitivity) had previously been considered a breakthrough technology in characterizing microbiota in the environment and in human sites, including gut, stomach, oral, skin, vulva, and vagina. It uses broad spectrum primers to generate a complex amplicon of the 16S rDNA gene of bacterial species, which is then cloned into *E. coli* and 100 to 1000 clones are sequenced. The species are determined by comparison to large 16S rDNA databases. NGS extends this to 2500 to one million sequence reads per sample and has now been applied in at least 4 large scale studies of bacterial populations in the vaginal mucosa of healthy, asymptomatic, and symptomatic BV patients.

One limitation of this strategy is that even the best broad-spectrum primers are not entirely universal, but have mismatches for whole phyla in silico (i.e., *Chlamydia*, Table 1). They often fail to detect species reported by culture or species-specific PCR due to the low relative titer of the missed species, the under-amplification of the missed target, and sometimes as a result of primer mismatch. Another limitation is the ability to detect only the most dominant species and not those present at less than $\frac{1}{1000}$ the titer of dominant species. Without modification, more than 99.5% of the clones from vaginal samples from healthy women belong to one or a group of species, mostly lactobacilli. NGS allows sequencing of up to one million molecules per run, but the cost of each run forces researchers to pool up to 200 samples per run by using a primer barcoding system, typically generating ~2500 usable reads per sample. This makes it likely that many subdominant but potentially significant vaginal species, still present at $10^4$-$10^6$ cells per sample, will not be detected or accurately quantified. Another limitation is that rare species in these populations may be differentially under-amplified.

It is therefore necessary to develop additional tools in the analysis of complex bacterial populations. One solution disclosed herein is to block the amplification of dominant species through peptide nucleic acid (PNA) clamping. Modified oligomers added to the PCR reaction anneal to sequences specific to the dominant species, thereby blocking amplification. Thus, the subdominant species are exponentially amplified and readily identified from small numbers of clones, as illustrated (FIG. 1). Healthy and post-treatment (PT) BV samples often are 99%+LB spp. LB-blockers are designed to hybridize specifically to sequences in the LB genus and partially overlap with the broad-spectrum primers. They are composed of oligomers (or PNA) that cannot be degraded or extended by Taq DNA polymerase. As the dominant species cannot be amplified, the product of a blocked PCR reaction consists of all the subdominant species in their relative proportions.

The disclosed technology uses custom primers and blocking primers for amplifying and selectively amplifying bacterial DNA within a microbiome. This approach will provide a yield for virtually all bacteria present in the microbiome. In vaginal microbiome environments, some wells contain blocking primers which specifically block the amplification of the LB phyla/genus and allow the growth of non-LB organisms. The curve with the samples that contain the blocking primers can then be subtracted from the total curve without the blocking primers to yield the total number of non-LB bacteria in the vaginal microbiome. In a healthy vaginal microbiome, non-LB bacteria should be less than 1% of the total bacteria. In BV, the total amount of non-LB will be greater than 1%. Thus the disclosed systems and methods provide a semi-quantitative measure for BV. The disclosed systems and methods have increased sensitivity over current methods used and can be used as an early indicator of the disease (prognostic). Using the disclosed systems and methods, shifts in the PCR curves have been noticed prior to a positive diagnosis by Nugent score and before symptoms appear. Diagnosis of BV prior to onset of clinical symptoms allows initiation of treatment when BV is most responsive.

The disclosed systems and methods use a DNA detection system such as PCR or probe or bead technologies. In one embodiment, the DNA detection system is a real-time PCR technology using a light cycler, primers and blockers in a 96 well format. The threshold cycle (CT or $C_t$) curve plateaus around 35 cycles for all curves. There is enough bacterial DNA in the samples that contaminant bacterial DNA from ambient air in the laboratory is not an issue as it is in some assays. The primers and blocking primers can be custom made (in one embodiment, custom versions of 16sRNA primers).

Using modified blocking oligomers improves the detection of diverse but less dominant species within a microbiome, and this improvement is further enhanced by results from primer blocking (PB)-quantitative PCR (qPCR). These tools allow feasible, in-depth characterization of large numbers of samples, documenting sequential changes in individual patients to help establish cause-and-effect relationships. They also allow clustering of samples into microbiological classes that predict risk for infection.

The strategy of blocking amplification of dominant species during broad spectrum PCR and qPCR using phylogenetic branch specific primers are effective tools for in-depth characterization of complex microbiota in a cost effective manner. In the vaginal microbiome, the LB-blocking strategy is useful for assessing LB-dominant vaginal samples of healthy women or of BV patients after treatment. In the latter group, determination of subdominant species (or low level of dominant species) is useful in predicting recurrence. The PB-qPCR strategy is more broadly useful for characterizing any vaginal sample.

Control reactions indicate that LB-blocking is specific to LB, and that its use allowed the detection of 21 less dominant species among 136 LB-blocked sequences, present at 6 orders of magnitude below LB. This sample detection level would have required over one million reads if not blocked. PB-primers did not amplify detectable levels of non-targeted species directly from purified lavage DNA. PB-qPCR detected 12 of 14 targets estimated at titers below $1 \times 10^6$ cells/sample by PB-qPCR (FIG. 5) which would have not been detected in 2500 read sets by NGS. This is consistent by comparison with recent NGS studies of vaginal populations. In one, 90 samples from Amsel- and Nugent-based healthy samples were analyzed, reading an average of 2235 sequences per sample, and detected an average of only 3 non-LB sequences per sample. This ranged from 0 to 22, with 18% of samples generating only LB sequences. Another NGS study, averaging 2236 reads per sample, found among 173 asymptomatic patients with Nugent 0-3 and pH <4.5, that an average of only 12 reads per sample were non-LB species.

Even with LB-blocking, many sequences detected in the studies described herein were singlets, indicating that the species description is far from saturated and that their quantification is approximate. Nevertheless, based on the number of reads and the estimated overall bacterial titer, singlet species represent a titer of $10^4$ cells per sample. Detecting other species that might be present at $10^4$ cells per sample in unblocked samples would require ~170 million sequences, more than can be achieved by non-multiplexed NGS, at significant cost per sample. Coupling blockers with NGS generates the most complete inventory of complex microbial populations when samples are dominated to the extent commonly seen in healthy or PT vaginal samples.

Both PB-qPCR and 16S-C&S approaches resulted in similar profiles in a patient before and after treatment, differing only in their depiction of low titer species whose quantification was skewed by low read numbers. A set of 20 PB-qPCR primers detected 12 target groups (Coriobacteria, Mobiluncus, Fusobacteria, Lachnospiraceae, BVAB2, cross-family Clostridia, Clostridiales Incertae Sedis XI, Peptostreptococcaceae, Veillonellaceae, *Streptococcus, Staphylococcus*, and Mycoplasmatales) that were not seen in the 16S-C&S data in one or both samples. Conversely, 16S-C&S detected targets in α- and ε-Proteobacteria, which were not targeted by one inventory of PB primers. Thus, the two approaches are complementary, one providing enhanced sensitivity and the other more inclusiveness. Quantification of blocked samples can be improved by tracking the titer of a known species spiked into the sample at low titer before processing. As the assay and the literature evolve, more and more bacterial groups will be recognized and targeted.

Eighteen uncloned PB-amplicons from the two samples could be directly sequenced to determine the dominant species in the target group: Lactobacillaceae, Actinobacteridae, Coriobacteridae, Mobiluncus, *Bacteroides*, Fusobacterium, Lachnospiracea, uc Clostridiales (BVAB2&3 subset), Clostridiales Incertae Sedis XI, Clostridiales Incertae Sedis XII, *Streptococcus*, and Mycoplasmatales. The remaining amplicons consisted of mixed templates from co-dominant species, but could be resolved by sequencing of <20 clones. Thus, the approach improves inclusiveness relative to species-specific qPCR yet still allows rapid access to species identification. A limitation of PB-qPCR is that the amplicon or clones from it must be sequenced, but this is also true of amplicons generated with species-specific primers. Related species may be amplified with a mismatched species-specific primer, which is likely to result in an underestimation of its titer.

There were many shifts in dominant species in the targeted subpopulations after tinidazole treatment (Tables 3A-3D). The Lachnospiracae population shifted from novel *Shuttleworthia* species, to novel species related to *Ruminococcus*. This may be a shift away from butyrate-producing species which may be involved generating symptoms of BV. Similar novel subtypes of Lachnospiracae are seen among the large collection of pyrosequences in other BV studies. Among Fusobacteria, *Leptotrichia amnionii* in the BV sample shifted to an uncharacterized species of *Leptotrichia*. Post-tinidazole Actinobacteria were enriched for *Propionibacteria* and *Corynebacteria* at the expense of *G. vaginalis*. Comparison of 70 *G. vaginalis* clones from the broad-spectrum PCR library showed isolates clustering into two subgroups different by 1%. Most of the clones from the acute BV sample belonged to the larger cluster, whereas most of the post-tinidazole clones belonged to the smaller subgroup. These species and strain shifts may reflect succession of isolates that are less susceptible to or more tolerant of tinidazole, consistent for example, with reports of recent or regional increases in metronidazole resistance among *G. vaginalis* isolates. Alternatively, arising species/ strains may be better suited to the lower pH and otherwise altered environment. These shifts also support the argument that PB-primers are more likely to catch these changing populations than are species-specific primers.

The use of group-specific primers in the vaginal microbiome to date targets only 4 groups. The coverage of *Veillonella*-related genera in the Ribosomal Database Project (RDP) is about the same as in studies described herein but the RDP primers mismatch with *Dialister*; their coverage of LB is 7% compared to studies described herein (see Example 1) and mismatches with most vaginal LB spp.; their coverage of Bacteroidales is 30% of studies described herein (see Example 1) and excludes *Bacteroides* spp.; and their coverage of *Atopobium*-related Coriobacteridae is similar to studies described herein (see Example 1). The present disclosure demonstrates both the potential of LB-blocking and PB-qPCR for characterizing both the healthy and abnormal vaginal microbiome in depth, and that it is an enhancement of existing species and group-specific qPCR approaches.

Despite use of both broad-spectrum and species-specific PCR, the etiology and microbial ecology of BV is complex. It is not yet fully known what initiates the changes in microbial populations as the transition from healthy to abnormal composition, what causes refractory or recurrent responses to treatment, whether there is a sexual transmission component, or whether specific compositions pose higher risks for the complications associated with BV. Understanding the pathobiology of BV requires that the lower abundance species are identified as soon as they begin their rise, and assumes that some of these may never reach the million cell threshold. Effective treatment of BV should have as an endpoint, not merely restoration of LB species to dominance, but reduction of BV-associated anaerobes below a selected threshold.

Disclosed herein are systems and methods for: diagnosing BV, monitoring the treatment of BV; choosing an appropriate therapy for BV; and/or predicting success or failure of therapy of BV in a subject.

In particular embodiments, a $\Delta$Cq score of below 3 leads to a diagnosis of BV, predicts the recurrence of BV; directs continued treatment of BV; and/or classifies a treatment as ineffective. In additional embodiments, a $\Delta$Cq score of 3 or above leads to a diagnosis of a healthy vaginal microbiome, predicts non-recurrence of BV; directs cessation of BV treatment; and/or classifies a treatment as effective. As will be understood by one of ordinary skill in the art, $\Delta$Cq scores can be calculated by determining the difference between LB-blocked versus unblocked samples. Appropriate control conditions are adopted to allow meaningful comparison between the sample types. For example, in one embodiment, LB-blocked versus unblocked samples are run in parallel using the same equipment.

The setting of the clinically relevant threshold of $\Delta$Cq score at $\geq$3 or <3 is based on a best match to Nugent scoring. Based on the teachings herein, one of ordinary skill in the art can derive similar clinically-relevant thresholds based on Amsel scoring or other BV assays including, e.g., microbiological assays; molecular probe assays (AFFIRM™ VPIII Microbial Identification Test); PCR-based assays; combinations of assays; etc. Thus, while the Nugent-matched $\Delta$Cq scores of $\geq$3 or <3 are particularly provided, the current disclosure extends to clinically relevant thresholds matched to other assay types as well.

An additional embodiment comprises: amplifying total bacterial DNA present in a vaginal sample from the subject; and amplifying non-LB species DNA in the sample by specifically blocking amplification of bacterial DNA from LB species, wherein the relative abundance of non-LB species is indicative of the presence of BV.

In other embodiments, the methods comprise characterizing a vaginal microbiome in a subject comprising amplifying total bacterial DNA present in the sample; and amplifying non-LB species DNA in the sample by specifically blocking amplification of DNA from one or more LB species, wherein the relative abundance of non-LB species is indicative of the health of the vaginal microbiome.

Another method disclosed herein comprises characterizing a microbiome in a vaginal sample from a subject comprising amplifying total bacterial DNA present in the sample from the vagina; and amplifying non-dominant species DNA in the sample by specifically blocking amplification of DNA from one or more dominant species, wherein the relative abundance of non-dominant species is indicative of the health of the vaginal microbiome. In this method, the dominant species of bacteria in the microbiome is determined by amplifying total DNA from a healthy subject and identifying the dominant species.

Microbiome samples can be obtained using standard techniques relevant to the particular microbiome under consideration. For example, vaginal microbiome samples can be obtained by vaginal lavage, Papanicolaou smear, tissue biopsy, and the like.

DNA can be prepared from the sample by standard DNA isolation techniques. In one embodiment, bacteria from a sample can be lysed, followed by vigorous reciprocal shaking at room temperature for 30 min. The DNA can then extracted, precipitated, washed and stored in a suitable buffer at $-20°$ C. until testing.

In certain aspects of the systems and methods disclosed herein, the amplification of bacterial DNA can be performed by PCR, such as real-time or quantitative PCR (qPCR). qPCR is a laboratory technique based on the PCR, which is used to amplify and simultaneously quantify a targeted DNA molecule. For one or more specific sequences in a DNA sample, qPCR enables both detection and quantification. The quantity can be either an absolute number of copies or a relative amount when normalized to DNA input or additional normalizing genes. The procedure follows the general principle of PCR; its key feature is that the amplified DNA is detected as the reaction progresses in real time. This is a different approach compared to standard PCR, where the product of the reaction is detected at its end.

Two common methods for detection of products in qPCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target. In the first non-specific method, a DNA-binding dye binds to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products, including nonspecific PCR products (such as Primer dimer). This can potentially interfere with, or prevent, accurate quantification of the intended target sequence.

Sequence-specific fluorescent reporter probes detect only the DNA containing the probe sequence(s) of interest; therefore, use of the reporter probe significantly increases specificity, and enables quantification even in the presence of non-specific DNA amplification. Fluorescent probes can be used in multiplex assays—for detection of several genes in the same reaction—based on specific probes with different-colored labels, provided that all targeted genes are amplified with similar efficiency.

The second sequence-specific method relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the Taq polymerase breaks the reporter-quencher proximity and thus allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

qPCR can be used to quantify nucleic acids by two common methods: relative quantification and absolute quantification. Relative quantification is based on internal reference genes to determine fold-differences in expression of the target gene. Absolute quantification gives a more exact number of target DNA molecules by comparison with DNA standards.

A commonly-employed method of DNA quantification by qPCR relies on plotting fluorescence against the number of cycles on a logarithmic scale. A threshold for detection of DNA-based fluorescence is set slightly above background. The number of cycles at which the fluorescence exceeds the threshold is called the threshold cycle ($C_t$) or, according to the MIQE guidelines, quantification cycle ($C_q$). During the exponential amplification phase, the sequence of the DNA target doubles every cycle. For example, a DNA sample whose $C_q$ precedes that of another sample by 3 cycles contained $2^3=8$ times more template. However, the efficiency of amplification is often variable among primers and templates. Therefore, the efficiency of a primer-template combination can be assessed in a titration experiment with serial dilutions of DNA template to create a standard curve of the change in $C_q$ with each dilution. The slope of the linear regression can then be used to determine the efficiency of amplification, which is 100% if a dilution of 1:2 results in a $C_q$ difference of 1. The cycle threshold method makes several assumptions of reaction mechanism and has a reliance on data from low signal-to-noise regions of the amplification profile that can introduce variance during the data analysis.

In qPCR, a template (the DNA to be amplified) can be prepared and the reporter probe (primer) can be added. As the reaction commences, during the annealing stage of the PCR both probe and primers anneal to the DNA target. Polymerisation of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a cycler, and its geometric increase corresponding to exponential increase of the product is used to determine the quantification cycle ($C_q$) in each reaction.

The reaction conditions, including annealing temperature, number of cycles, length and temperature of each cycle, can be determined for each group of primers. Exemplary reaction conditions are found in the Examples and in Tables 3A-3D.

Amplification of total bacterial DNA can utilize broadly reactive primers described in the Examples and in, for example, Table 2 using at least one forward primer and at least one reverse primer. In one embodiment, up to five forward and up to five reverse primers can be used simultaneously to amplify total bacterial DNA from samples. In certain embodiments, one, two, three, four, or five forward primers and one, two, three, four, or five reverse primers are used simultaneously. In one embodiment, five forward and five reverse primers are used simultaneously to amplify total bacterial DNA from a sample. More than five forward and/or reverse primers can also be used. One embodiment includes up to 100 forward primers and up to 100 reverse primers or any integer in between five and 100 including, for example, 10, 15, 20, 30, 40, 50, 60, 70, 80 or 90.

Amplification of non-dominant bacterial species DNA is accomplished by blocking amplification of dominant species DNA with blocking primers. If the dominant species is LB, the blocking primers can comprise at least one forward primer and at least one reverse primer which partially overlap binding sites for sequences on the LB genome and wherein the primer melting temperatures are at least 68° C. In one embodiment, the blocking primers are as disclosed in the Examples and in Table 2.

Titer and Cp values from the PCR reactions can be calculated as described in the Examples. These values are cycler specific. For example, for vaginal lavage amplifications conducted using the LightCycler 480 II Real-Time PCR System (Roche Applied Science), Cp values can be converted to molecules by comparison to Cp values of a standard curve from the same run derived from 4-8 10-fold serial dilutions of an amplicon quantified using the Quant-iT assay (Invitrogen). Molecules per microliter can be converted to cells per 5 ml lavage, assuming an average of five ribosomal genes per cell and proportioned to the ratio of the volume of the lavage used in the DNA prep and its final volume.

The results of the PCR amplification can then be used to determine the health of the vaginal microbiome. The ratio of dominant bacteria, such as LB for the vaginal microbiome, to the non-dominant species can be determined.

For the vaginal microbiome, the ratio is useful for diagnosing BV and/or predicting the recurrence of BV. Where the systems and methods are used to assess the vaginal microbiome, a ratio of non-LB species to LB species of more than 1:99 is indicative of BV or a disturbed profile in the subject. Ratios of non-LB species to LB species of more than 1.1:98.9; 1.2:98.8; 1.3:98.7; 1.4:98.6; 1.5:98.5; 1.6:98.4; 1.7:98.3; 1.8:98.2 or 1.9:98.1; can also be indicative of BV or a disturbed profile in the subject. Ratios of non-LB species to LB species of more than 2:98 can also be indicative of acute BV.

The systems and methods are also useful for monitoring the treatment of BV, where if the ratio of non-LB species to LB species is more than 1:99, the treatment is ineffective and a new treatment is initiated in the subject. In this scenario, the disclosed method can be performed before treatment is initiated and then periodically after the onset of treatment to determine if the treatment is decreasing the non-LB bacterial load in the vaginal microbiome. If the non-LB bacterial load is decreased below threshold, compared to pre-treatment or an earlier treatment time point, the treatment is effective and should be completed as appropriate. If the non-LB bacterial load not decreased, compared to pre-treatment or an earlier treatment time point, then the treatment is ineffective and a new treatment should be initiated in the subject. If the non-LB bacterial load is unchanged, the treatment can be maintained and the patient retested to determine if the treatment becomes effective, or the treatment can be stopped and changed as appropriate.

In particular embodiments, a ΔCq score of below 3 leads to a diagnosis of BV, predicts the recurrence of BV; directs continued treatment of BV; and/or classifies a treatment as ineffective. In additional embodiments, a ΔCq score of 3 or above leads to a diagnosis of a healthy vaginal microbiome, predicts non-recurrence of BV; directs cessation of BV treatment; and/or classifies a treatment as effective.

In another aspect, the systems and methods are useful for choosing the appropriate therapy for BV. If the patient is determined to have BV according to a disclosed system or method, the identity of non-LB species or category in the sample can be determined and a therapy can be initiated in the subject based on this information. Additionally, based on the identity of the non-LB species or category in the sample, the success or failure of particular therapies can be predicted.

The disclosed methods can also encompass systems and methods to identify non-dominant species in microbiomes by performing melting curve analyses. As used herein a "melting curve analysis" refers to an assessment of the dissociation-characteristics of double-stranded DNA during heating. As the temperature is raised, the double strand DNA begins to dissociate leading to a rise in the absorbance intensity, hyperchromicity. The temperature at which 50% of the DNA is denatured is known as the melting point. Specifically, melting curves allow a comparison of the melting temperatures of amplification products. Different double stranded DNA (dsDNA) molecules melt at different temperatures, dependent on a number of factors including GC content, amplicon length, secondary and tertiary structure, and the chemical formulation of the reaction chemistry.

To produce melting curves, the final PCR product can be exposed to a temperature gradient from 50° C. to 95° C. while fluorescence readouts are continually (or substantially intermittently) collected. The increase in temperature causes denaturation of all dsDNA. The point at which the dsDNA melts into single-stranded DNA (ssDNA) is observed as a drop in fluorescence as the dye dissociates. The melting curves can be converted to distinct melting peaks by plotting the first negative derivative of the fluorescence as a function of temperature. Products of different lengths and sequences melt at different temperatures and are observed as different peaks. Amplicons that differ by as few as a single nucleotide can be distinguished by their melting peaks. Melting curve variations can be assessed in unblocked samples to detect and characterize non-dominant content. In one embodiment directed to vaginal microbiomes, melting curve variations can be assessed in unblocked samples to detect and characterize non-LB content in the 5-100% range, and in the LB-blocked sample to detect these groups at <<5%.

For melting curve analyses regarding the microbiomes, genus-specific primers spanning the internal transcribed spacer region between large and small rDNA genes can be used to create an amplicon which is most often from a single dominant species. The species can be identified from its melting curve, $1^{st}$ derivative, by subtracting all the fluorescence values along the temperature axis from the corresponding values from each reference species' melting curve. This difference can then be added, and the sum is close to 0 if the reference species and the unknown species are the same, but not close to 0 if different. In the vaginal microbiome, bacterial genera for which species are involved include LB, *Streptococcus, Staphylococcus*, and *Mycoplasma*.

Melting curves in BV analyses can also be used to subcategorize broader classes of vaginal bacteria. The broad categories can be assigned based on the melt temperatures of the non-LB components with and without LB blocker.

Melting curves ($1^{st}$ derivative) with peaks or shoulders outside of the window that represents LB species indicate some level of abnormal bacteria. If this is seen without blocker, the relative level of the abnormal bacteria is high. If only with blocker, the relative level of abnormal bacteria is low. The compositional class further depends on whether these peaks or shoulders are at a higher temperature than LB, lower, or coincident temperatures. Each of these possibilities is scrutinized to determine which parameter is most predictive of relapse or low initial response to treatment.

Melting curves in bacteria are also used to identify the species of non-dominant bacteria. In this case, the primers flank the internal transcribed spacer, but are not broad spectrum, and target only a specific branch or genus so that the amplicons detect all or most species within the target, and the melting curve identifies which species or subset of possible species are present. This approach is useful in cases where multiple species within the genus cause infection, and especially where growing cultures is slow or problematic.

ΔCq scores can also be combined with information derived from non-LB melt curves to classify samples as "cured" or "at risk for recurrence" (referred to as "combined scores" herein). Combined scores are based primarily on ΔCq score with a determination of whether there are non-LB melt curves (FIG. 16) present without blocking (higher relative titers) versus only with blocking (lower relative titers). For example, a ΔCq of ≥3 in combination with no melt curves (Tm) above a defined temperature threshold when run in the presence of LB blockers indicates a cure. If, however, melt curves are observed above the defined temperature threshold in the presence of LB blockers, a patient could be classified as at risk for recurrence, even if currently asymptomatic. Alternatively, if no melt curves are observed above the defined temperature threshold in the presence of LB blockers, yet the ΔCq score is <3, a patient could be classified as at risk for recurrence, even if currently asymptomatic.

Within the context of combined scores, above a defined temperature threshold can include above 50° C.; above 60° C.; above 70° C.; above 80° C.; above 81° C.; above 82° C.; above 83° C.; above 84° C.; above 85° C.; above 86° C.; above 87° C.; above 88° C.; above 89° C.; above 90° C.; above 91° C.; or above 92° C. Above a defined temperature threshold can also include ranges such as 80° C.-92° C.; 82° C.-90° C.; or 84° C.-88° C.

In another embodiment, the defined temperature range is in relation to the Tm of LB. For example, the defined temperature range can be +1° C. from an LB peak; +2° C. from an LB peak; +3° C. from an LB peak; +4° C. from an LB peak; +5° C. from an LB peak; +6° C. from an LB peak; +7° C. from an LB peak; +8° C. from an LB peak; +9° C. from an LB peak; +10° C. from an LB peak; −1° C. from an LB peak; −2° C. from an LB peak; −3° C. from an LB peak; −4° C. from an LB peak; −5° C. from an LB peak; −6° C. from an LB peak; −7° C. from an LB peak; −8° C. from an LB peak; −9° C. from an LB peak; or −10° C. from an LB peak.

In particular examples of the foregoing, vaginal LB species can be identified as a group by their Tm peak between 84.3° C. and 87.1° C. Relative to LB peaks, BV-associated anaerobes appear as peaks shifted as follows: *Gardnerella vaginalis*, BVAB2, and *Dialister* shift +2-2.3° C. (BV-2 no block in FIG. 16), *Atopobium vaginae* +2.5° C., BVAB1 −1° C., *Leptotrichia amnionii* −2-2.5° C. *Prevotella, Mycoplasma, Streptococcus*, and *Enterococcus* spp. have melts in the range of LB spp.

The approaches described for vaginal microbiomes herein can also be applied to a variety of other microbiomes. Exemplary additional microbiomes include, but are not limited to a gastrointestinal microbiome, a skin microbiome, a pulmonary microbiome, an oral microbiome, a conjuctival microbiome, or a genitourinary microbiome. Within each microbiome, certain diseases or disorders are associated with alterations in dominant and non-dominant species.

The gastrointestinal microbiome comprises the human flora of microorganisms that normally live in the digestive tract and can perform a number of useful functions for their hosts. The average human body, consisting of about ten trillion cells, has about ten times that number of microorganisms in the gut. Bacteria make up most of the flora in the colon and 60% of the dry mass of feces. This fact makes feces an ideal source to test for gut flora for any tests and experiments by extracting the nucleic acid from fecal specimens, and bacterial 16S rRNA gene sequences are generated with bacterial primers. This form of testing is also often preferable to more invasive techniques, such as biopsies. Somewhere between 300 and 1000 different species live in the gut, with most estimates at about 500. Exemplary dominant species associated with the gastrointestinal microbiome include one or more of *Bacteroides fragilis, Bacteroides melaninogenicus, Bacteroides oralis, Enterococcus faecalis, Escherichia coli, Klebsiella* sp., *Enterobacter* sp., *Bifidobacterium bifidum, Staphylococcus aureus*, LB, *Clostridium perfringens, Proteus mirabilis, Peptostreptococcus* sp., *Peptococcus* sp., *Clostridium tetani, Clostridium septicum, Pseudomonas aeruginosa*, and *Salmonella enteritidis*. Exemplary diseases associated with the gastrointestinal microbiome include chronic gastritis, and peptic ulcer disease (associated with *Helicobacter pylori*).

The skin microbiome includes bacterial species associated with the skin, hair and nails. A study of twenty skin sites on each of ten healthy humans found 205 identified genera in nineteen bacterial phyla, with most sequences assigned to four phyla: Actinobacteria (51.8%), Firmicutes (24.4%), Proteobacteria (16.5%), and Bacteroidetes (6.3%). There are three main ecological areas: sebaceous, moist, and dry. *Propionibacteria* and *Staphylococci* species are the dominant species in sebaceous areas. In moist places on the body *Corynebacteria* together with *Staphylococci* dominate. In dry areas, there is a mixture of species but b-Proteobacteria and Flavobacteriales are dominant. Exemplary diseases associated with the skin microbiome include atopic dermatitis, rosacea, psoriasis, and acne.

The lung microbiome or pulmonary microbial community is a complex variety of microbes found in the lower respiratory tract particularly on the mucus layer and the epithelial surfaces. These microbes include bacteria, yeasts, viruses and bacteriophages. The bacterial part of the microbiome has been addressed more deeply. It consists of nine dominant genera including *Prevotella, Sphingomonas, Pseudomonas, Acinetobacter, Fusobacterium, Megasphaera, Veillonella, Staphylococcus*, and *Streptococcus*. Harmful or potentially harmful bacteria include *Moraxella catarrhalis, Haemophilus influenzae*, and *Streptococcus pneumoniae*. Exemplary diseases associated with the pulmonary microbiome include chronic obstructive pulmonary disease (COPD), asthma, and cystic fibrosis.

The oral cavity, or mouth, includes several distinct microbial habitats, such as teeth, gingival sulcus, attached gingiva, tongue, cheek, lip, hard palate, and soft palate. Contiguous with the oral cavity are the tonsils, pharynx, esophagus, Eustachian tube, middle ear, trachea, lungs, nasal passages, and sinuses. The human oral microbiome is defined as all the microorganisms that are found on or in the human oral cavity and its contiguous extensions (stopping at the distal esophagus), though mostly related to within the oral cavity. Different oral structures and tissues are colonized by distinct microbial communities. Approximately 280 bacterial species from the oral cavity have been isolated in culture and formally named. It has been estimated that less than half of the bacterial species present in the oral cavity can be cultivated using anaerobic microbiological methods and that there are likely 500 to 700 common oral species. Cultivation-independent molecular methods, primarily using 16S rRNA gene-based cloning studies, have validated these estimates by identifying approximately 600 species or phylotypes.

Exemplary dominant species associated with the oral microbiome include one or more from the genera *Streptococcus, Abiotrophia, Gemella*, and *Granulicatella, Fusobacterium*, LB, *Staphylococcus, Corynebacteria*, and *Leptotrichia*. Exemplary diseases associated with the oral microbiome include dental caries; periodontitis, including chronic adult periodontitis; endodontic infections; alveolar osteitis; gingivitis, including acute necrotizing ulcerative gingivitis; and tonsillitis.

A small number of bacteria are normally present in the conjunctiva. *Staphylococcus epidermidis* and certain coryneforms such as *P. acnes* are dominant while. *S. aureus*, streptococci, *Haemophilus* sp. and *Neisseria* sp. sometimes occur. Other pathogens able to infect the conjunctiva include *Neisseria gonorrhoeae* and *Chlamydia trachomatis*. Exemplary diseases associated with the conjunctival microbiome include conjunctivitis.

Systems disclosed herein can also include kits and methods can include using kits disclosed herein. Kits can be assembled for the determination of organ-specific microbiome snapshots. In various embodiments, the kits contain all reagents necessary to perform the disclosed methods, or a subset of the reagents necessary to perform the disclosed methods. The minimum contents of the kit include a first set of primers comprising at least one forward primer and at least one reverse primer broadly reactive for bacterial DNA; at least one set of blocking primers comprising at least one forward blocking primer and at least one reverse blocking primer broadly reactive to a dominant species of bacteria in a microbiome site; and instructions for (1) obtaining a sample from the microbiome site, (2) amplifying the total bacterial DNA in the sample by PCR using the first primer set, (3) selectively amplifying the non-dominant DNA in the sample using the first primer set and the second blocking primer set, (4) calculating the relative abundance of non-dominant species in the sample, and (5) optionally instructions and reagents for high resolution melt analysis. The kit will also include control templates representing common microbiome species as quality controls.

Also provided in this disclosure are kits for the determination of vaginal-specific microbiome snapshots. In various embodiments, the kits contain all reagents necessary to perform the disclosed methods, or a subset of the reagents necessary to perform the disclosed methods. The minimum contents of the kit include a first set of primers comprising at least one forward primer and at least one reverse primer broadly reactive for vaginal DNA; a set of blocking primers comprising at least one forward blocking primer and at least one reverse blocking primer broadly reactive to a dominant species of bacteria in a vagina; and instructions for (1) obtaining a sample from the vagina, (2) amplifying the total bacterial DNA in the sample by PCR using the first primer set, (3) selectively amplifying the non-dominant DNA in the sample using the first primer set and the second blocking primer set, and (4) calculating the relative abundance of non-dominant species in the sample. The first primer set can include, but is not limited to, BU4F+, BU6R+, 8F+, 1501R1, 1501R2, 1492R, 27F, 338R, 341F, 806R, 338F, and 534R. The second blocking primer set can include, but is not limited to, LBB3p and LBB4p. The kits can also include control templates representing common vaginal species as quality controls.

Optionally, the kits can also contain PCR reagents such as DNA purification systems, enzymes, buffers, labels, and other reagents that are commercially available from a number of vendors including, but not limited to, Invitrogen, Qiagen, and Roche Applied Science.

Exemplary Embodiments—Set 1

1. A method of characterizing a microbiome associated with an organ from a subject comprising: amplifying total bacterial DNA present in the sample from the microbiome; and amplifying non-dominant species DNA in the sample by specifically blocking amplification of DNA from one or more dominant species, wherein the relative abundance of non-dominant species is indicative of the health of the microbiome.
2. A method of embodiment 1, wherein the dominant species of bacteria in the microbiome is determined by amplifying total DNA from a healthy subject and identifying the dominant species.
3. A method of embodiments 1 or 2, wherein the microbiome is a gastrointestinal microbiome, a pulmonary microbiome, an oral microbiome, a skin microbiome, a genitourinary microbiome, or a conjunctival microbiome.
4. A method of embodiment 3, wherein the gastrointestinal microbiome is a stomach microbiome, an intestinal microbiome, or a colon microbiome.
5. A method of embodiment 3, wherein the dominant species of the gastrointestinal microbiome is one or more of *Staphylococcus epidermidis, S. aureus, Staphylococcus warneri, Streptococcus pyogenes, Streptococcus mitis, Propionibacterium acnes, Corynebacterium* spp., *Acinetobacter johnsonii,* or *Pseudomonas aeruginosa*.
6. A method of embodiment 3, wherein the pulmonary microbiome is a lung microbiome, a nasal microbiome, or a sinus microbiome.
7. A method of embodiment 3, wherein the dominant species of the pulmonary microbiome is one or more species of the genera *Prevotella, Sphingomonas, Pseudomonas, Acinetobacter, Fusobacterium, Megasphaera, Veillonella, Staphylococcus,* or *Streptococcus*.
8. A method of embodiment 3, wherein the dominant species of the oral microbiome is one or more of the genera *Streptococcus, Abiotrophia, Gemella,* and *Granulicatella, Fusobacterium*, LB, *Staphylococcus, Corynebacteria,* or *Leptotrichia*.
9. A method of embodiment 3, wherein the genitourinary microbiome is a vulva microbiome or a vaginal microbiome.
10. A method of embodiment 3, wherein the dominant species of the genitourinary microbiome is one or more of a LB species, *Gardnerella vaginalis,* or *Trichomonas vaginalis*.
11. A method of embodiment 3, wherein the dominant species of the conjuctival microbiome is one or more of *Staphylococcus epidermidis, P. acnes, S. aureus,* streptococci, *Haemophilus* sp. and *Neisseria* sp.
12. A method of embodiment 1, wherein the sample is obtained from the stomach, the colon, the intestine, the mouth, the nasal cavity, the nasal sinuses, the skin, the conjunctiva, the vulva, or the vagina.
13. A method of embodiment 1, wherein the amplification of bacterial DNA is performed by PCR.
14. A method of embodiment 13, wherein the PCR is quantitative PCR (qPCR).
15. A method of any one of embodiments 1-14, wherein the total bacterial DNA is amplified with at least one forward primer and at least one reverse primer broadly reactive with bacterial DNA.
16. A method of any one of embodiments 1-15, wherein amplification of the dominant bacterial DNA is blocked by at least one forward blocking primer and at least one reverse blocking primer that specifically bind to unique sequences on the dominant bacterial genome.
17. A method of any one of embodiments 1-16, wherein the relative abundance of non-dominant species is determined by calculating a ratio of non-dominant species to dominant species in the sample.
18. A method of any one of embodiments 1-17, wherein the method is used for the diagnosis of a disease or disorder in the subject, and wherein if the level or ratio of non-dominant species is higher than or different from a pre-determined threshold level or ratio specific for the microbiome from which the sample was obtained, the subject has a disease or disorder of the microbiome's associated organ from which the sample was obtained.
19. A method of any one of embodiments 1-18, wherein the method is used for monitoring the treatment of a disease or disorder in the subject, and wherein if the level or ratio of non-dominant species is higher than or different from a pre-determined threshold level or ratio specific for the microbiome from which the sample was obtained, the treatment is ineffective and a new treatment is initiated in the subject.
20. A method of any one of embodiments 1-19, wherein the method is used for monitoring the treatment of a disease or disorder in the subject, and wherein if the level or ratio of non-dominant species is higher than or different from a pre-determined threshold level or ratio specific for the microbiome from which the sample was obtained, the treatment is effective and the prescribed course of treatment should be completed in the subject.
21. A method of any one of embodiments 1-20, wherein the method is used for choosing the appropriate therapy for a disease or disorder.
22. A method of determining the identity of at least one non-dominant bacterial species within a microbiome comprising: amplifying bacterial DNA present in a sample from the microbiome using pan-bacterial primers wherein amplification of dominant bacterial species is blocked with dominant species blocking primers; subjecting the resulting amplification products to high-resolution melt analysis to generate melt curves; and comparing the melt curves with control melt curves previously established for individual bacterial species or genera thereby identifying the bacterial species in the microbiome sample.
23. A method of embodiment 22, wherein the microbiome is a gastrointestinal microbiome, a pulmonary microbiome, an oral microbiome, a skin microbiome, a genitourinary microbiome, or a conjunctival microbiome.

24. A method of embodiment 22, wherein the gastrointestinal microbiome is a stomach microbiome, an intestinal microbiome, or a colon microbiome.
25. A method of embodiment 22, wherein the pulmonary microbiome is a lung microbiome, a nasal microbiome, or a sinus microbiome.
26. A method of embodiment 22, wherein the genitourinary microbiome is a vulva microbiome or a vaginal microbiome.
27. A method of embodiment 22, wherein the sample is obtained from the stomach, the colon, the intestine, the mouth, the nasal cavity, the nasal sinuses, the skin, the conjunctiva, the vulva, or the vagina.
28. A method of embodiment 22, wherein the amplification of bacterial DNA is performed by PCR.
29. A method of embodiment 28, wherein the PCR is qPCR.
30. A method of any one of embodiments 22-29, wherein the total bacterial DNA is amplified with at least one forward primer and at least one reverse primer broadly reactive with bacterial DNA.
31. A method of any one of embodiments 22-30, wherein amplification of dominant bacterial DNA is blocked by at least one forward blocking primer and at least one reverse blocking primer that specifically bind to unique sequences on the dominant bacterial genome.
32. A method of any one of embodiments 2-31, wherein the identified species is a non-dominant species.
33. A method of any one of embodiments 22-32, wherein the method is used for the diagnosis of a disease or disorder in the subject wherein the presence of one or more identified bacterial species in the microbiome indicates the subject has a disease or disorder of the organ from which the microbiome sample was obtained.
34. A method of any one of embodiments 22-33, wherein the control melt curves are part of a database of melt curves representing the majority of bacteria present in the microbiome.
35. A kit for the identification of at least one bacterial species within a microbiome comprising: a first set of primers broadly reactive for total bacterial DNA; and instructions for obtaining a sample from the microbiome, amplifying the total bacterial DNA in the sample by PCR using the first primer set, determining the high resolution melting curve of the amplification products, and identifying the bacterial species within the composition of the sample by comparison of the sample melt curves to standardized bacterial melt curves.
36. A kit of embodiment 35, further comprising blocking primers comprising at least one forward blocking primer and at least one reverse blocking primer broadly reactive to a dominant species of bacteria in the microbiome sample.
37. A kit of embodiment 35, wherein the kit further contains reagents for performing PCR and high resolution melt analysis.

Exemplary Embodiments—Set 2

1. A method of diagnosing and/or predicting the success or failure of therapy of BV in a subject comprising: amplifying total bacterial DNA present in a vaginal sample from the subject; and selectively amplifying non-LB species DNA in the sample by amplifying total bacterial DNA while specifically blocking amplification of bacterial DNA from LB species, and diagnosing the subject with BV and/or predicting the failure of a therapy if the relative abundance of non-LB species to LB species exceeds a ratio of 1:99.
2. A method of embodiment 1, wherein the vaginal sample is a vaginal lavage.
3. A method of embodiments 1 or 2, wherein the amplification of bacterial DNA is performed by PCR.
4. A method of embodiment 3, wherein the PCR is qPCR.
5. A method of any one of embodiments 1-4, wherein the total bacterial DNA is amplified with at least one forward primer and at least one reverse primer are selected from BU4F+, BU6R+, 8F+, 1501R1, 1501R2, 1492R, 27F, 338R, 341F, 806R, 338F, and 534R.
6. A method of any one of embodiments 1-5, wherein amplification of LB species DNA is blocked by at least one forward blocking primer and at least one reverse blocking primer which partially overlap binding sites for sequences on the LB genome and wherein the blocking primer melting temperatures are at least 68° C.
7. A method of embodiment 6, wherein the at least one forward blocking primer and at least one reverse blocking primer are selected from LBblocker3, LBB3p, LBblocker4, and LBB4p.
8. A method of any one of embodiments 1-7, further comprising directing a treatment if a BV diagnosis is made.
9. A method of any one of embodiments 1-7, further comprising changing a treatment if a prediction of treatment failure is made.
10. A method of any one of embodiments 1-9, further comprising monitoring the treatment of BV, and wherein if the ratio of non-LB species to LB species is more than 1:99 determining that a treatment is ineffective and initiating a new treatment in the subject.
11. A method of any one of embodiments 1-9, further comprising monitoring the treatment of BV, and wherein if the ratio of non-LB species to LB species is less than 1:99, the treatment is effective and the prescribed course of treatment is completed in the subject.
12. A method of any one of embodiments 1-11 further comprising determining the identity of non-LB species in the sample.
13. A method of embodiment 12, further comprising choosing an appropriate therapy based on the identity of the non-LB species.
14. A method of embodiments 12 or 13, wherein the determining comprises performing a melting curve analysis on resulting amplicons to determine the identity of non-LB species.
15. A method of embodiments 12 or 13, wherein the determining comprises performing a melting curve analysis on resulting amplicons to categorize classes of vaginal bacteria.
16. A kit for assessing health of a vaginal microbiome comprising: a first set of primers comprising forward primers and reverse primers that support amplification of bacterial DNA present in the vaginal microbiome; a second set of primers comprising at least one forward blocking primer and at least one reverse blocking primer that block amplification of LB species DNA; and instructions for (i) obtaining a vaginal sample, (ii) amplifying the total bacterial DNA in the sample by PCR using the first primer set, (iii) amplifying the non-LB DNA in the sample using the first primer set in the presence of the second blocking primer set, and (iv) calculating the relative abundance of non-LB species to LB species in the sample.
17. A kit of embodiment 16, wherein the instructions direct that the vaginal sample be a vaginal lavage.
18. A kit of embodiments 16 or 17, wherein the instructions direct that amplification of bacterial DNA be performed by PCR.
19. A kit of embodiment 18, wherein the instructions direct that PCR be qPCR.

20. A kit of any one of embodiments 16-19, wherein the at least one first forward primer and at least one first reverse primer are selected from BU4F+, BU6R+, 8F+, 1501R1, 1501R2, 1492R, 27F, 338R, 341F, 806R, 338F, and 534R.

21. A kit of any one of embodiments 16-20, wherein the blocking primers partially overlap binding sites for sequences on the LB genome and wherein the blocking primer melting temperatures are at least 68° C.

22. A kit of any one of embodiments 16-21, wherein the blocking primers are selected from LBblocker3, LBB3p, LBblocker4, and LBB4p.

23. A kit of any one of embodiments 16-22, wherein the relative abundance of non-LB species is determined by calculating a ratio of non-LB species to LB species in the sample.

24. A kit of embodiment 23, wherein informative ratios of the relative abundance of non-LB species to LB species in the sample include 20:80; 19:81; 18:82; 17:83; 16:84; 15:85; 14:86; 13:87; 12:88; 11:89; 10:90; 9:91; 8:92; 7:93; 6:94; 5:95; 4:96; 3:97; 2:98; 1.9:98.1; 1.8:98.2; 1.7:98.3; 1.6:98.4; 1.5:98.5; 1.4:98.6; 1.3:98.7; 1.2:98.8; 1.1:98.9; 1:99; 0.9:99.1; 0.8; 99.2; 0.7:99.3 or 0.6:99.4. In particular embodiments, treatment or diagnosis cut-offs are made at the 1:99 ratio. LB species at 99% or greater represent a healthy vaginal microbiome. Any level less than 99% provides an indication that treatment is necessary and any level less than 98% represents acute BV.

25. A kit of embodiment 24, wherein in the instructions direct a diagnosis of BV if the ratio of non-LB species to LB species is 20:80; 19:81; 18:82; 17:83; 16:84; 15:85; 14:86; 13:87; 12:88; 11:89; 10:90; 9:91; 8:92; 7:93; 6:94; 5:95; 4:96; 3:97; 2:98; 1.9:98.1; 1.8:98.2; 1.7:98.3; 1.6:98.4; 1.5:98.5; 1.4:98.6; 1.3:98.7; 1.2:98.8; or 1.1:98.9. Any ratio having 2% or more of non-LB species can be indicative of acute BV.

26. A kit of embodiment 24, wherein the instructions direct monitoring of a treatment for BV, and wherein if the ratio of non-LB species to LB species is 1.1:98.9 or a higher level of non-LB species, the instructions determine that the treatment is ineffective and direct that a new treatment be initiated in the subject.

27. A kit of embodiment 24, wherein instructions direct monitoring the treatment of BV, and wherein if the ratio of non-LB species to LB species is 1:99 or a lower level of non-LB species, the instructions determine that the treatment is effective and direct that the prescribed course of treatment be completed in the subject.

28. A kit of any one of embodiments 16-27, wherein the instructions direct a treatment for BV.

29. A kit of any one of embodiments 16-28, wherein the instructions direct prediction of treatment failure if the ratio of non-LB species to LB species is 1.1:98.9 or has a higher level of non-LB species.

30. A kit of any one of embodiments 16-29, wherein the instructions further comprise directions for conducting melting curve analyses on resultant PCR amplicons.

31. A method of characterizing health of a vaginal microbiome from a sample of a subject comprising: amplifying total bacterial DNA present in the sample; and selectively amplifying non-LB species DNA in the sample by amplifying total bacterial DNA while specifically blocking amplification of DNA from one or more LB species, wherein the relative abundance of non-LB species to LB species is indicative of the health of the vaginal microbiome.

32. A method of embodiment 31, wherein the amplification of bacterial DNA is performed by PCR.

33. A method of embodiments 31 or 32, wherein the PCR is qPCR.

34. A method of any one of embodiments 31-33, wherein the total bacterial DNA is amplified with at least one forward primer and at least one reverse primer broadly reactive with bacterial DNA.

35. A method of any one of embodiments 31-34, wherein amplification of the LB bacterial DNA is blocked by at least one forward blocking primer and at least one reverse blocking primer which specifically bind to unique sequences on the LB bacterial genome and wherein the blocking primer melting temperatures are at least 68° C.

36. A method of any one of embodiments 31-35, wherein the relative abundance of non-LB species is determined by calculating a ratio of non-LB species to dominant species in the sample.

37. A method of any one of embodiments 31-36, wherein the method is used for the diagnosis of a disease or disorder in the subject, and wherein if the level of non-LB species is higher than a pre-determined threshold level specific for the sample was obtained, the subject has a disease or disorder of the vagina.

38. A method of any one of embodiments 31-36, wherein the method is used for monitoring the treatment of a disease or disorder in the subject, and wherein if the level of non-LB species is higher than a pre-determined threshold level specific for the vagina, the treatment is ineffective and a new treatment is initiated in the subject.

39. A method of any one of embodiments 31-36, wherein the method is used for monitoring the treatment of a disease or disorder, and wherein if the level of non-LB species is lower than a pre-determined threshold level specific for the vagina, the treatment is effective and the prescribed course of treatment is completed in the subject.

40. A method of any one of embodiments 31-39, wherein the method further comprises determining the identity of non-LB species in the sample.

41. A method of embodiment 40, further comprising choosing a therapy based on the identity of non-LB species in the sample.

42. Use of any of the preceding exemplary embodiments in Set 1 or Set 2 to diagnose BV or to detect conversion.

43. A use of embodiment 42 wherein the diagnosis or detection occurs before clinical manifestation of symptoms.

44. A use of embodiments 42 or 43 wherein the assessed microbiome is a vaginal microbiome.

45. A use of any one of embodiments 42-44 wherein diagnosis or conversion is based upon a $\Delta Cq$ score of 3 or greater.

Exemplary Embodiments—Set 3

1. A method of any one of the preceding exemplary method embodiments in Set 1 or Set 2 further comprising calculating a $\Delta Cq$ score and if the $\Delta Cq$ is below 3, diagnosing the subject with BV; predicting the recurrence of BV in the subject; and/or directing continued treatment of the subject for BV.

2. A method of any one of the preceding exemplary method embodiments in Set 1 or Set 2 further comprising calculating a $\Delta Cq$ score and if the $\Delta Cq$ is 3 or above, determining that the subject is free from BV; predicting the non-recurrence of BV; and/or directing the cessation of treatment of the subject for BV.

3. A method of any one of the preceding exemplary method embodiments in Set 1 or Set 2 further comprising calculating a ΔCq score and performing a non-LB melt curve analysis to generate a combined score.

4. A method of embodiment 3 wherein a ΔCq score of 3 or above in combination with an absence of melt curves within a defined temperature threshold direct (i) a determination that the subject is free from BV; (ii) a prediction of non-recurrence of BV; and/or (iii) direction of the cessation of treatment of the subject for BV.

5. A method of embodiment 3 wherein a ΔCq score of below 3 or the presence of melt curves within a defined temperature threshold direct (i) diagnosis of the subject with BV; (ii) prediction of the recurrence of BV in the subject; and/or (iii) direction of continued treatment of the subject for BV.

6. A method of embodiments 4 or 5 wherein the defined temperature threshold is ±10° C. from the Tm of LB.

7. A method of embodiments 4 or 5 wherein the defined temperature threshold is ±5° C. from the Tm of LB.

8. A method of embodiments 4 or 5 wherein the defined temperature threshold is ±2.5° C. from the Tm of LB.

9. A kit of any one of the preceding exemplary kit embodiments in Set 1 or Set 2 further comprising instructions to calculate a ΔCq score and if the ΔCq is below 3, diagnosing the subject with BV; predicting the recurrence of BV in the subject; and/or directing continued treatment of the subject for BV.

10. A kit of any one of the preceding exemplary kit embodiments in Set 1 or Set 2 further comprising instructions to calculate a ΔCq score and if the ΔCq is 3 or above, determining that the subject is free from BV; predicting the non-recurrence of BV; and/or directing the cessation of treatment of the subject for BV.

11. A kit of any one of the preceding exemplary kit embodiments in Set 1 or Set 2 further comprising instructions to calculate a ΔCq score and instructions to perform a non-LB melt curve analysis to generate a combined score.

12. A kit of embodiment 11 wherein a ΔCq score of 3 or above in combination with an absence of melt curves within a defined temperature threshold direct (i) a determination that the subject is free from BV; (ii) a prediction of non-recurrence of BV; and/or (iii) direction of the cessation of treatment of the subject for BV.

13. A kit according of 11 wherein a ΔCq score of below 3 or the presence of melt curves within a defined temperature threshold direct (i) diagnosis of the subject with BV; (ii) prediction of the recurrence of BV in the subject; and/or (iii) direction of continued treatment of the subject for BV.

14. A kit of embodiments 12 or 13 wherein the defined temperature threshold is ±10° C. from the Tm of LB.

15. A kit of embodiments 12 or 13 wherein the defined temperature threshold is ±5° C. from the Tm of LB.

16. A kit of embodiments 12 or 13 wherein the defined temperature threshold is ±2.5° C. from the Tm of LB.

Potential treatments for BV include antibiotics such as, without limitation, metronidazole, clindamycin and tinidazole. Probiotics may also be useful. Methods and instructions in kits can direct treatment with one or more of these treatment options. For example, a diagnosis of BV may trigger a direction to prescribe metronidazole. If monitoring or efficacy of treatment predictions as described herein show the metronidazole treatment to be ineffective, the systems and methods can direct a change to a second antibiotic such as clindamycin or tinidazole. In another embodiment, a diagnosis of BV may trigger a direction to prescribe clindamycin. If monitoring or efficacy of treatment predictions as described herein show the clindamycin treatment to be ineffective, the systems and methods can direct a change to a second antibiotic such as metronidazole or tinidazole. In another embodiment, a diagnosis of BV may trigger a direction to prescribe tinidazole. If monitoring or efficacy of treatment predictions as described herein show the tinidazole treatment to be ineffective, the systems and methods can direct a change to a second antibiotic such as metronidazole or clindamycin.

EXAMPLES

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Example 1

Materials & Methods. Bacterial strains and culture. Reference bacterial species in this study are listed in FIG. 3. Species not from the ATCC were clinical isolates identified in the Detroit Medical Center Microbiology Laboratory, and in the inventors' laboratory by 16S rDNA sequencing. DNA was extracted from cells in their original LB agar plates, or in some cases after being transferred to Luria-Bertani, Brain-Heart Infusion, or Blood agar plates (Difco). Cells were stored suspended in 0.5 ml of 15% glycerol-BHI at −80° C.

DNA extraction. Bacteria were lysed from vaginal lavages by adding sodium hydroxide and sodium dodecyl sulfate to final concentrations of 133 mM and 10% respectively, followed by vigorous reciprocal shaking at room temperature for 30 m. This lysate was then extracted with phenol:chloroform:isoamyl alcohol (25:24:1) then chloroform. The DNA was precipitated with an equal volume of 100% isopropanol, washed once with 70% isopropanol, and dissolved in 100 μl TE (10 mM Tris pH 8, 1 mM EDTA). DNA was stored at −20° C. until further use. Control experiments indicated that this method extracted DNA efficiently (detection of at least 40 cells, range 1-40 cells) from Gram positive, Gram negative and acid-fast bacteria, using both fluorescent DNA and PCR-based assays. DNA was amplified from extracts of reference bacterial species as single colonies, using QuickExtract™ Plant DNA 144 Extraction Solution (Epicentre, Madison, Wis.), modified by heating at 65° C. for 30 m, 95° C. for 1 m.

PCR primers, blockers, and amplification. Standard PCR was performed on RoboCycler Gradient 96 (Stratagene). Real-time PCR was performed using Cepheid SmartCycler or LightCycler 480 II (Roche Applied Sciences) thermal cyclers. The reaction utilized individually optimized amounts of each primer, 250 μM dNTPs (Invitrogen), 20 mM Tris pH 8.3, 3 mM MgCl2, 50 mM KCl, and Taq DNA polymerase, 5 units from either GeneChoice or New England Biolabs, 2.5 units GenScript Green Taq, or 1 unit of glycerol-free Taq DNA polymerase from APEX (Genesee Scientific) per 100 μl reaction volume, including either 0.073×SYBR Green I Nucleic Acid Stain (FMC Bio Products) or 0.25 μl of 15 μM SYTO9 (Invitrogen) for qPCR reactions.

Primers (Tables 1 and 2) were designed using BioEdit software (Tom Hall author, Ibis Biosciences) and the Ribosomal Database Project II, Releases 9 and 10 (RDPII, Michigan State University, East Lansing, Mich.). Candidate sequences were identified by inspection of selected aligned sequences and verified for inclusiveness and specificity using RDPII Probe Match, and for compatibility and lack of internal base pairing using Operon® tools (Operon Biotechnologies, Inc., Huntsville, Ala.). PB primer sequences were chosen to include as many species as possible in the target phylogenetic branch while excluding or minimizing non-targets. Programs for each primer were optimized for annealing temperature and extension times on pure templates (genomic DNA or sequenced lavage amplicon) from one or several species and tested for detection of template from DNA equivalent to at least 1-10 cells (exceptions noted in Tables 3A-3D). Primer specificity was then validated using reference species (listed in FIG. 3) and ultimately by sequencing of the amplicons generated from vaginal samples. Negative controls included mock samples processed at the same time as real samples, and reactions with no added template. Performance of the broad-spectrum primers was compared to published sequences and found to be as good to superior in inclusiveness or sensitivity (Table 1A). The broad spectrum primers are provided in Table 1B.

Additional primers useful for amplifying LB and non-LB species in vaginal samples are listed in Table 2 and elsewhere herein. Non-standard or degenerate bases disclosed herein include: A+C+G=V; A+C+G+T (N-Wobble)=N; A+T+G=D; T+C+G=B; A+T+C=H; A+T=W; C+G=S; T+G=K; A+C=M; C+T=Y; A+G=R; A-Phosphorothioate=F; C-Phosphorothioate=O; G-Phosphorothioate=E; T-Phosphorothioate=Z.

Lavage DNA was tested for the presence of inhibitors assaying for a shift in Cp values of a spiked DNA control. The spike DNA was amplified from a cloned 542 bp fragment of a modified firefly (*Photinus pyralis*) luciferase gene from pGEM-luc vector (Promega), amplified with pUC universal (5'-CCCAGTCACGACGTTGTAAAACG (SEQ ID NO:17)) and reverse (5'-AGCGGATAACAATTTCACACAGG (SEQ ID NO:18)) primers with the cycling parameters 1×1 m @ 95° C.; 40× (30 s 30 s 30 s @ 94° C. 45° C. 72° C.); and 1×5 m @ 72° C. An aliquot of a $10^{-6}$ dilution was added to each sample for qPCR using luciferase-specific primers LucF3 (5'-GCTTACTGGGAC-GAAGACGAA, SEQ ID N0:19) and LucR3 (5'-GCGGTT-GTTACTTGACTGGC, SEQ ID N0:20), cycling parameters 1×1 m @ 95° C.; 40× (30 s 30 s 30 s @ 94° C. 64° C. 72° C.); 1×5 m @ 72° C. The undiluted lysed lavage genomic DNA (gDNA) showed negligible Cp shifts 190 (−0.08 and +0.14, <1 standard deviation from the mean) compared to spike alone (Cp=17.68+/−0.17 over 14 reactions), indicating that no inhibitors in the sample influenced the efficiency of the qPCR reactions. Reproducibility of the qPCR reactions was high; among 44 duplicate reactions, the average Cp range was 0.35 with a standard deviation of 0.25. LB blocking oligomers (LB-blockers) were designed with the criteria that they partially overlap binding sites for broad-spectrum BU4F+/BU6R+ primer combination (Table 1), and that their melting temperatures (Tm) were at least 68° C., which are higher than that of BU4F+/BU6R+. First generation blockers used phosphorothionucleotides on both ends to prevent digestion by exonuclease, and mismatched bases at the 3' ends were used to prevent their extension by polymerase. Second generation blockers did not use modified nucleotides, but retained the mismatches and added a 3' phosphate to block extension.

Amplicon cloning. Broad-spectrum PCR targets were amplified for varying cycle numbers, typically Cp plus 1 or 2 cycles to achieve a "just visible" product on an agarose ethidium-bromide gel. Amplicons derived from PB primers were sequenced directly with the rationale that any species present at 5-10× others amplified by the same PB primer would generate a single, readable sequence; amplicons from PB primers that were unreadable as uncloned amplicons were cloned after nested PCR. They were amplified to maximum fluorescence or maximum cycles for that primer. Products were cleaned by ultrafiltration with the Montage PCR kit UFC7PCR50 (Millipore) or QIAquick PCR purification kit (QIAGEN). One to three microliters of the 20 µl purified product was ligated into pGEM-T Easy vector using the pGEM-T Easy Ligation Kit (Promega) according to the manufacturer's specifications. The ligation reaction was carried out for from 4 hours to overnight at 4° C. Forty microliters of *E. coli* cells (strain XL1-Blue, Stratagene) were electroporated using a BioRad GenePulser and Pulse Controller (set at 2.5 kV, 25 µFD capacitance, and 200 ohms resistance) with 1 µl of the ligation, allowed to recover in LB broth 1 h at 37° C., then plated onto LB agar plus 100 µg/ml ampicillin with 0.1 mM IPTG and 20 µg/ml X-gal and grown overnight at 37° C. White colonies and a few blue control colonies were picked from the plates into 100 µl of 15% glycerol or TE, incubated at 94° C. for 5 m; 2 µl of this was amplified in 8 µl of reaction buffer as described, using primers that flank the cloning site in the vector (pUC-F CCCAGTCACGACGTTGTAAAACG (SEQ ID NO:88), pUC-R AGCGGATAACAATTTCACACAGG (SEQ ID NO:89); 95° C. (1 m), [95° C. (30 s), 45° C. (30 s), 72° C. (30 s)] for 40 cycles, 72° C. (5 m). Extension times for cloned amplicons from PB primers were adjusted as appropriate for each amplicon size according to Tables 3A-3D. An aliquot of each amplicon was tested by agarose gel electrophoresis.

Sequencing and analysis. Full length amplicons (5 µl) were enzymatically cleaned using a 5 µl solution of 0.1 units of NTPhos thermolabile phosphatase and 1 unit of Exonuclease I (Epicentre Biotechnologies), in 20 mM Tris pH 8.3, 50 mM KCl and 10 mM MgCl2 (1×PCR reaction buffer, Invitrogen), incubated at 37° C. for 15 m, then inactivated at 80° C. for 15 m, and used for sequencing. Mini-libraries were constructed from amplicons with co-dominant species (which generate mixed template reads when uncloned); 17 mini-libraries each averaging 11 sequences were sequenced. Enzymatically cleaned amplicons were sequenced with the same primers used for amplification, or T7 for cloned amplicons (Functional Biosciences, Inc.). Sequences were uploaded to Ribosomal Database Project II using the Pipeline function in MyRDP for trimming, quality scoring, alignment, and identification. Only base calls with PHRED quality scores (Q) above 20 were considered. A small number of high quality sequences were rejected by the website as non-ribosomal and were not considered further in this analysis. Aligned sequences, their closest hits via SeqMatch, and manually selected reference species, were downloaded from myRDP, manually trimmed to common 5' and 3' ends, and analyzed with Molecular Evolutionary Genetics Analysis (MEGA4 and MEGA5) software. From this, trees were constructed using the bootstrapped Neighbor-Joining method or the Maximum Composite Likelihood method, and used for species identification.

Calculation of titers and percent compositions. Cp values from reactions in LightCycler 480 II Real-Time PCR System (Roche Applied Science) were converted to molecules by comparison to Cp values of a standard curve from the same run derived from four to eight 10-fold serial dilutions of an amplicon quantified using the Quant-iT assay (Invitrogen). Molecules per µl were converted to cells per 5 ml lavage, assuming an average of five ribosomal genes per cell and proportioned to the ratio of the volume of the lavage used in the DNA prep and its final volume.

If the titer of the sample was below the limit of detection for the PB assay, nested PCR on a 24-cycle amplicon from a longer broad-spectrum 16S amplicon was performed (Tables 3A-3D). If the nested PCR was negative, the titer of the original sample was assumed to be 0; if the nested PCR was positive, the titer was reported as below the concentration of most dilute but still positive sample in each specific run. Amplicons were sequenced to verify that targeted species were amplified. Mixed amplicons were cloned into pGEM-T easy (Promega) and approximately 10 of the resultant clones sequenced. Percentages were calculated by dividing the titer from each PB by the sum of the titers from all the PB primers.

Compositions determined by 16S-C&S were simply tallies of sequences in each taxa, defined here as those with >97% identity. These tallies were adjusted in libraries from LB-blocked PCR with a correction factor. To determine this factor, the titers of *Gardnerella* and LB were independently determined with and without blocking by PB-qPCR. Their ratio in the unblocked sample ($7\times10^{-6}$) was increased in the blocked sample to 0.09, indicating an enrichment of $0.09/7\times10^{-6}=12,600$. To allow for better comparison of qPCR to 16S-C&S results, percent composition was converted to titers by multiplying the fraction of the broad spectrum sequences in the targeted taxonomic group by the total number of bacteria in the sample as determined by summed titers of all PB-qPCR targets. This sum is more useful for total bacterial load than titers calculated with broad-281 spectrum primers, although the two values generally agree within a two-fold margin.

For Tables 3A-3D, titers were determined by qPCR using standard curves and converted to approximate cells/sample as described herein. Primers BU4&BU6 were used alone for the 16S-C&S but the extended set (Table 1) was used for qPCR. Species were identified by Sanger sequencing of either uncloned amplicons, in cases where a single species was dominant for the target group, or by sequencing small numbers of *E. coli* clones derived from the amplicons if mixed. In silico performance was determined using the RDP website; Target hits is the number of database entries of "good" quality >1200 bp within the target grouping; Total hits is the total number of these hits in the RDP database; Specificity=target/total hits; Total target number=number of RDP entries in the target group; Target coverage=target hits/target number. Notes: uc=uncultured; n.d.=none detected; n.a.=not applicable; †=no subuniversal primer; *=detected by nested PCR only, reporting limit of detection; [ ]=identity; ~=novel species, closest hit listed. The Lachnospiraceae target does not include the following genera: Dorea, Blautia, Cellulosilyticum, Marvinbryantia, Clostridium XIVb; underlined titers=detected by nested PCR only, reporting here the limit of detection of the initial qPCR reaction; =All programs initiated with 95° C. 1 min and ended with 72° C. 5 min; *=excludes ~⅓ of *Clostridium* XI; ****performance not determined, showing forward primer only. Cross-family Clostridia primers complement families across the order, including: Bacillaceae 1, Bacillaceae 2, Paenibacillaceae 1, Planococcaceae, Staphylococcaceae, Clostridiaceae 1, Erysipelotrichaceae, Clostridiales Incertae Sedis XII, Clostridiales Incertae Sedis XIII, Lachnospiraceae, Peptostreptococcaceae, Veillonellaceae. Species identified from clones in the Lachnospiraceae group were from an older, slightly less inclusive primer set: LachnoL3 (GTAAAGCTCTATCA-GMAGGGAAGA (SEQ ID NO: 90)) and LachnoR1229 (CMCTTTGTTTACGCCATTGT (SEQ ID NO: 91)).

Figure 2:
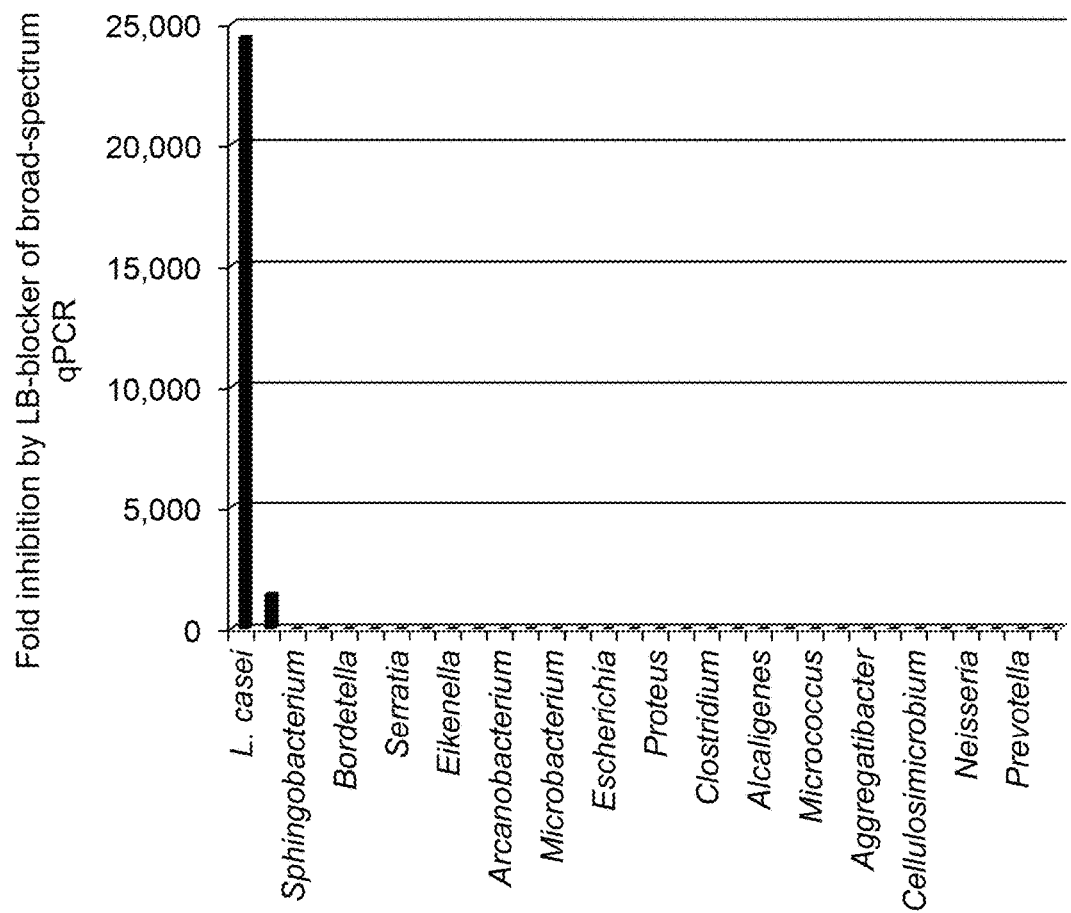
FIG. 2. Specific interference of amplification of *Lactobacillus* (LB) with LB blockers. The inclusion of LB-blockers increases Cp value on LB genomic DNA by at least 16 cycles, without changing Cp values of other species. Cp values were determined during amplification with broad-spectrum primers plus-or-minus LBB3p and LBB44. *Staphylococcus* and *Streptococcus* were slightly inhibited. Fold inhibition was calculated as $E^{\Delta Cp}$ where E (efficiency from a standard curve) was 1.85. $\Delta Cp=Cp$ value with LB-blockers minus Cp without blocker.

Results. Blocking amplification of dominant Lactobacilli during broad-spectrum PCR. To detect species present at three or more orders of magnitude lower than dominant LB in healthy or PT BV patients, oligomers were optimized to block amplification of LB. LB-blockers specifically prevented amplification of pure target LB (genus) template with broad spectrum primers, without affecting amplification of other species (FIG. 2) and without altering their quantification. Only related *Staphylococcus* and *Streptococcus* species showed slight inhibition, indicating that their quantification with this tool will be underestimated.

LB-blockers were also capable of inhibiting target amplification of a dominant LB subpopulation in a healthy vaginal lavage. In this test, the sample was amplified with broad-spectrum primers with and without LB-blocker, then assayed for the presence of LB amplicon with qPCR with nested LB-specific primers. LB amplicon was not generated if blocked, because the amplicon at a 1:1000 dilution was negative by nested qPCR with LB primers. In contrast, unblocked initial reactions generated product even when diluted one million-fold. The Cp value increased after blocking by 12 cycles; at its amplification efficiency of 1.85, this indicates that blocking decreased the effective titer by a factor of at least ~1.6 million ($1000\times1.85^{12}$).

Compositions of vaginal microbiota using blocked and unblocked 16S C&S. The LB-blocker approach was validated with a pair of vaginal lavages from a patient with BV. The first sample (BV) was taken during the acute symptomatic phase, positive for all Amsel criteria, with a Nugent score of 10. A second sample was taken in full remission after treatment with tinidazole, 500 mg twice a day for 10 days.

Figure 3:
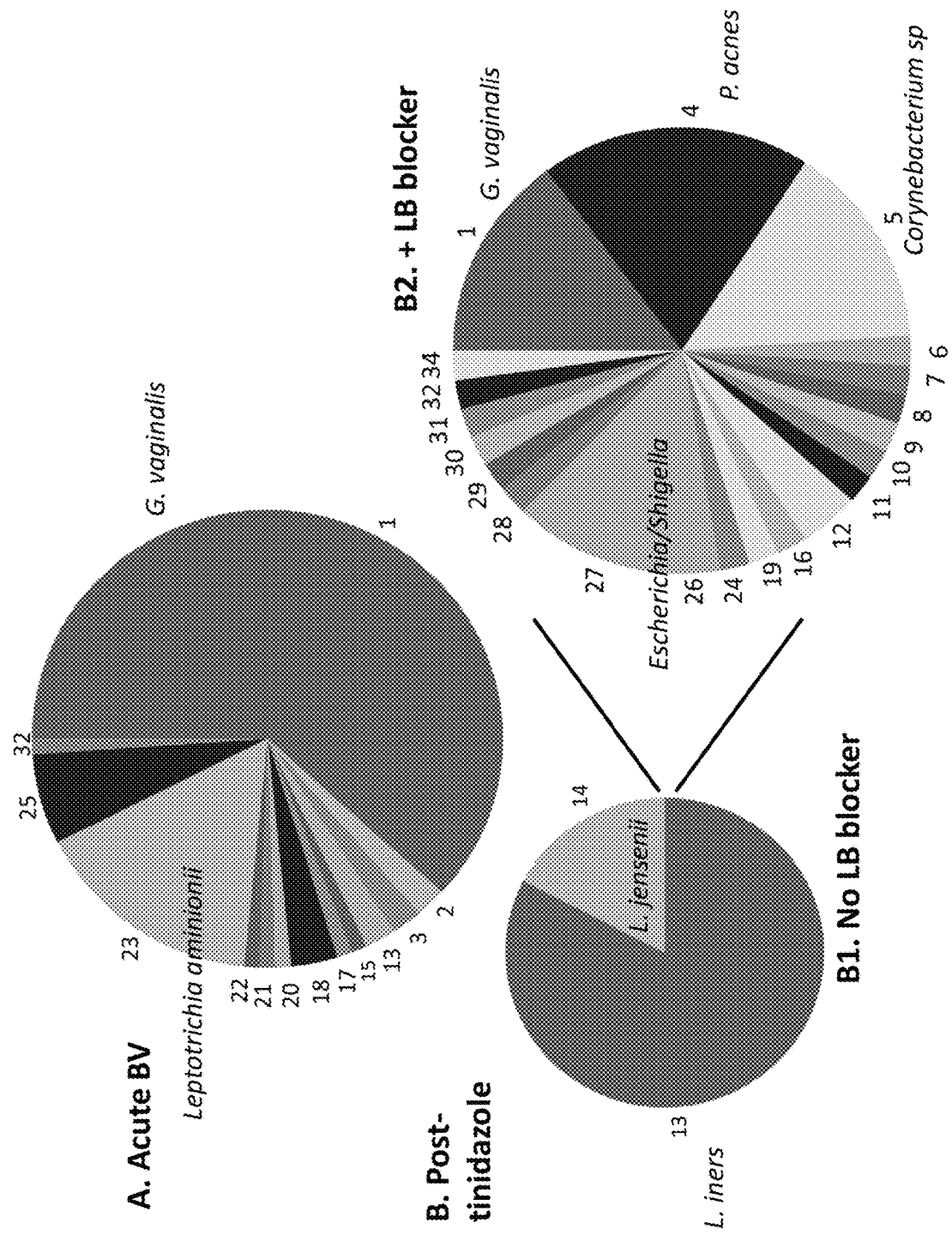
FIG. 3. Compositions of vaginal microbiota from a patient with acute bacterial vaginosis (BV) and after tinidazole, with and without LB-blocking. Amplicons from broad-spectrum primers were cloned and sequenced. The post-tinidazole sample was amplified with and without LB-blockers. B2 represents the non-LB, collectively 0.003% of isolates. Species or taxa were identified and tabulated. 1. *Gardnerella vaginalis* (A); 2. *Atopobium vaginae* (A); 3. *Eggerthella* sp, uc (A); 4. *Propionibacterium acnes* (A); 5. *Corynebacterium* sp, uc (A); 6. *Corynebacterium thomssenii* (A); 7. *Corynebacterium amycolatum* (A); 8. *Corynebacterium coyleae* (A); 9. *C. pyruviciproducens* (A); 10. *C. ureicelerivorans⁻* (A); 11. *Brevicacterium* sp (A); 12 *Actinomycetales* sp, uc (A); 13. *LB iners* (F); 14. *LB jensenii* (F); 15. *LB gasseri* (F); 16. LB sp⁻ (F); 17. *Aerococcus* sp, uc (F); 18. *Roseburia⁻* (F); 19. *Ruminococcus⁻* (F); 20. *Anaerococcus prevotii* (F); 21. *Peptoniphilus* sp (F); 22. *Dialister* sp, uc (F); 23. *Leptotrichia amnionii* (Fu); 24. *Bacteroides* sp, uc (B); 25. *Prevotella bivia* (B); 26. *Sphingomonas aerolata⁻* (B); 27. *Escherichia coli* (γ-P); 28. *Aggregatibacter* sp. (γ-P); 29. *Pseudomonas fluorescens* (γ-P); 30. *P. pseudoalcaligenes* (γ-P); 31. *Methylobacterium aminovorans* (α-P); 32. *Janthinobacterium lividum* (β-P); 34. *Arcobacter cryaerophilus* (ε-P). The phylum is abbreviated: A=Actinobacteria, F=Firmicutes, Fu=Fusobacteria, B=*Bacteroides*, and P's are the gamma-, beta-, and epsilon-proteobacteria. ∼=>3% divergent from indicated, nearest database hit.
Figure 6:
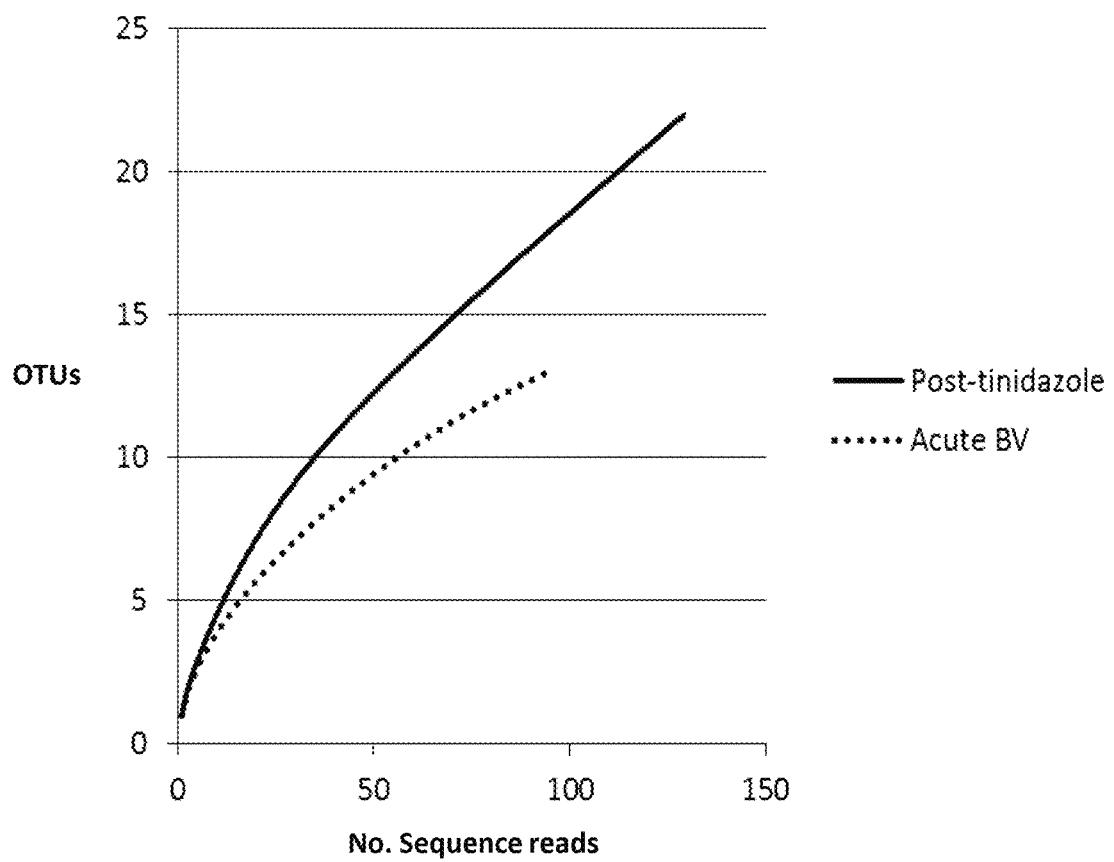
FIG. 6. Rarefaction curves of acute BV and post-tinidazole samples.
Figure 7:
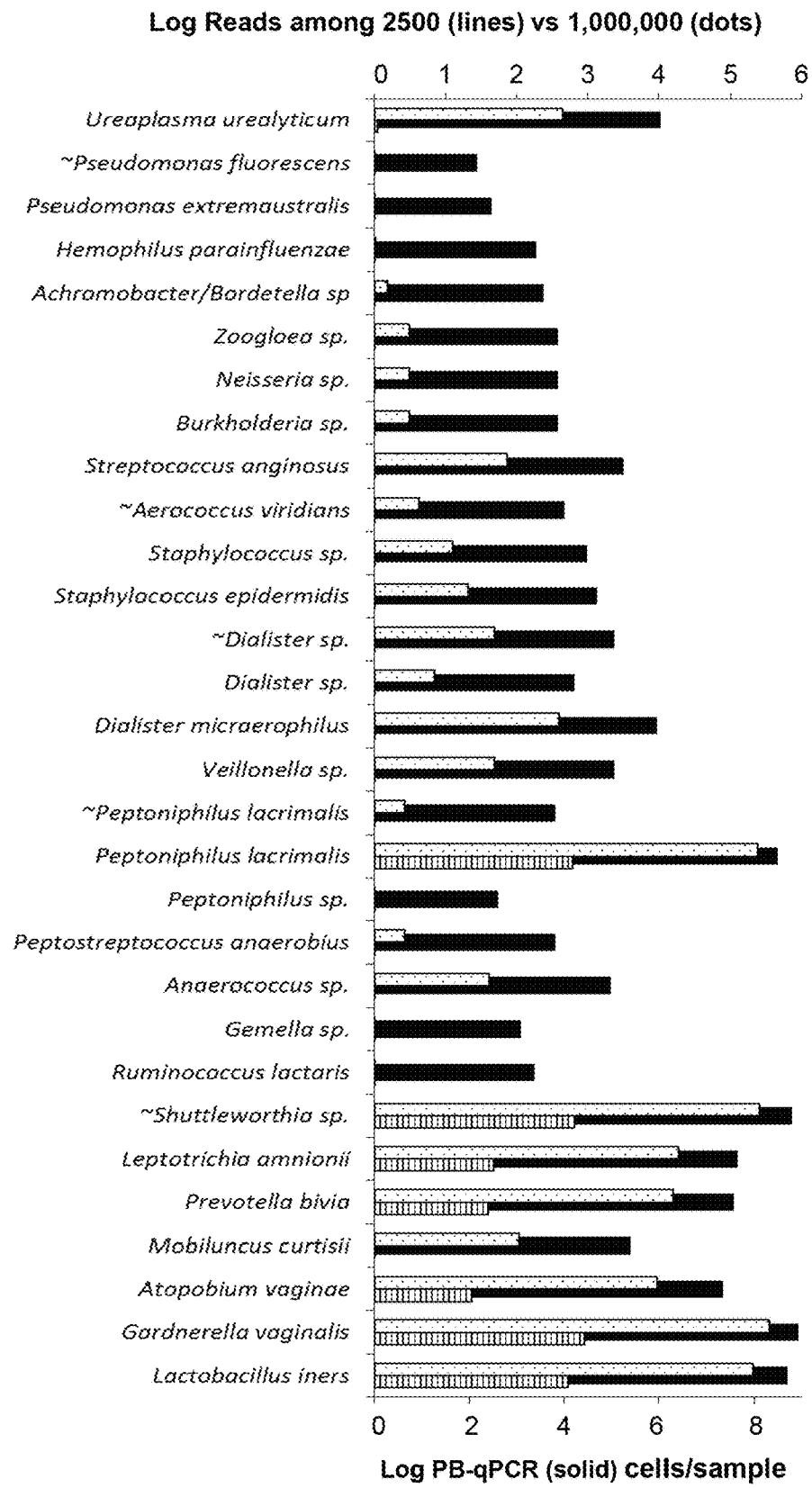
FIG. 7. Actual and projected diversity of the acute BV sample based on PB qPCR titers and sequencing FIG. 8. Actual and projected diversity of the post-tinidazole sample based on PB-qPCR titers and sequencing FIG. 9. Taxonomic diversity of vaginal samples. Numbers of operational taxonomic units (OTUs, sequences with >97% identity) were determined by PB qPCR+ (PB-qPCR for titers plus sequences of uncloned homogenous amplicons or small cloned libraries from heterogenous amplicons) and by LB-blocked sequencing. Summarized from FIGS. 7 and 8. MpNGS=multiplexed NGS run projected from 2500 hypothetical reads of the PB-qPCR+ profiles, or MpNGSb from the LB-blocked profile; NGS=single sample NGS projected from 10$^6$ reads of the PB-qPCR+ profiles or NGSb from the LB-blocked profile; AvgNGS=average of 152 BV or 90 healthy samples averaging of 1547 and 1742 reads per sample respectively.
Figure 8:
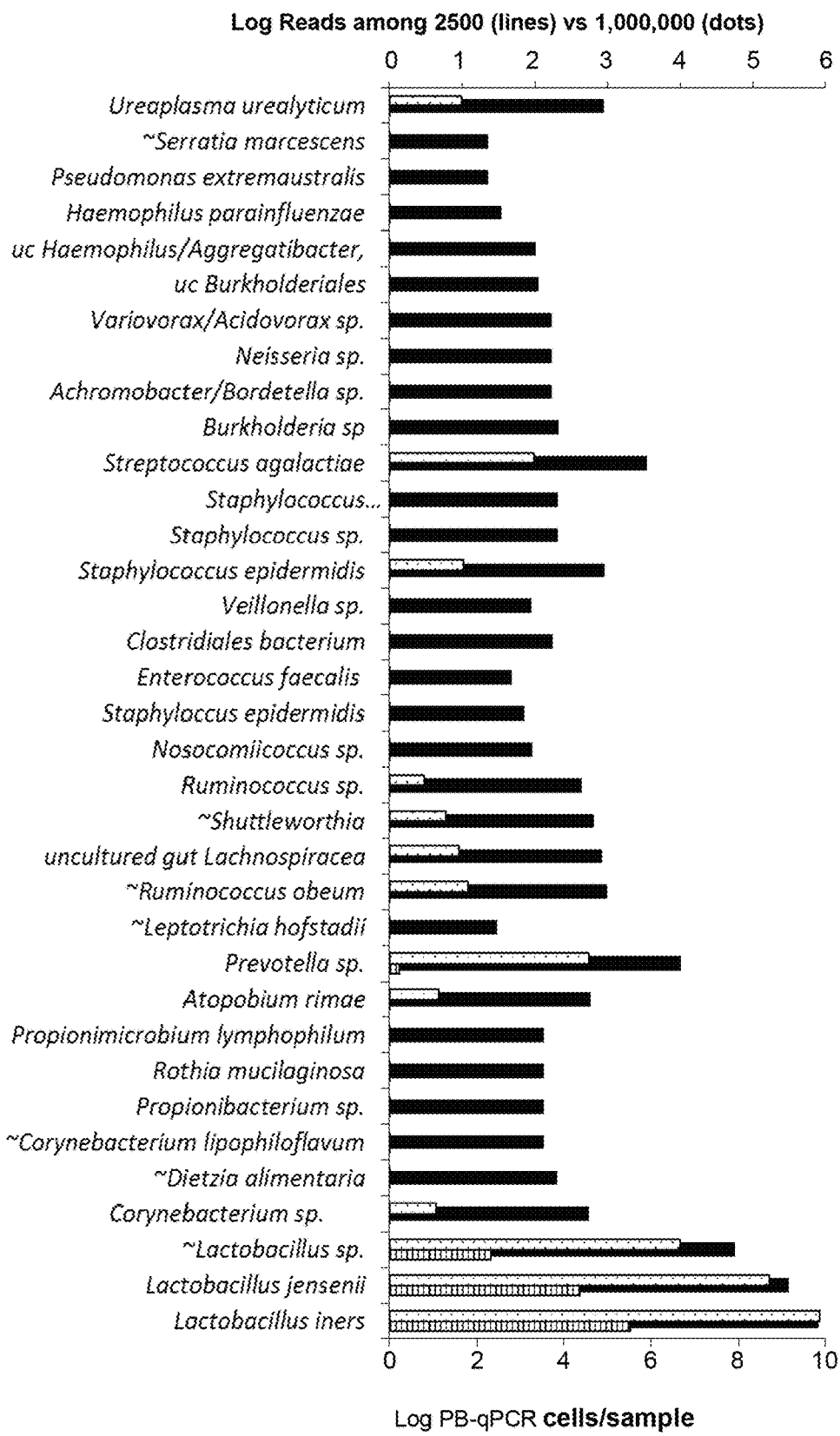
Figure 9:
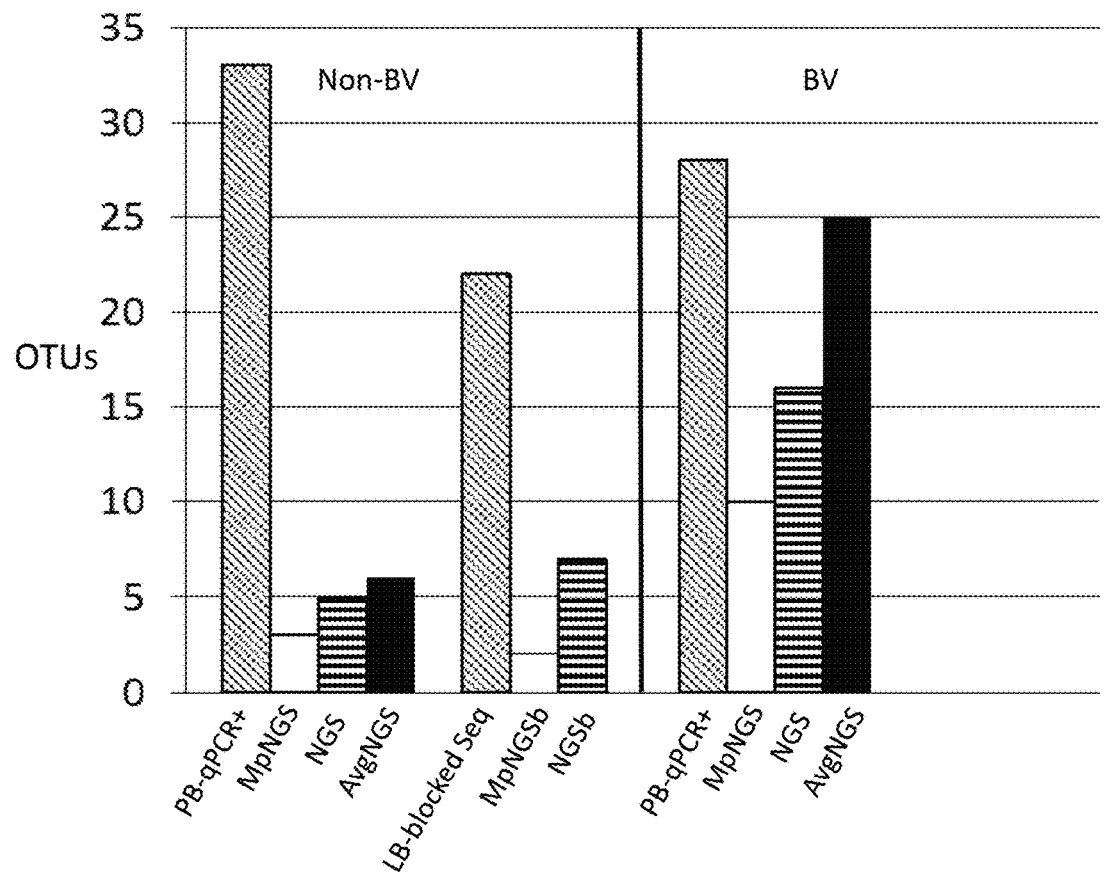

The acute BV sample showed an expected dominant population of *G. vaginalis*, both cultured and uncultured variants, comprising ~62% of the total (FIG. 3). The next most prevalent groups were Fusobacteria: dominantly *Leptotrichia amnionii* (16%) and *Bacteroides* (*Prevotella timonensis*, ~6%). Also present were Coriobacteriaceae (4%) including *Atopobium vaginae* and novel phylotypes related to *Eggerthella* spp. A heterogeneous collection of Clostridiales (5%) included novel species in the Lachnospiraceae family (BVAB1), mostly closely related to *Roseburia* (97% identity). Also in this family was *Anaerococcus prevotii* (1%) and *Peptoniphilis lacrimalis* (1%). Other Firmicutes included *L. iners* (2%), *L. gasseri* (1%), *Aerococcus* sp. (1%), and *Dialister* (1%). Notably, Mobiluncus, Mycoplasma, and Ureaplasma were not detected. Chao1 prediction of actual diversity was 19 OTUs compared to 13 observed, with a Good's coverage of 93.6% and Shannon index of 1.4 (Table 4). FIG. 3 illustrates the dramatic increase in species detection in the LB-blocked reaction, despite the small numbers of reads in this trial, relative to the unblocked sample. In the absence of LB-blocking, all reads were LB, either *L. iners* (83%) or *L. jensenii* (17%). In the presence of LB-blockers, 21 other species were detected, collectively representing only 0.003% of the total population. This included a variety of Actinobacteria, including *G. vaginalis*, *Propionibacterium acnes*, *Brevibacterium* sp., and *Corynebacterium* spp., including a novel species. A collection of Proteobacteria were detected, which included two novel species (>3% divergent), one related to *Ruminococcus* and another in the LB genus. Chao1 prediction of actual diversity in the blocked sequencing was 135 OTUs compared to 22 observed, with a Good's coverage of 88.4% and Shannon index of 1.7 (Table 4). In both samples, it was clear that the actual diversity exceeded what was detected with these limited numbers of cloned sequences, because many species were represented by only a single read, consistent with rarefaction curves (FIG. 6). Most of the isolates identified by sequence were well established species with high similarity indices to species in the database (98-99% identity). However, five novel species were detected that were more than 3% divergent from anything in the database.

Figure 4:
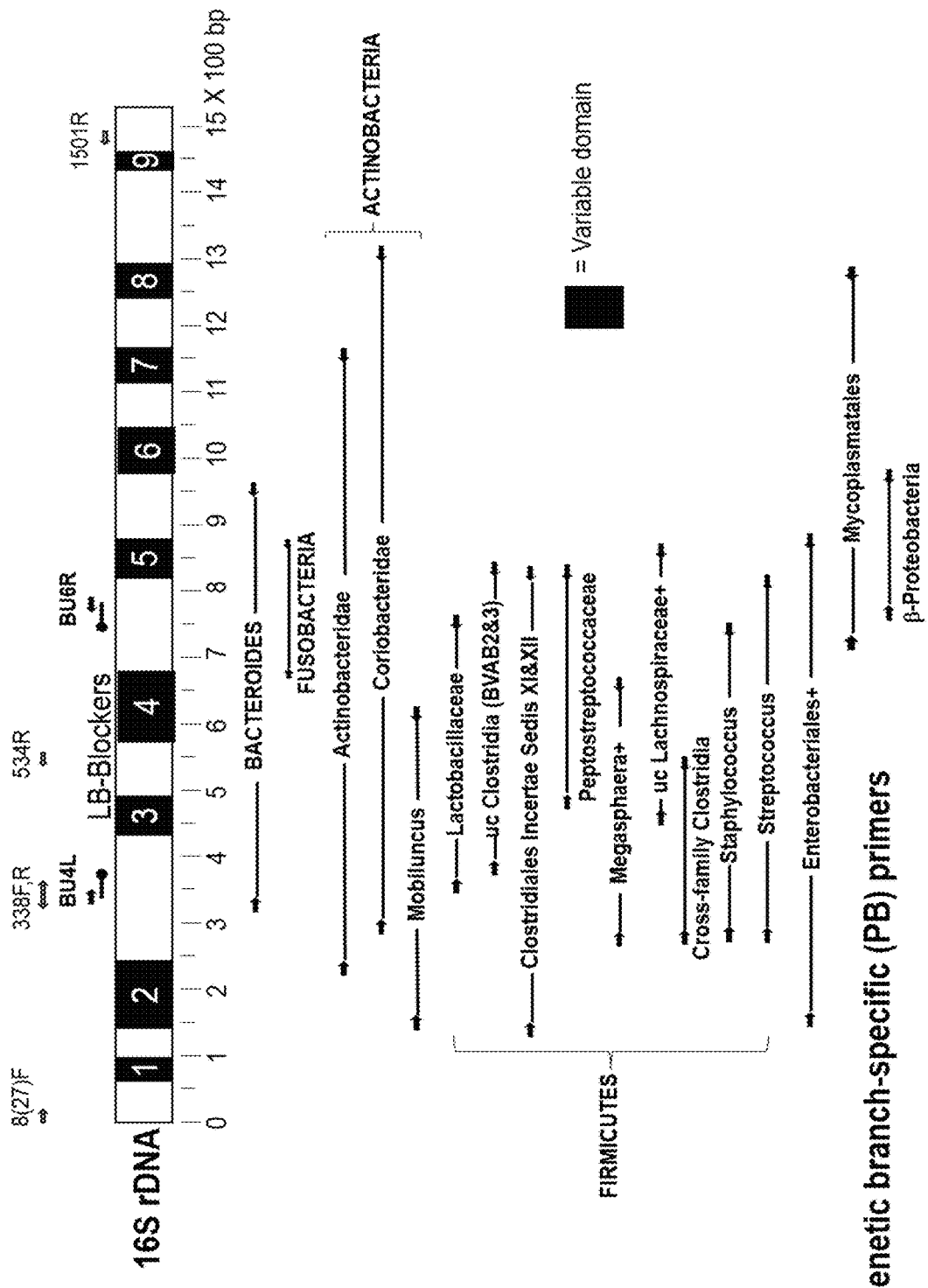
FIG. 4. Relative positions of broad-spectrum and primer-blocking (PB)-primers on 16S rDNA. The 16S-rDNA gene is depicted with its variable domains based on *E. coli*. Above this are positions of BU4 and BU6 used as broad-spectrum primers. In addition, other primers used for this purpose are positioned, including 27F-338R, 338F-806R, and 341F-534R. 338F/R and 341F partially overlap BU4; 806R partially overlaps BU6. The in silico performances of these are compared in Tables 3E. Below the 16S rDNA gene are the PB-primer positions. Specifics about these primers including their in silico performances and their cycling parameters are in Tables 3E. Primers overlapping with 27F and 1501R were used as 1$^{st}$ round primers in nested polymerase chain reaction (PCR) to detect some targets below the limit of detection. uc=uncultured, +=other related genera in the target as described in Tables 3A-3E.

PB-qPCR. Because compositions based on broad-spectrum primers have limitations, the complementary approach of using qPCR with 16 PB primers was employed. Positions of PB primers are depicted in FIG. 4 and are described in detail in Tables 3A-3D. Each PB primer targets its own phylogenetic branch ranging from whole phyla to family or genus and is far more inclusive than species-specific primers. To validate their use, known concentrations of amplicons of 15 vaginal bacterial species were mixed in proportions that resembled both acute BV and healthy vaginal samples. PB-qPCR of these mock samples showed that the observed titers agreed with the input, typically with an observed/input ratio of 0.6.

Figure 5:
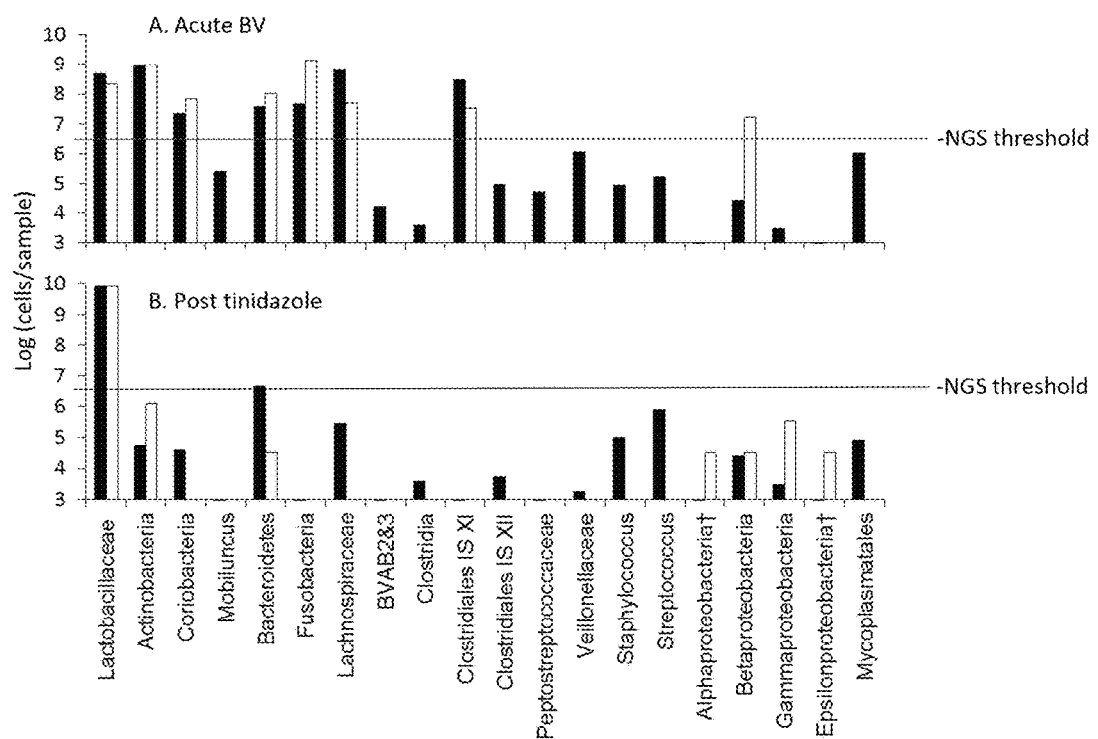
FIG. 5. Compositions of acute BV (FIG. 5A) versus post-tinidazole (FIG. 5B) samples by PB-qPCR versus 16S-C&S (culture and sensitivity). For 16S-C&S data, percent compositions (FIG. 3) were converted to titers to facilitate comparison to the qPCR data. †=No PB primer was designed. Species detected at titers below the "threshold" line would have been undetected or inaccurately counted in a 2500-read next-generation sequencing (NGS) project.

PB-qPCR generated typical compositions for both the acute BV and post-tinidazole samples (FIG. 5). The acute BV sample (FIG. 5A) is co-dominated by $G.$ $vaginalis$ (Actinobacteria), $L.$ $iners$, $P.$ $bivia$ ($Bacteroides$), novel Lachnospiracea, $A.$ $vaginae$ (Coriobacteria), $Peptoniphilis$ sp. (Clostridiales Incertae Sedis XI), $Dialister$ sp. (Veillonellaceae), and $L.$ $amnionii$ (Fusobacteria), all at titers in the $10^6$-$10^8$ cells/sample range. These titers are within an order of magnitude for most targets compared to results from 16S-C&S, for those targets not biased by low numbers of reads in the latter. PB-qPCR of the post-tinidazole sample (FIG. 5B) detected several targets that were beneath the level of detection of the 16S-C&S approach due to low numbers of reads. The post-tinidazole sample is dominated by $L.$ $iners$, but still has significant titers of $G.$ $vaginalis$ and other BV-associated anaerobes. Some of these were seen only by PB-qPCR, others only by LB-blocked 16S-C&S, again likely a consequence of low numbers of clones in sequencing. Overall, there was good agreement between the two methods. Overall bacterial loads in the two samples were about the same. The titer of $L.$ $iners$ was only approximately 20-fold lower in the acute.

The BV sample compared to post-tinidazole, whereas $G.$ $vaginalis$ was approximately $10^4$-fold higher. Other BV-associated anaerobes were present at $10^1$ to $10^8$-fold higher levels in the BV sample.

To verify that titers reported by each primer represented the target branch, amplicons generated by PB-qPCR were sequenced. In most cases, no cloning was needed, reflecting that one species represented >80% of amplified sequences. Some amplicons were cloned and sequenced, however, to resolve mixtures of co-dominant species and look for species variation before versus after treatment. Thirteen species differing by >3% from those in the database were detected, including species related to $Shuttleworthia$, $Ruminococcus$, $Peptoniphilis$, $Leptotrichia$, and $Pseudomonas$ (Tables 3A-3D).

Diversity comparisons. Projecting from the proportions of each species among the small libraries and the relative titers from PB-qPCR, the taxonomic diversity in the post tinidazole sample had 6-10 times the number of operational taxonomic units (OTUs) one would expect if the same population had been characterized by NGS at somewhere between 2500 and $10^6$ reads, and five times the actual diversity observed among 90 healthy patients (FIG. 6). The profile generated by sequencing the LB-blocked amplicon is 3-10 times more diverse than actual and projected NGS runs. The BV sample PB-qPCR sequencing profile shows about twice the diversity of the projected NGS runs. This approximates the average level seen among 152 BV patients by NGS. In silico comparison demonstrated that novel or atypical Clostridial species seen in this study had primer binding sites that had as many as 7 mismatches to the BVAB-1, -2, or -3 primers used in previous studies. Consistently, these species-specific BVAB1 primers failed to detect target in our samples. Furthermore, most of the variant species observed (Tables 3A-3D) have imperfect complementarity to primers specific for "expected" species in the target group and thus would either be missed or undervalued.

Example 2

Longitudinal Analysis of Vaginal Microbiome Dynamics in Women with Recurrent BV: Recognition of the Conversion Process. Recurrence is a key problem in BV. For example, one study found 58% of 121 women with BV, who were successfully treated with metronidazole, recurred within one year; 69% returned to abnormal vaginal profiles. It is not clear if vaginal species in varying proportions represent subgroups that impose varying risks of complications or of symptoms, and if they play a role in conversion of the healthy vaginal microbiome. A small study showed strong predictive value of prevalent Gram-positive cocci in pretreatment Gram stains of BV patients for rapid recurrence.

There are many published longitudinal studies, but most sampled at long intervals, often weeks or months. Although much valuable information can be gleaned from these studies, they cannot show rapid fluctuations that were demonstrated in studies that used daily vaginal swabs over at least a portion of the study interval. An under-appreciated consequence of single-sample studies, which are the norm, is that they capture glimpses of dynamic processes at unknown stages. However, none of these studies sampled with sufficient frequency or depth enough to capture sequential changes in the vaginal microbiota as BV recurs.

The present example describes detailed longitudinal microbial profiles of five women with histories of recurrent BV, using qPCR methods described herein. Two of the five patients recurred with acute BV, slowly in one case, more rapidly in the other case, following metronidazole therapy. Two did not recur during the study, and one showed a poor response to therapy and presented with an intermediate Nugent score. Data show high levels of variation of target species during recurrence, and differences in profiles between acute BV samples of the five patients, which change in sequential episodes. More importantly, data suggest that incomplete restoration of LB sp. after therapy predicts poor outcome, and that the microbiome can undergo a newly described event termed conversion, the decline in LB and rise of replacement species, days to weeks before symptomatic BV. Conversion can indicate the failure of a therapy and/or can predict risk of BV recurrence.

Materials and Methods. Patients. Five African American participants were followed at the Vaginitis Clinic at Wayne State University and had been treated for recurrent episodes symptomatic bouts of BV. Patients were enrolled after protocol explanation and written informed consent was obtained. The study was endorsed by the Human Investigational Review Board of Wayne State University. At the time of enrollment, patients were diagnosed with florid symptomatic acute BV, characterized by the presence of at least 3 of the 4 Amsel criteria (homogeneous vaginal discharge, pH elevated above 4.5, clue cells >20%, positive whiff test) and Nugent scores of at least 8.

Generally, patients were treated with a metronidazole, clindamycin, or tinidazole regimen and returned within three weeks with a clinical cure by Amsel criteria (zero criteria positive) and Nugent scores of 0, except Patient 5, who had an intermediate Nugent score of 4. At this immediate PT visit, patients were given Catch-All Sample Collection Swabs (Epicentre Biotechnologies, Madison, Wis.) and 15 mL conical tubes for vaginal specimen self-collection. Patients were seen at the Vaginitis Clinic and evaluated monthly at which time vaginal swabs were collected. Samples from a previously characterized group of recurrent BV patients, sampled before and after treatment, were also evaluated by Lb-qPCR. Reichman et al., (2009) Sexually transmitted diseases 36: 732-734.

More particularly, P1, a 39-year-old married African-American woman had been seen in the WSU Vaginitis Clinic on multiple occasions for recurrent bouts of bacterial vaginosis (RBV) over a 9-year period. In the two previous years, she presented with 4 florid episodes of BV in spite of receiving maintenance suppressive prophylactic therapy with vaginal metronidazole 500-750 mg twice weekly. The last two of these four episodes was characterized by molecular methods. She was enrolled as a longitudinal patient three months after discontinuing prophylactic vaginal metronidazole and after being asymptomatic in full clinical remission for seven months. At enrollment she presented with florid BV. She received daily metronidazole suppositories 750 mg and returned 10 days later in full remission. No additional antibacterial therapy was prescribed and self-obtained vaginal 35 swabs were collected over the next three months, during which time she remained asymptomatic, until returning on day 94 with recurrence of symptomatic BV. In the interim 90 days she was seen three times in follow up in the clinic and found to be in full remission, the last visit some three weeks prior to the documented recurrence. At all three follow up visits, her measured vaginal pH was within normal limits, no clue cells were detected and whiff tests were negative. Self-obtained swabs were suspended in 2 mL sterile saline, and kept refrigerated until being returned to the clinic on a weekly basis.

P2, a 26-year-old African American female similarly was enrolled with presentation with acute symptomatic BV. She received oral metronidazole 500 mg bid for 7 days and returned one week later asymptomatic. Thereafter she self-obtained vaginal swabs daily, but experienced Amsel and Nugent symptomatic recurrence 35 days after enrollment. She was culture-positive for *Candida albicans* at all 3 visits. This second episode of BV was treated with 500 mg metronidazole suppositories, 2 per day for 7 days, after which she recovered well off therapy, obtaining daily swabs until day 93. She had a prolonged menses, and resumed daily swabs on day 122 without symptoms until she reported symptoms at day 152, but did not return to the clinic for confirmation. P2 collected her self-swab in 2 mL lysis solution (10% SDS, 10 mM Tris, pH 8, and 10 mM EDTA) and stored her swabs at room temperature until returning to the clinic for her 1 month follow up appointment.

P3, a 35-year-old African American woman with a history of recurrent BV presented with florid signs of BV and Nugent score of 10. She was treated with 2% clindamycin for 7 days and returned three weeks later in full remission and a Nugent score of 0. No further therapy was advised and daily vaginal swabs recommended. She returned 6 weeks later without symptoms and still in full remission by Nugent and Amsel criteria. She was followed and seen monthly over the next 6 months and remained in clinical remission with regard to BV but had intermittent pruritus due to culture-confirmed *Candida parapsilosis* co-infection. P3 collected her self-swabs in 2 mL lysis solution. In all, 125 vaginal specimens were obtained, however the first 28 self-swabs were excluded from analysis due to problems during DNA extraction.

P4 was a 24-year-old African American woman with a history of recurrent bouts of BV. Married and a heavy smoker, she presented recurrence of BV, confirmed on physical examination, by the presence of all 4 Amsel criteria and Nugent score of 9. She was treated with tinidazole 500 mg bid for 7 days. She returned one week later after completing therapy, and was entirely asymptomatic with normal physical findings, pH 4.2, negative amine test and normal flora morphotypes. She agreed to collect daily vaginal swab samples to monitor microbiome changes. Swabs were obtained over 30 days in absence of symptoms. Patient 4 collected swabs in 2 mL sterile saline as described for Patient 1.

P5, a 32-year-old African-American woman presented with florid BV, fulfilling all four Amsel diagnostic criteria and a Nugent score of 10. She received 7 daily 500 mg metronidazole vaginal suppositories. She returned 21 days later asymptomatic in clinical remission; however, saline microscopy revealed mixed flora and her Nugent score was 4. She obtained 22 daily vaginal swabs and returned 56 days later for a second post-treatment visit complaining of itching and discharge. Although culture was positive for *C. albicans*, she fulfilled all four Amsel criteria and had a confirmed Nugent score of 4.

Sample processing, DNA extraction, and qPCR. Microbial gDNA was purified from swabs in 1-2 ml saline or lysis solution by a high SDS/alkaline lysis phenol extraction protocol as described previously in Lambert and resuspended in 200 □L TE (10 mM Tris, pH 8, 1 mM EDTA). The lysed bacterial gDNA is stable for over one month at room temperature in lysis solution buffer (data not shown) and this buffer prevents changes in titer due to possible stability issues with different strains of bacteria in saline. An aliquot of purified DNA was assayed by qPCR with 18 universal and phylogenetic branch-inclusive (PB) primers and PCR conditions as described previously in Lambert. Additional primers, targeting the *Enterococcus* genus and its cytolysin gene CylLL, are provided in SEQ ID NOs: 92 and 95 (*Enterococcus*), and 93 and 96 (cytolysin gene). Each PB-primer targets a branch of the phylogenetic tree, from whole phyla to family or genus, and is far more inclusive than species-specific primers. Relative LB composition of the vaginal microbiome was determined by dividing the Lactobacillaceae titer by the sum of all PB-primers and by using the disclosed LB-blocker approach. Briefly, the LB-blocker approach uses the difference between the quantitative cycles (Cq) of two parallel qPCR reactions with universal primers targeting the 16S rRNA gene, when one of the reactions is in the presence of LB spp.-specific blocking oligomers (LB-blockers) that have been chemically modified to prevent extension and that partially overlap the universal primer binding site, effectively rendering the LB DNA "invisible" to the universal PCR, even when LB gDNA is present at great excess compared to non-LB gDNA, as is common in healthy and PT samples. PB-primers amplicons were selectively sequenced to confirm they were correctly targeted and to identify the dominant species. These were "cleaned" enzymatically as described in Lambert, and Sanger sequenced at Functional Biosciences (Madison, Wis.). Sequences were uploaded to Ribosomal Database Project II using its Pipeline function; species were identified based on phylogenetic trees constructed in Molecular Evolutionary Genetics Analysis (MEGA5) software.

Calculations. Cq values from qPCR reactions were converted to molecules per reaction by comparing sample Cq values to a standard curve from the same run of Cq values derived from dilutions of an amplicon of known target of known concentration. Molecules per reaction were converted to cells per swab, assuming an average of 5 ribosomal genes per cell and proportioned to the ratio of the volume of the sample used in the DNA prep and the amount of sample used in the qPCR reaction. Delta Cq ($\Delta$Cq) values of LB-blocked reaction pairs were calculated as Cq (blocked sample)–Cq (unblocked sample). Differences between patient groups were compared using the t test in (GraphPad software).

Figure 10:
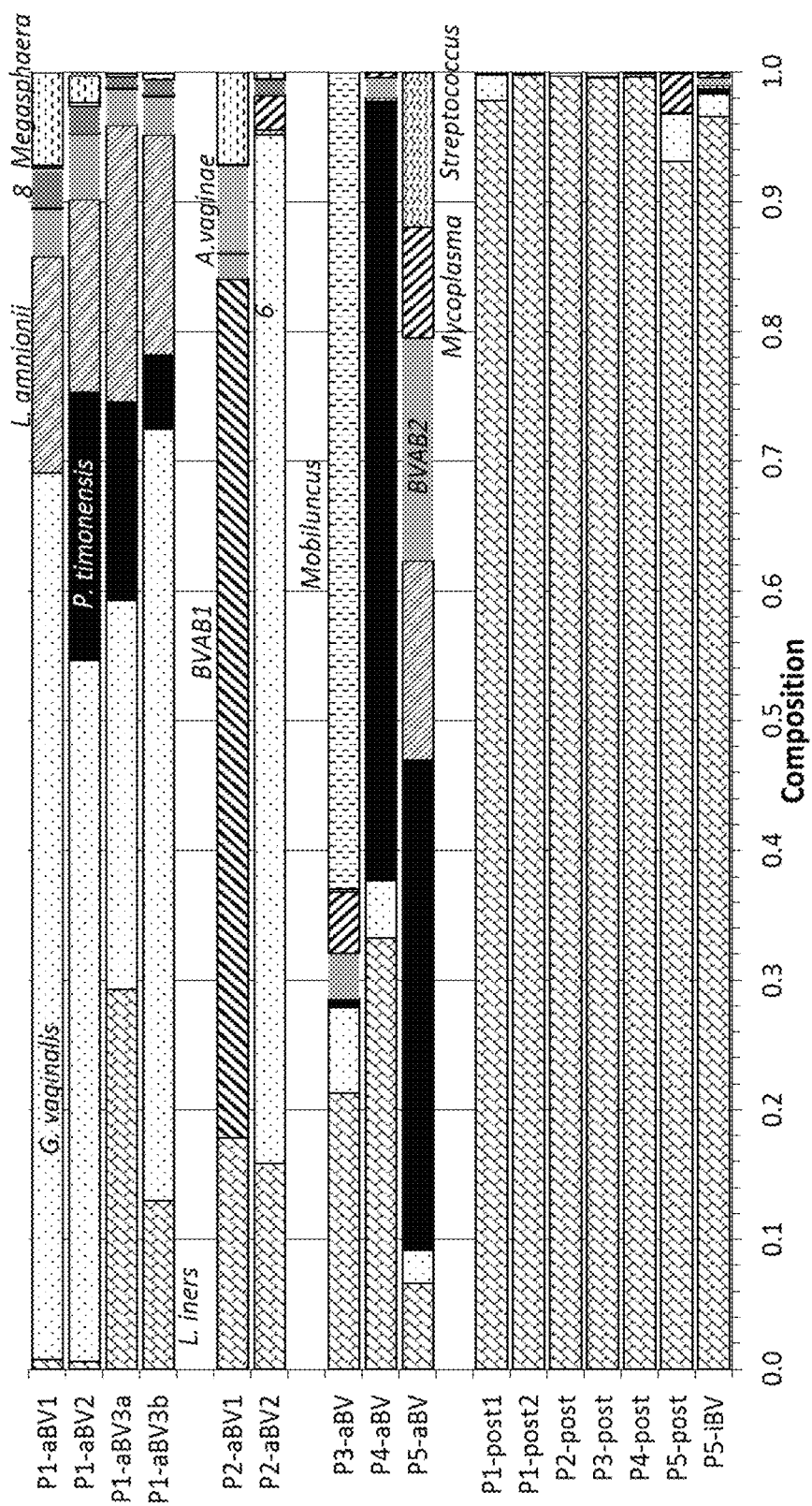
FIG. 10. PB-qPCR generated microbial profiles of acute and PT vaginal swabs of patients with histories of recurrent BV. Primers targeting the groups listed in the legend were used to determine Cq values; these and the conversions to relative titers were performed as described in Lambert et al. (2013) Appl Environ Microbiol 79: 4181-4185 (Lambert). Patient 1 (P1) was sampled at 3 separate acute BV (aBV) episodes; 3a and 3b are samples of the 3rd episode taken 5 days apart. P1 and P2 recurred during the study; P3 and P4 did not. P5 responded poorly and was ultimately diagnosed with BV at an intermediate Nugent score, 4 (P5-iBV). uc=uncultured.

Results. Overview of vaginal profiles of 5 patients (P1 to P5) with acute BV and after treatment. FIG. 10 illustrates the profiles of 5 patients with histories of recurrent BV at enrollment with BV and after treatment. Samples were analyzed from between one and three acute BV (aBV) episodes from each patient, as well as post treatment 7 to 21 days after the first diagnosis. Results are phrased here as PB-primer target (species by sequence). All PT samples were restored to dominance by Lactobacillaceae; predominantly *L. iners* or transiently *L. jensenii*; some samples were co-dominant for these as indicated by sequence polymorphisms. Acute BV samples fell into two groups: P1 and P2 (recurring patients) were dominantly Actinobacteridae (*G. vaginalis*); in contrast non-recurring patients P3 and P4, nor for P5, who responded poorly to therapy, were dominated by phyla other than Actinobacteridae. Sequential BV profiles from the same patient had differences, but were more similar to each other than to BV profiles of the other patients. BV samples were positive for 76-100% of the PB primers (ranging from 6-17 tests among individual samples) at subdominant or low levels. PT samples were still positive for 67-94% of the PB-primer targets, typically at much lower levels than the BV samples.

Patient 1 (P1) is characterized as a slowly recurring BV patient, who had 3 acute BV (aBV) episodes over 371 days (FIG. 10). At her first episode (P1-aBV1), she presented with acute BV, dominated by Actinobacteridae (*G. vaginalis*), but also having diverse species including sub-dominant (2-14%) Fusobacteria (*Sneathia sanguinegens*), Megasphaera/Dialister/Veillonella (*Megasphaera genomosp.* type 1), uc Clostridiales-BVAB2/3 (BVAB2), and Coriobacteridae (*Atopobium vaginae*), and 11 other groups at lower titers. Her profile was very similar at her second BV episode, most notably different only in her increased proportion of Bacteroidaceae/Prevotellaceae (*Prevotella timonensis*). Her third BV episode (divided here into the clinical confirmed episode, aBV3b, and her self-swab 5 days earlier, aBV3a), differed in having higher proportions of Lactobacillaceae (primarily *L. iners*) and Bacteroidaceae/Prevotellaceae (*P. timonensis*), and reduced levels of Megasphaera (*Megasphaera genomosp.* type 1). Comparing the P1-aBV3a to P1-aBV3b, *G. vaginalis* increased further at the expense of *L. iners*, and Lachnospiraceae (BVAB1) increased ~500 fold.

After both first and second BV episodes (P1-post1 and -post2), she responded well to high dose vaginal metronidazole treatments, becoming Amsel negative and having Nugent scores of 0. Consistently, both samples were >97% Lactobacillaceae (primarily *L. iners*). Actinobacteridae (*G. vaginalis*) was incompletely eradicated in P1-post1 at 2%, but was reduced by another ~100-fold in P1-post2. The level of reduction of *G. vaginalis* in this slowly recurring patient is similar to levels seen in non-recurring patients P3 and P4.

Patient 2 (P2) is characterized as a rapidly recurring BV patient. The first PT responses of P2 after successful oral metronidazole treatment resulted in an Amsel negative status and Nugent score of 0 (FIG. 1, P2-post1). Lactobacillaceae (*L. iners*) rose to similar levels of dominance compared to P1, Actinobacteridae (*G. vaginalis*) fell to <0.5%, and 6-8 other targets were seen at under 0.1%. After recurrence at day 35, similar response resulted from her second treatment, 2×500 mg metronidazole suppositories daily for 7 days, but in this case her recurrence occurred more slowly than the first, approximately 117 days PT based on self-reporting, since she did not revisit the clinic.

Patient 3 (P3), in contrast to P1 and P2, did not recur during the 172 days after enrollment. She was successfully treated with clindamycin to progress from Amsel positive and Nugent 10 to Amsel negative and Nugent 0. Her acute BV sample (FIG. 10, P3-aBV), was notably different from P1 and P2 in that her Actinobacteridae (*G. vaginalis*) component was ~10 fold lower, and her Mobiluncus component (*M. mulieris*) was >20 fold higher. After treatment (FIG. 10, P3-post), Lactobacillaceae (*L. iners*) rose to extreme dominance as expected, and Actinobacteridae (*G. vaginalis*) decreased 10-100 fold lower than P1 or P2, and except for Mobiluncus at 0.4%, all other targets were below 0.01%.

Patient 4 (P4) was similar to P3 in that she did not recur, but was only followed for a month before being dropped from the study due to pregnancy. However, at enrollment with acute BV, her initial sample P4-aBV1 was atypical, characterized by low Lactobacillaceae (*L. iners*) and low Actinobacteridae (*G. vaginalis*), as seen in non-recurring P3, but high levels of and Mycoplasmatales (mixed *Mycoplasma* spp.). She responded well to tinidazole treatment, with high dominance by *L. iners*, and the 7 non-LB targets that were detected were under 0.1%.

Patient 5 (P5) recurred in two and a half months, but only to an intermediate level, Nugent 4. At enrollment with acute BV, P5-aBV had a unique profile among the group, characterized by low Lactobacillaceae (*L. iners*), low Actinobacteridae (*G. vaginalis*), but high levels of Bacteroidaceae/Prevotellaceae (*P. timonensis*), Clostridiales-BVAB2/3 (BVAB2), Fusobacteria (*S. sanguinegens* variant), Mycoplasmatales (*M. hominis*), and *Streptococcus* (*S. agalactiae*). After treatment, P5 had a higher level of Actinobacteridae (*G. vaginalis*) than the other patients and a Nugent score of 4, and therefore is characterized as having only a partially successful response. She reported odor or discharge throughout the month, until she was diagnosed as with BV by Amsel, at an intermediate Nugent score, 4, by day 77.

Relative LB content as an overview of vaginal microbiome status. Oligomers that specifically block amplification of LB (LB-blockers) in an otherwise universal PCR of the 16S rRNA gene allow detection of the subdominant species in healthy or PT BV patients (Lbq-PCR), such as those barely visible in FIG. 10. It follows that the Cq of BV samples in Lb-qPCR, in which LB is subdominant, should change slightly or not at all in blocked versus unblocked reactions, and the Cq of healthy samples, often composed of >99% LB, should shift up by more than 6-7 cycles ($2^6$=64; $2^7$=128) with LB-blocking. Consistently, the average delta Cq ($\Delta$Cq) value between blocked and unblocked samples taken from our 5 patients during acute BV, was 1, whereas the average $\Delta$Cq was 11 in the PT samples. Furthermore, $\Delta$Cq values were intermediate (~4) in PT samples in patients who recurred rapidly or had an incomplete response (P2, P5), and were much higher, 8-15, in the remaining patients who either recurred more slowly or not at all (FIG. 11).

Figure 11:
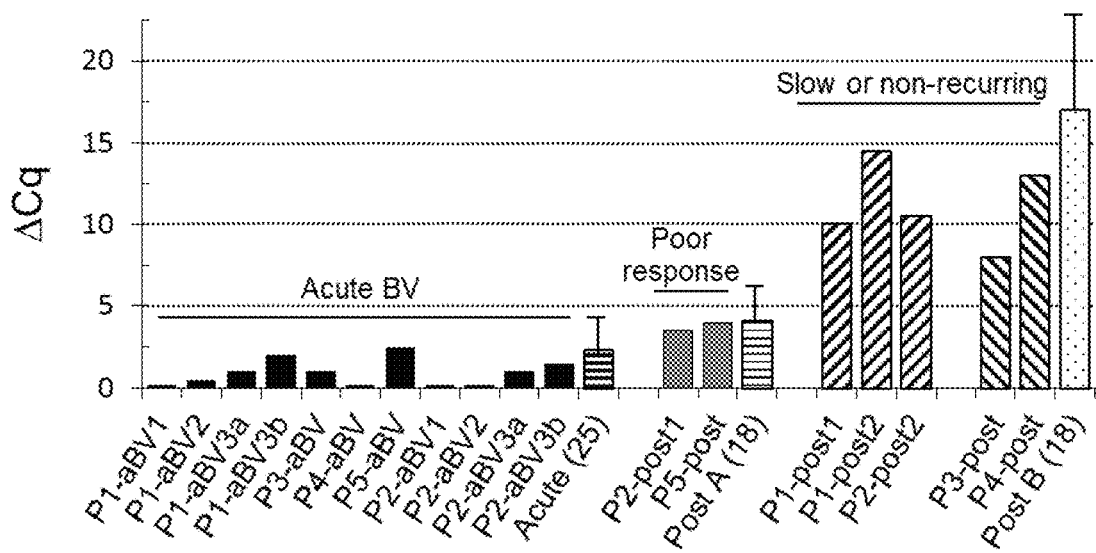
FIG. 11. ΔCq values in samples from RBV patients at visit 1 (acute BV, black bars) versus PT visit 2 (grey bars). Patients who recurred rapidly or responded poorly (P2, P5) are shown in dark grey; patients who did not recur or did so slowly are in light grey (P1, P2 after her 2nd recurrence, P3, P4). Acute (25); Post A (18) and Post B (18) bars represent averages of a separate collection of patients (numbers in parentheses) who were only sampled at the initial acute BV and/or the PT visits, with indicated standard deviations.

Lb-qPCR analysis was also performed on a separate, larger patient group of recurrent BV patients before and after metronidazole treatment (FIG. 11). Data confirm that the ΔCq scores were consistently low (2.3±1.6) in acute BV samples (Nugent average 8.8±1.0), and fall into two distinct categories after treatment: Post A, ΔCq scores averaging 4.1±2.2 (Nugent average 2.2±4.0) versus Post B, ΔCq scores averaging 17±6 (Nugent average 0.8±1.2). An out-group of 28 patients with no history of BV had an average ΔCq value of 16.0±5.0 (data not shown). Differences were not significant between the Post B and healthy groups (p=0.5437), small but significant comparing acute BV and the Post A groups (p<0.0034) and significant and large comparing Post A and Post B (p<0.0001; 95% C.I. 9.8-16).

Figure 12:
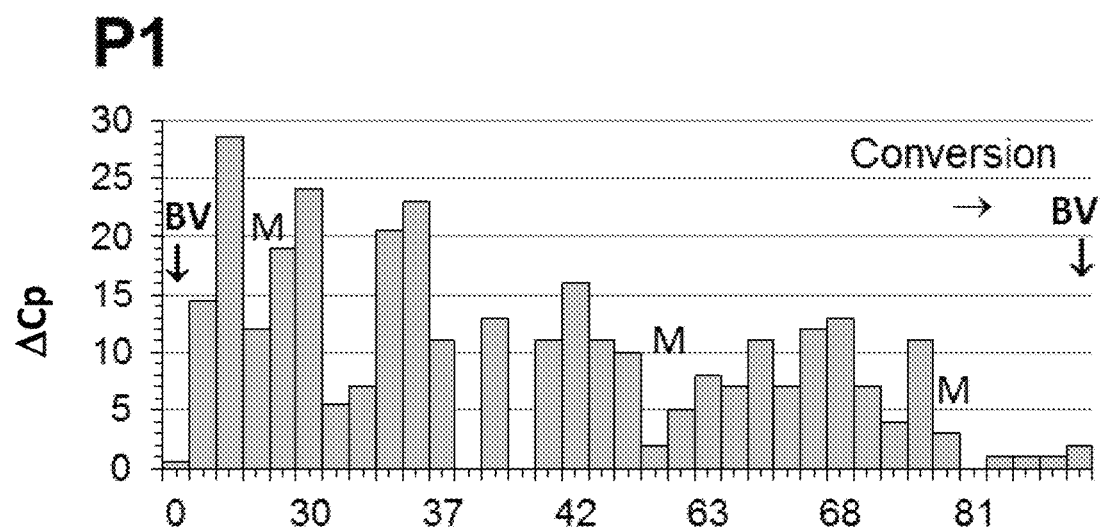
FIG. 12. ΔCq values define conversion events before acute BV. Conversions DCq values persistently <5 occurred 10-40 days before symptomatic BV in recurring patients P1 and P2, but not in non-recurring patients P3 and P4. Values remain <5 for most of the interval in P5. BV=acute BV by Nugent and Amsel; M=menses; C=coitus.
Figure 12:
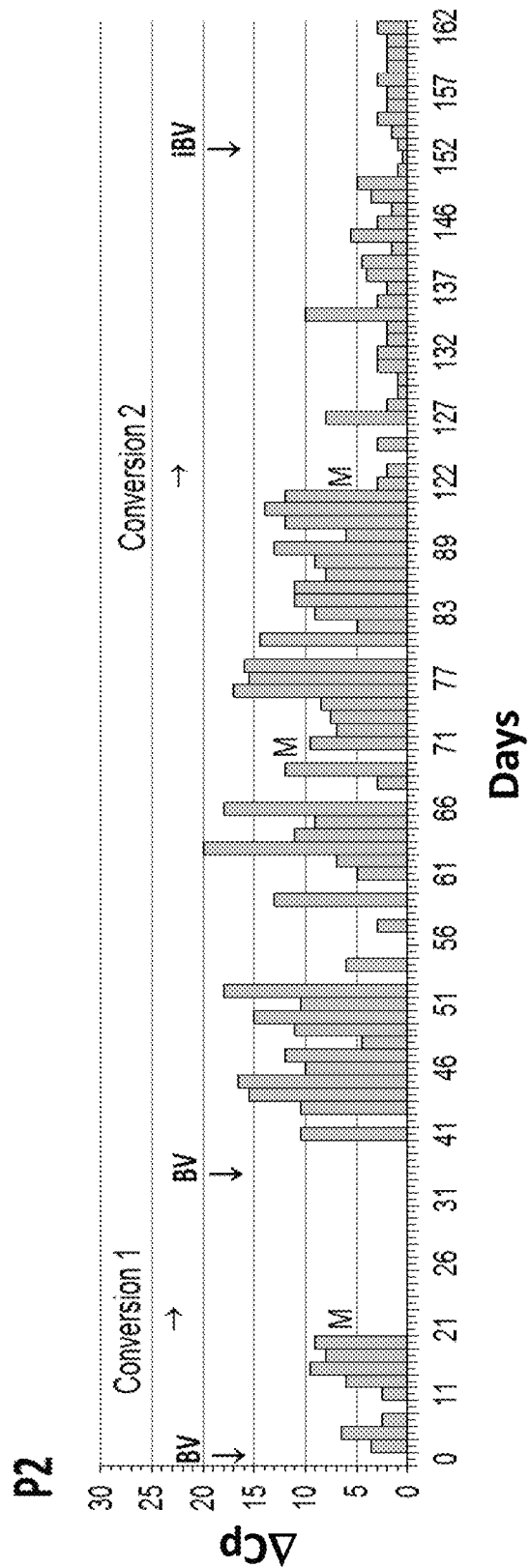
Figure 12:
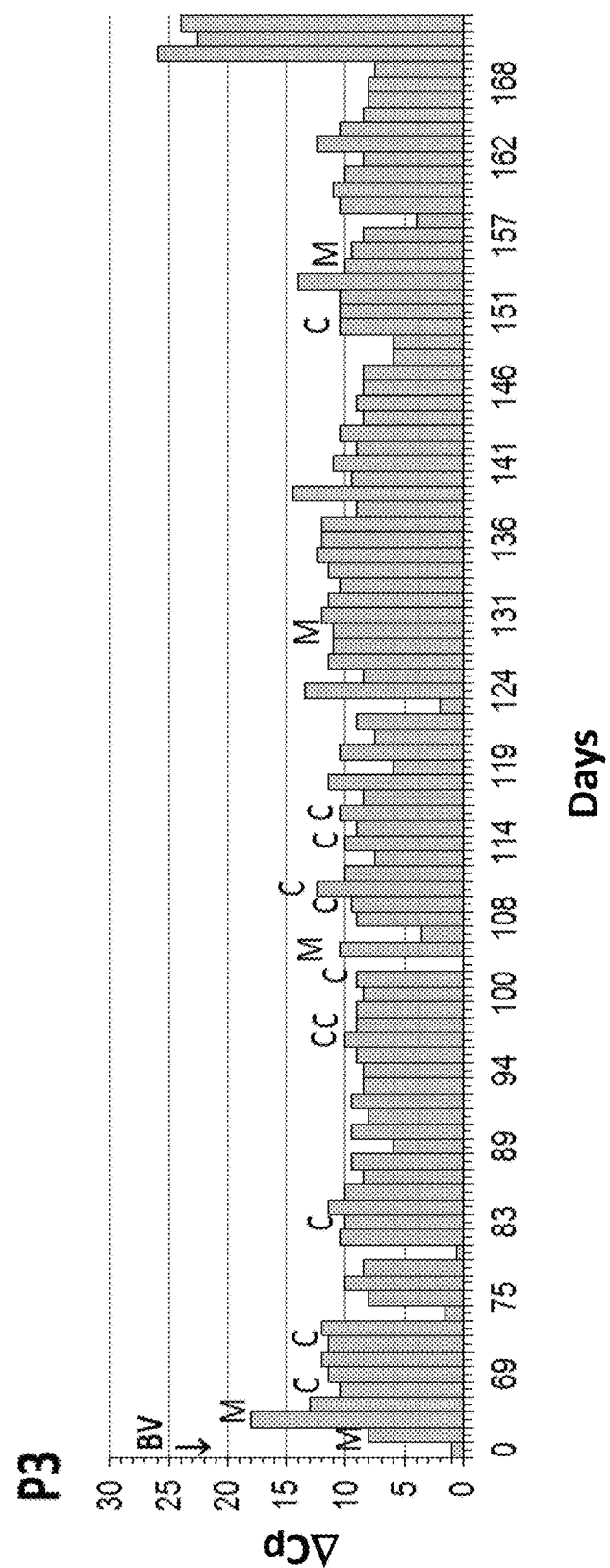
Figure 12:
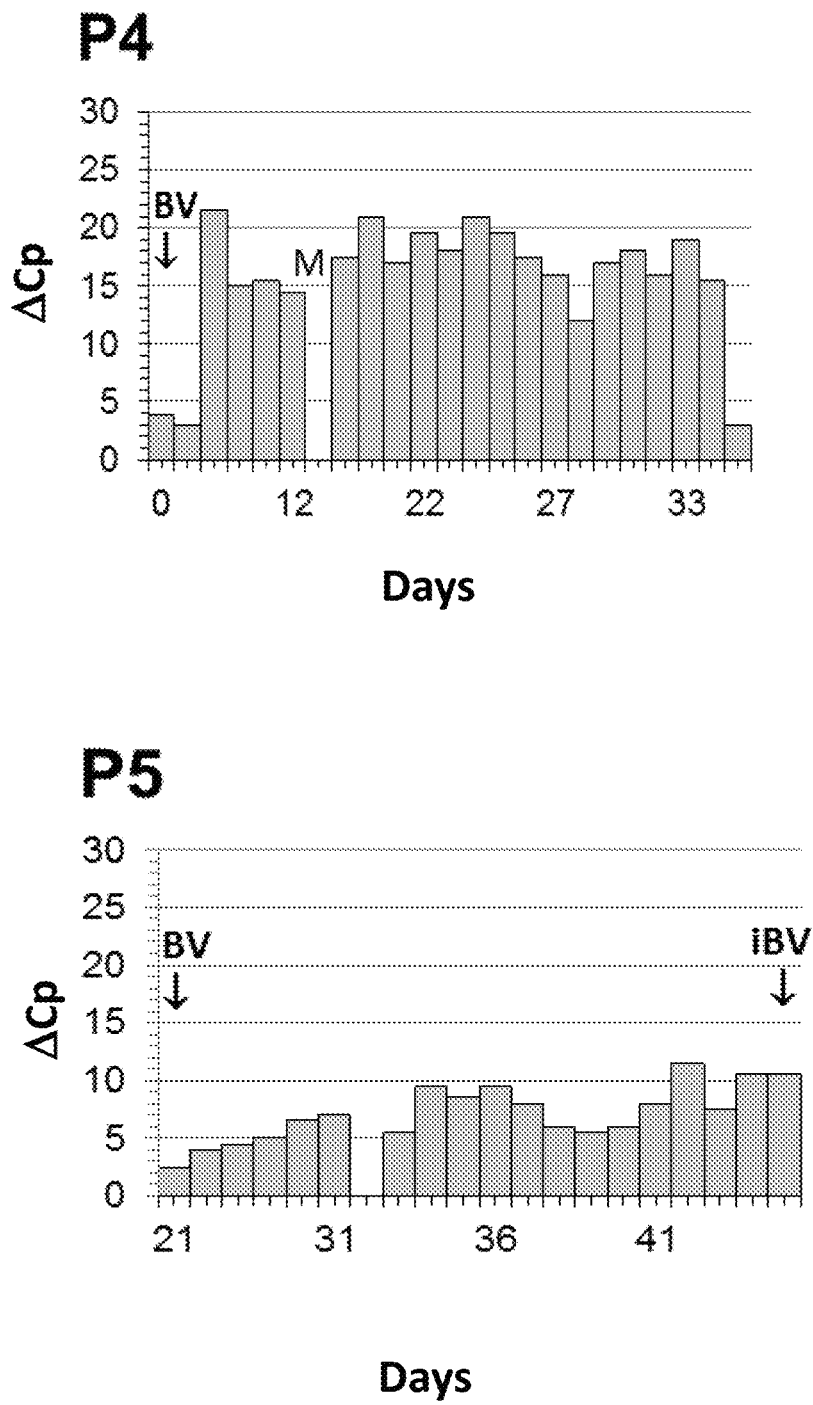

Conversion of vaginal microbial profiles preceding acute BV. ΔCq was used to track the overall compositions of daily vaginal samples of five patients as they either recurred with BV or maintained a nonrecurring status (FIG. 12). Values fluctuated on a daily basis, but several useful trends were noted. P3 and P4, who did not recur, maintained high ΔCq values (i.e., low titers of non-LB sp.) throughout their PT histories, averaging 10 and 15, respectively. In these non-recurring patients, lower ΔCq values were seen only sporadically for a single day, and often associated with menses or 2-3 days after coitus. In contrast, rapidly recurring P2 showed an initially weak response to treatment, average ΔCq=5, which dropped to near 0 after menses beginning at day 21, and remained near 0 for 2 weeks, at which time BV was clinically diagnosed. P2 responded somewhat better to her second treatment from day 41; her ΔCq sustained an average of 9, until after menses at day 121. This interval, however, was unstable; there were several days with sequential low ΔCq values <5, and half of the samples had ΔCq values <10. After her final menses, ΔCq values averaged <3 and never rose above 10; eventually self-reported symptoms of BV recurred. These sustained intervals of low ΔCq values, days 21-35 and 121 onward are referred to as conversion, reflecting large declines in LB content and take-over by a variety of non-LB species.

P1 recurred but more slowly than P2 in her initial recurrence (3 months versus 1 month). Consistently, P1 had ΔCq values of ~20 for the first month, versus 5 for P2, and P1 remained symptom-free for ~90 days, versus 35 days for P2. However, ΔCq values for P1 trended downward after successive menses (averages 22, 12, 8) until conversion after her last menses, at which time her ΔCq averaged 1.

All conversions in P1 and P2 immediately followed menses and all preceded BV by more than a week. No conversions were seen in non-recurring patients P3 and P4. Not all menses are associated with conversion, but in P1, menses associated with progressive declines in average ΔCq values.

Figure 13:
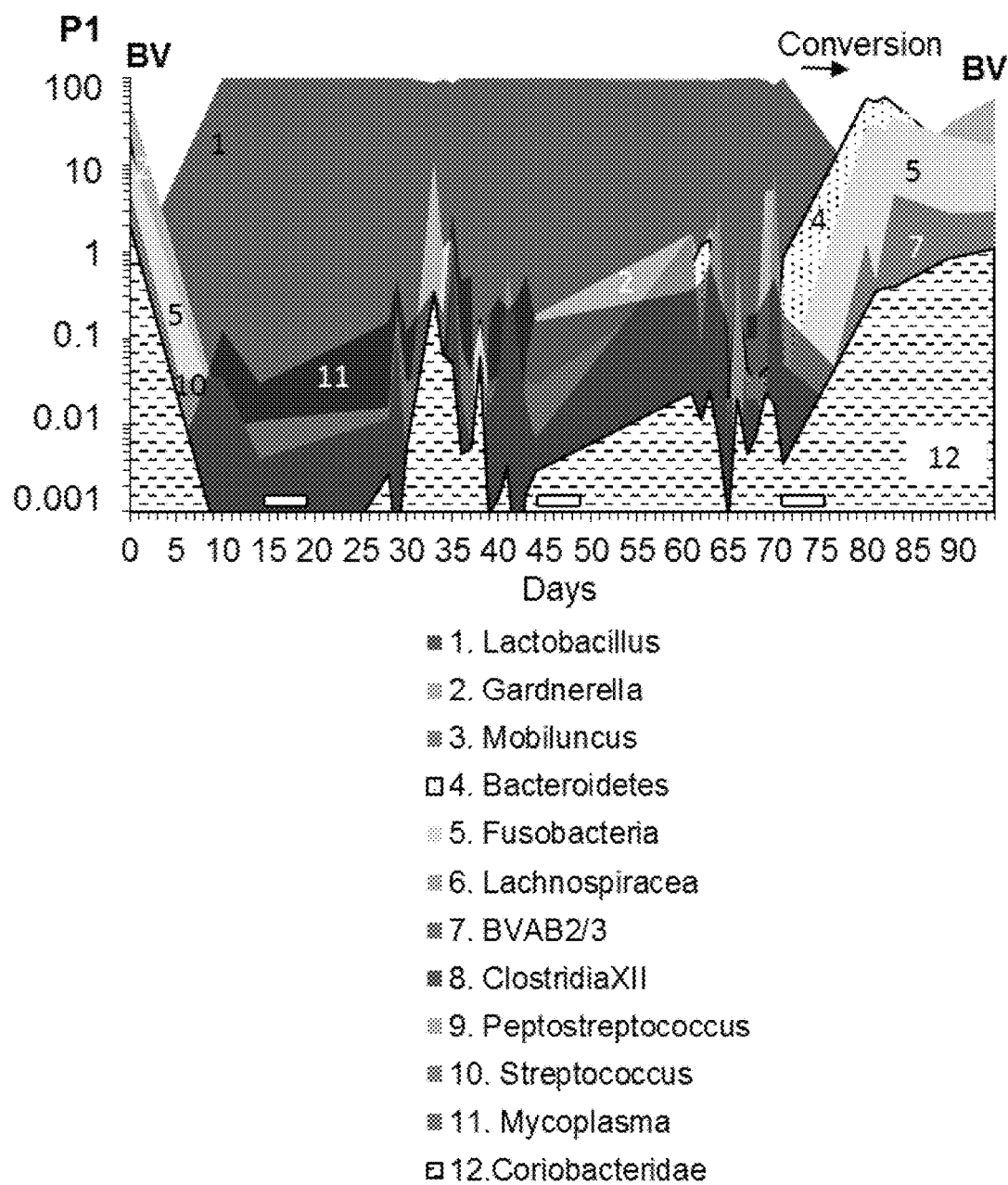
FIG. 13. Microbial profiles of near-daily vaginal swabs from patients with histories of recurrent BV, characterized with 11 PB-qPCR targets (legend). Data are converted to % total titers and depicted on a log scale. Top panels of P1 and P2 show the expected rise to dominance of LB after treatment, and conversions before acute BV. In both patients, sharp increases are seen in *G. vaginalis*, (2), *Prevotella* (4), *L. amnionii* (5), BVAB2 (7), and *Mycoplasma* sp. (11). Patients P3 and P4, who did not recur, show sustained dominance of LB after treatment, and their non-LB populations remain generally at <1%, with frequent transient spikes. Red bar=menses; l=coitus.
Figure 13:
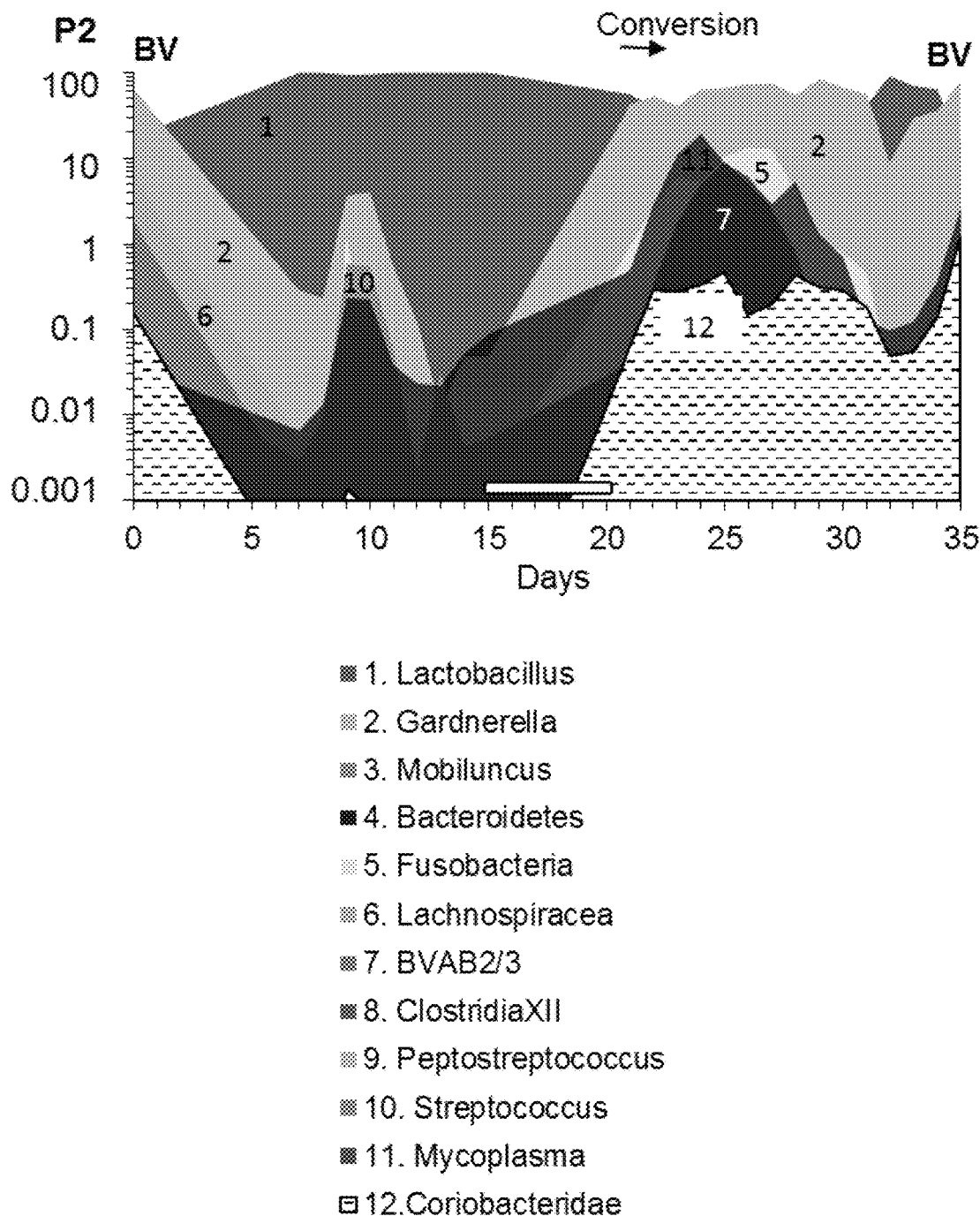
Figure 13:
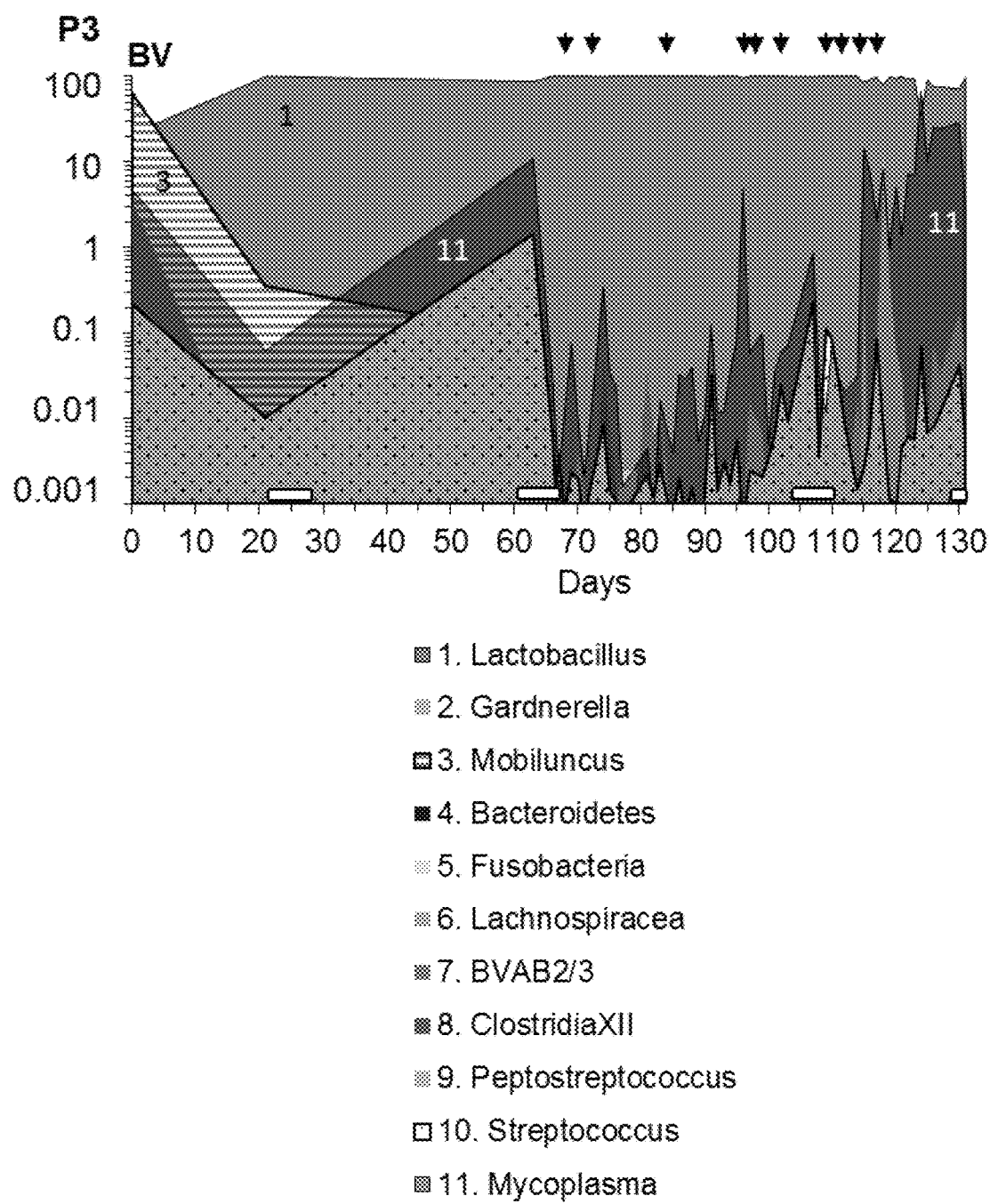
Figure 13:
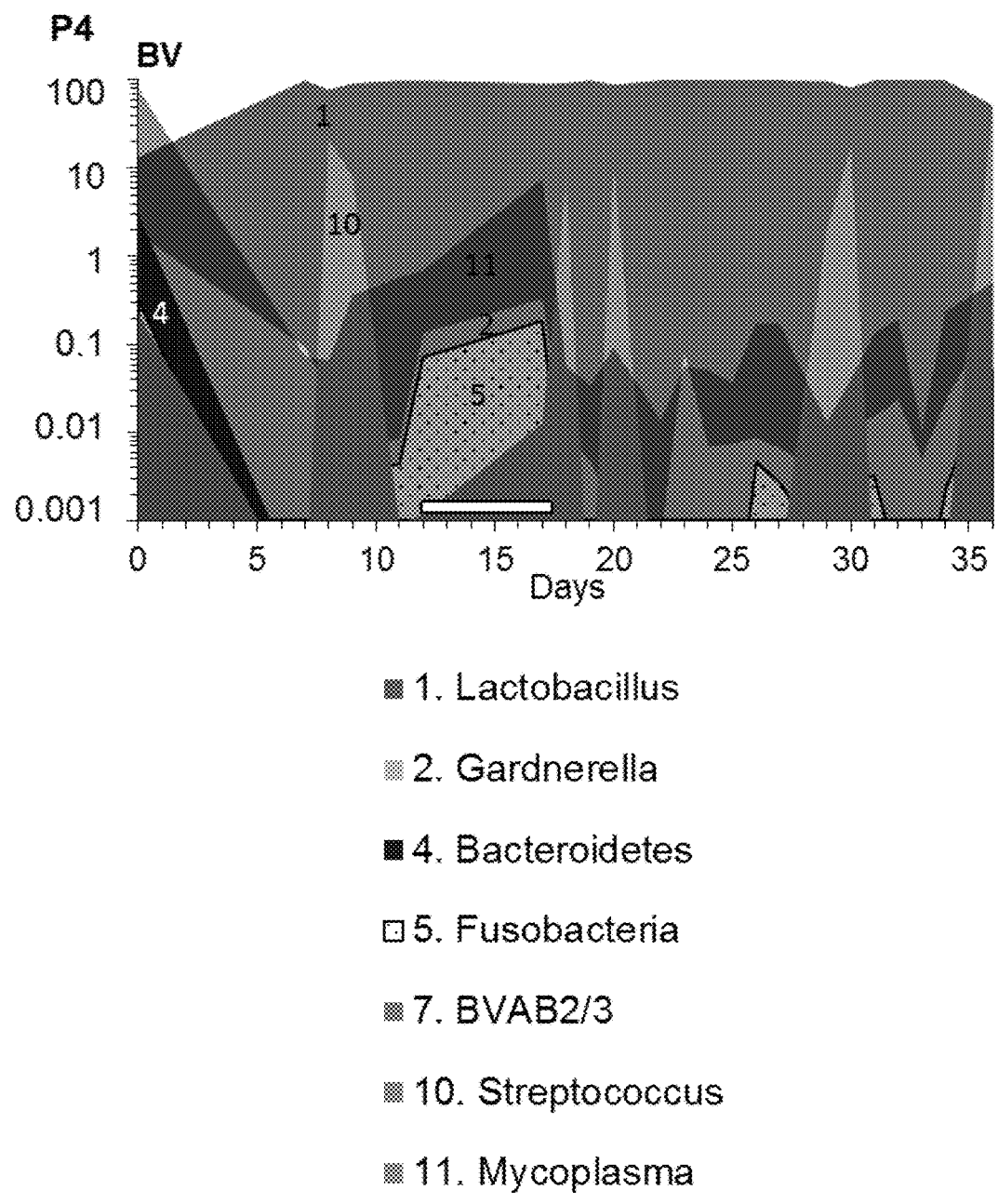

Conversion events. P1. Conversion events were characterized in more detail by PBq-PCR (FIG. 13). In P1 at day 80, after menses, there was a 20-fold drop in LB, concomitant with a 100-fold increase in Actinobacteridae (*G. vaginalis*). Simultaneously, Bacteroidaceae Prevotellaceae (*P. timonensis*), Coriobacteriadae (*Atopobium vaginae*), Fusobacteria (*Leptotrichia amnionii*), and uc Clostridiales-BVAB2/3 subgroup (BVAB2) increased 10-1000 fold. Smaller changes in *G. vaginalis* and BVAB2 began before conversion, around day 60, preceded by and associated with spikes and species shifts in *Streptococcus*, from the *S. anginosus* group (*S. anginosus*, *S. constellatus*, and *S. intermedius*) to the *S. mitis* group (*S. mitis*, *S. cristatus*, *S. infantis*, *S. oralis*, and *S. pneumonia*). Notably, the rise in BVAB1 occurred at the end of conversion, at day 94.

The ΔCq metric alone reliably defined conversion events, and all 3 were confirmed and further characterized by PB-qPCR data. The initial BV population, dominated by Actinobacteridae (*G. vaginalis*), sub-dominant Fusobacteria (*L. amnionii*) and BVAB2, is restored by treatment to dominant Lactobacillaceae, where it remains until conversion. These groups rise and fall frequently, over several orders of magnitude and often together, trending upward after the penultimate menses, before recurrence was diagnosed.

Figure 14:
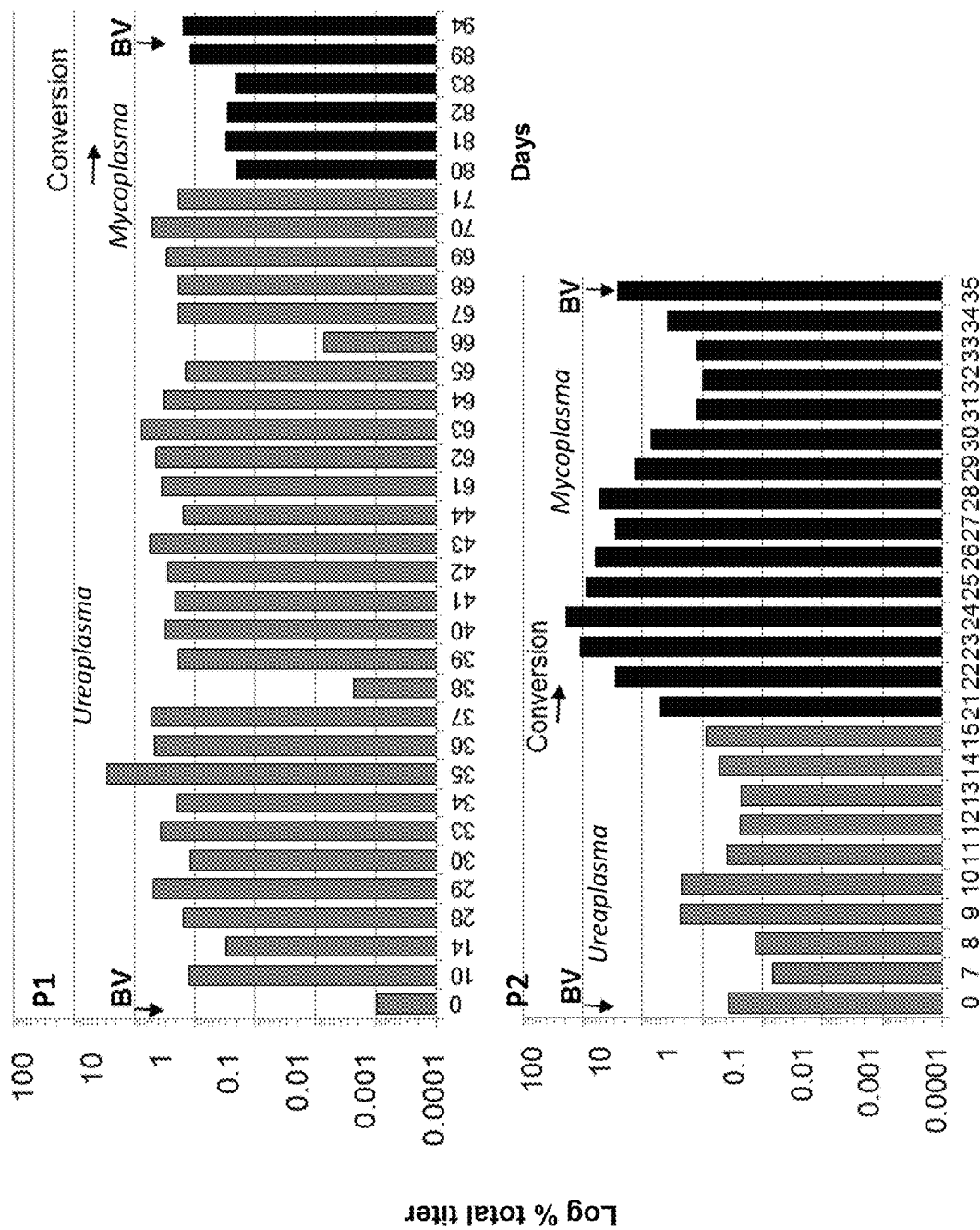
FIG. 14. Shifts in dominant species common to conversions in P1 and P2. Panels represent qPCR data using Mycoplasmatales primers (top) or *Enterococcus* primers (bottom). Amplicons were sequenced to identify species, or in some cases were identified by their distinguishing melt curves that matched those of the sequenced products.
Figure 14:
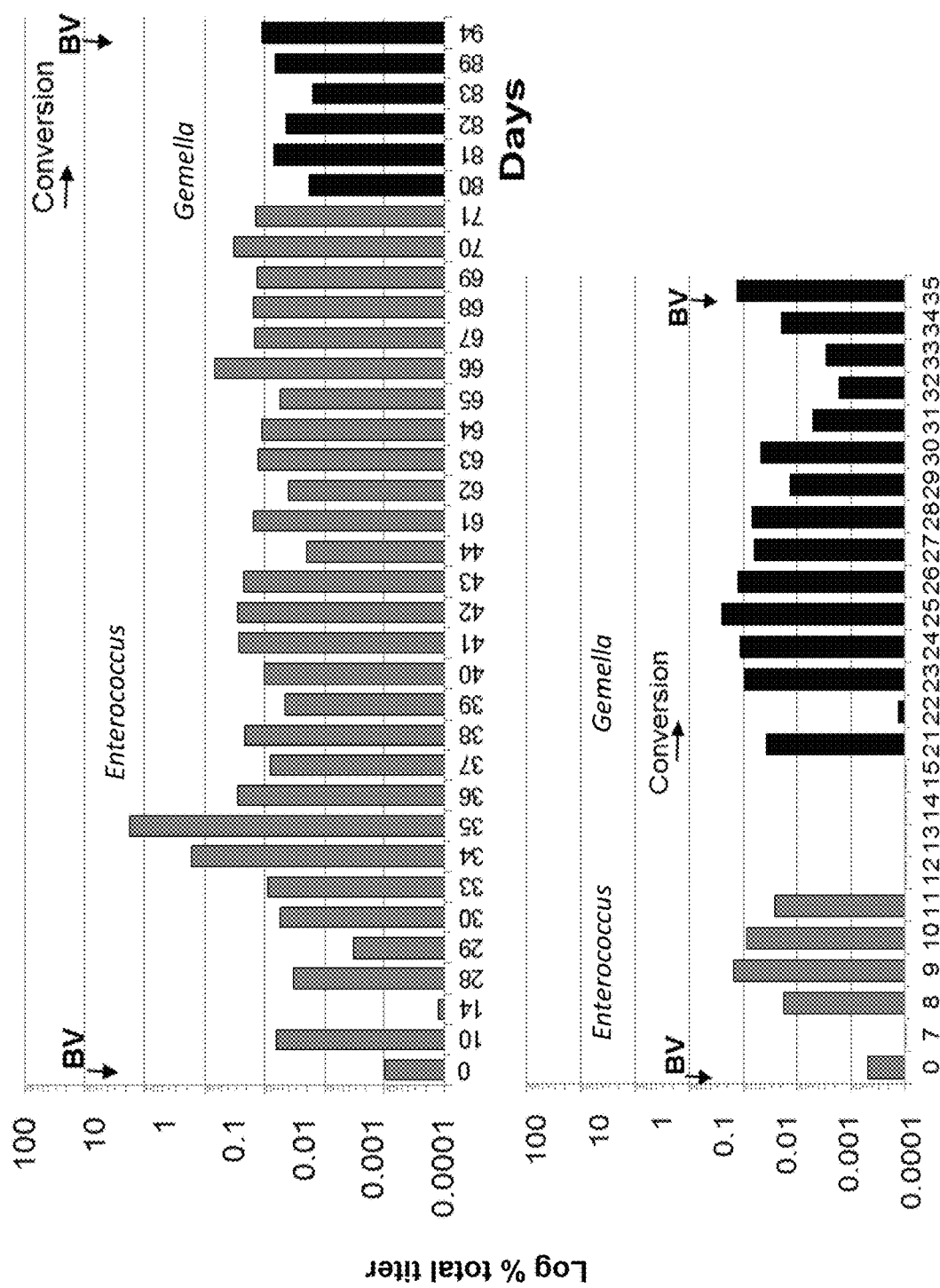

Conversion in P1 was coincident with species shifts in some target groups (FIG. 14). In both recurrent patients (P1 and P2), qPCR with Mycoplasmatales primers (FIG. 14, top) detected *Ureaplasma parvum* as the dominant species in pre-conversion samples, but switched to *Mycoplasma* sp. throughout conversion. Quantitative PCR with Enterococcus primers (FIG. 14, bottom), revealed that pre-conversion samples were dominated by *E. faecalis*, which switched to a non-target *Gemella* sp. throughout conversion. Semi-quantitative PCR (not shown) indicated that the cytolysin $Cyl_L$ gene, present in one third of clinical strains of *E. faecalis*, was present at increasing levels preceding conversion.

Conversion events in P2 (FIG. 12, 13) occurred immediately after her first and third menses after treatment preceding BV. The first of these was characterized by and a 100-fold increase in Actinobacteridae (*G. vaginalis*) and a somewhat later and oscillating decline in LB. In P2, as with P1, there were sharp increases in Fusobacteria, (mostly *L. amnionii*), Coriobacteridae (*A. vaginae*), and BVAB2 (FIG. 13). Before conversion, P2 did not achieve the same level of reduction of multiple species compared to P1, and like P1, several groups shifted up or down together over several orders of magnitude.

P3 and P4 did not recur and had none of the above shifts that defined conversion in P1 and P2. In contrast to both recurring patients, P3 and P4 maintained high relative content of LB throughout their PT histories, and neither had dominant Actinobacteridae (*G. vaginalis*) populations at onset or during the course of study; instead, they presented with dominant Mobiluncus (*M. mulieris*) and *Mycoplasma* spp., respectively. BVAB1 and BVAB2 never rose above 0.1%, and averaged <0.003%, throughout remission. *Enterococcus* and its cytolysin $Cyl_L$ gene was largely absent in P4, but were detected throughout the sampling interval, mostly at low titer, in P3 (semi-quantitative PCR, data not shown). P4 had sporadic, 1-2 day spikes of *Streptococcus* species, again, not sufficient to induce conversion. As in P1 and P2, these patients had frequent, coordinate shifts of multiple groups over orders of magnitude, but generally remaining below 1% of total titer.

The two most important findings from the described monitoring of near-daily changes in the vaginal microbiota of five recurrent bacterial vaginosis (RBV) patients, using PB-qPCR and LB-blocked qPCR, were 1.) conversion, the loss of LB and its replacement by other species, occurs well before symptomatic BV, and 2.) PT samples were separable into two groups on the basis of relative LB content, such that those with complete dominance (high ΔCq) were seen in patients with no or slow recurrence. These two distinct categories were also seen in a separate collection of patients. In both patient sets, PT samples were Amsel negative and Nugent 0-3, suggesting that these parameters are not useful indicators for the two types of recurrence. Patients did not convert from *L. iners* to *L. crispatus* after treatment, even in those who did not recur.

ΔCq scores at PT could be a new tool for clinicians to evaluate the efficacy of treatment and intervene with individualized therapy, despite the absence of symptoms. ΔCq could also be used to monitor RBV patients, to allow intervention at conversion and avoid recurrence.

Conversion occurred immediately after, or possibly during menses, more than a week before symptoms, in all three episodes of acute BV, but was not observed in non-recurring patients. All conversions have the drop in *L. iners* in common. *P. timonensis* replaced *L. iners* in P1, but *G. vaginalis* was first to dominance in P2. Conversion occurred rapidly in P2, at the first PT menses, perhaps foreseeable from her poor (low) ΔCq value after treatment, and perhaps suggesting that P2 hosts more virulent strains of the BV-associated anaerobes. The slower recurrence in P1 corresponded to a higher PT ΔCq value, and suggests she took a different route to recurrence. This route may involve smaller, sequential perturbations after each menses, which gradually reduced dominance of *L. iners*. Samples taken during conversion in P1 and P2, or during specific days in P3 and P3 with LbRC scores <5, would likely have been described as asymptomatic BV by Nugent and Amsel criteria.

Conversion, as a potential lead-in to acute BV, raises the question of what initiates the process. Without being bound by theory, patients that host more virulent strains, e.g. of *G. vaginalis*, may only need menses to tilt the balance toward conversion. Patients with less virulent strains may need other factors. Species showing transient increases in pre-conversion samples of P1 included *Streptococcus* sp. and BVAB2. Another candidate is *E. faecalis*; it is prevalent before conversion, but did not increase during conversion or acute BV. It was consistently present in P3, who did not recur in this study interval, but had a history of RBV. Non-recurrent P4 had low, intermittent levels, and it is infrequently present among patients with no history of BV. Unpublished data indicates that vaginal *E. faecalis* strains, if beta-hemolytic, are strongly antagonistic to most vaginal LB species in vitro, whereas alpha-hemolytic *E. faecalis* strains are not. That an *Enterococcus* cytolysin might play a role in BV was suggested by reports that a bacteriocin from *E. faecium* inhibited vaginal LB species. However, this bacteriocin/cytolysin is not related in sequence, is not hemolytic, and was not detected in the described vaginal samples.

As a working model, and without being bound by theory, beta-hemolytic *E. faecalis*, or any species that has acquired its cytolysin operon, may be responsible for initiating early changes in the vaginal microbiota that leads to conversion and BV, at least in some patients. This cytolysin is induced in response to target cells, in this case, erythrocytes during menses, and either directly or indirectly, contributes to the reduction of LB and overgrowth of non-LB. Direct reduction may involve direct lysis of susceptible species or strains of LB. Indirect reduction may involve release of growth-limiting iron by hemolysis, taking away the advantage otherwise afforded by the ability of LB species to thrive in an iron-poor environment and possibly sequester iron away from other species. The cytolysin activity may precede, augment, or replace vaginolysin from *G. vaginalis*, which is hemolytic but not bacteriolytic, and varies widely in expression levels among isolates from acute BV samples. The extent to which cytolysin activity is important among individuals may also depend on the degree of virulence of the non-LB species, or the degree of susceptibility of specific LB species. It may also depend on the severity or length of the menses, a link established by the timing of BV with menses and its reduced prevalence among women using estrogen-based contraceptives.

Recurring patients were repeatedly dominated by *G. vaginalis* at acute BV episodes, whereas nonrecurring patients were predominantly Mobiluncus (*M. mulieris*) or *Mycoplasma* sp. when acute. *G. vaginalis* sub-dominance in acute BV samples could be expected from NGS studies; for example, only 53% of 114 acute BV patients analyzed by 16S rRNA gene pyrosequencing had titers above 10%.

Both acute and in-remission samples were diverse, positive for many of the tested target species, and dynamic, fluctuating over many orders of magnitude in sequential samples. Many of these never rose above 1% throughout the study interval, and they tended to rise and fall in unison, often daily, as sub-dominant species. This reflects the dynamic nature of the competing species in the vaginal "ecosystem", and is consistent with sequential variation seen in other studies using Gram staining, species-specific qPCR or 16S rRNA gene pyrosequencing. Despite this diversity, the intra-patient similarity among BV episodes for P1 and P2 was remarkable. Not only were there similarities in percentages (e.g., the amount of *G. vaginalis* during clinically confirmed BV episodes differed by less than 6% in P1 and 8% in P2), but frequently in species. For instance, in P1, *Megasphaera/Dialister/Veillonella* transitioned from *Megasphaera genomosp.* type 1 during BV to *Veillonella* sp. during remission and back to *Megasphaera genomosp.* type 1 during conversion and relapse.

The dominant LB species of all five patients at acute BV was *L. iners*, which was the dominant species in PT samples. The latter resemble community III of healthy women as defined by a16S rRNA gene pyrosequencing study largely by the single criteria: dominance by *L. iners*. Members of this community rarely switched to other types over 4 months, notably not converting to a sustained high Nugent score, but they did have a high incidence of sporadically high Nugent scores. Community III may consist of subtypes, composed of different species present at <0.1%, still representing substantial actual titers. The subgroup composition may influence whether and how frequently these women undergo conversion. Dominance by *L. iners* is a strong risk factor for BV, suggesting a causal link, such as its putative lesser ability to protect the vaginal mucosa from conversion, e.g. due to its inability to produce hydrogen peroxide. The opposing interpretation is that *L. iners* has been selected for among recurrent BV patients, because it is impacted less by BV treatments or because it better exploits the vaginal environment during acute BV and drives recovery.

Some of the five patients were colonized with *Candida*. P2 was colonized with *C. albicans* at each clinical visit. P3 had intermittent pruritus due to culture-confirmed *Candida parapsilosis* with no recurrence of BV. P5 became culture positive for *C. albicans* at her final visit, co-incident with recurrence of BV. These observations raise the issue, but do not address, whether there are reciprocal influences between *Candida* and the vaginal bacterial microbiota. The clinical perspective, based on culture and microscopy, is that co-infections of *Candida* and BV-associated species are common (20-30% of BV patients are co-infected), but only rarely do symptoms reflecting both infections (mixed vaginitis) arise. Indeed, vaginal colonization or infection with *C. albicans* did not perturb bacterial profiles, based on culture, in healthy women or in those with BV. Molecular studies looking concurrently at fungal and bacterial vaginal populations are rare and preliminary. A pyrosequencing study did not show strong correlations between *Candida* colonization and dominant bacterial populations among asymptomatic women. In another study, 21 patients with recurrent vulvovaginal candidiasis (RVVC) were compared to 19 healthy women using T-RFLP, to find no association of diversity or bacterial composition (notably *L. iners* versus *L. crispatus*) with RVVC. Preliminary analysis (PB-qPCR) of a study that tracked 28 RVVC patients after they were taken off of long-term fluconazole therapy, also did not find any correlation of bacterial profiles with recurrence or acute episodes of VVC. More rigorous molecular studies, with careful clinical assessment of BV and VVC, are needed to support or refute this counter-intuitive perspective, that *C. albicans* can colonize and proliferate, indifferent to its bacterial environment.

Based on the described findings, recommendations can be made at the post treatment stage (visit or self-swab), for example, that ΔCq values less than 2-3 warrant longer or more aggressive treatment, or that values in this range seen in RBV patients in remission, particularly after menses, signal conversion and a need for further treatment. Similarly, defined subgroups of acute BV profiles may be useful in predicting recurrence or deciding how aggressively to treat.

Example 3

In particular embodiments, the systems and methods disclosed herein are referred to as LB Relative Composition (LbRC). LbRC can diagnose BV regardless of the composition of BV-associated anaerobes, which vary by patient, region, race, and time of progression of signs. LbRC can also predict recurrence of BV. LbRC can run >40 batched assays at a time, commensurate with hospital throughput. LbRC is also a powerful tool for examination of species involved in causing conversion.

Figure 15:
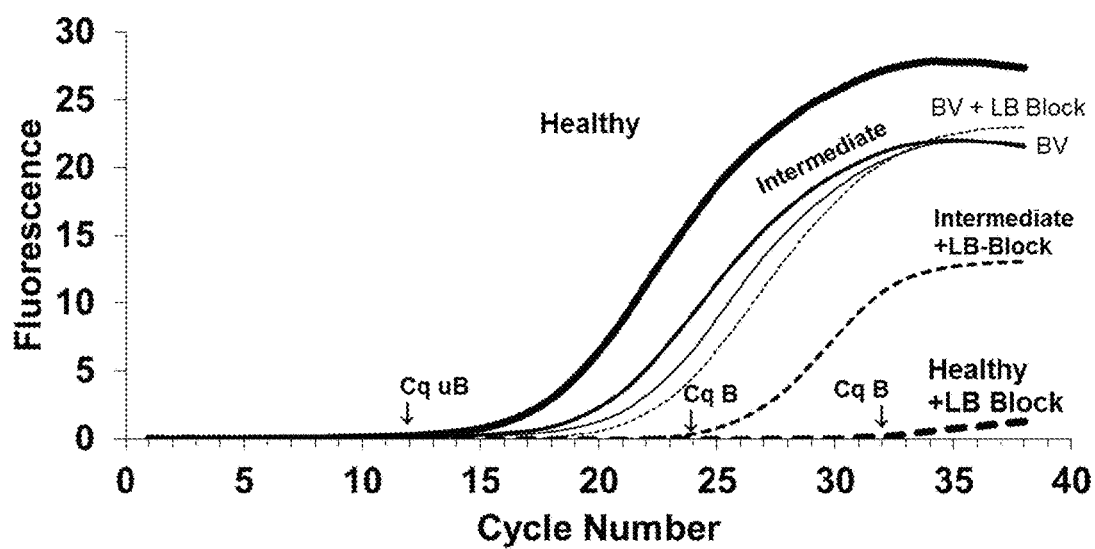
FIG. 15. LbRC is based on Cq shifts with versus without LB-blocker. The cycle at which fluorescence of dsDNA first rises above background, Cq, is inversely proportional to initial template concentration and so measures that concentration. Healthy samples dominated by LB, have drastically increased Cq values when amplified with LB-blockers (black dashed) compared to unblocked (black solid), to give ΔCq values of 15-20.

LbRC is based on quantitative PCR (qPCR) using broad-spectrum bacterial 16S rRNA gene primers, in the presence versus absence of inhibitors of LB amplification (LB-blockers). LB typically dominates healthy, pre-BV, and successfully treated BV vaginal populations. However, its relative level drops from 20 to 1000 fold in acute BV samples. qPCR of a normal population reports a high titer (low Cq value) reflecting the LB content, but the same sample reports a low titer (high Cq value) in the presence of LB-blocker, since only the non-LB species are being "counted". In contrast, an acute BV sample reports the same titer with or without LB-blocker, because it contains little to no LB. Therefore, the change in Cq, ΔCq, is large in healthy samples, small in BV samples, and the range between potentially reflects gradual changes in vaginal health (FIG. 15).

Figure 16:
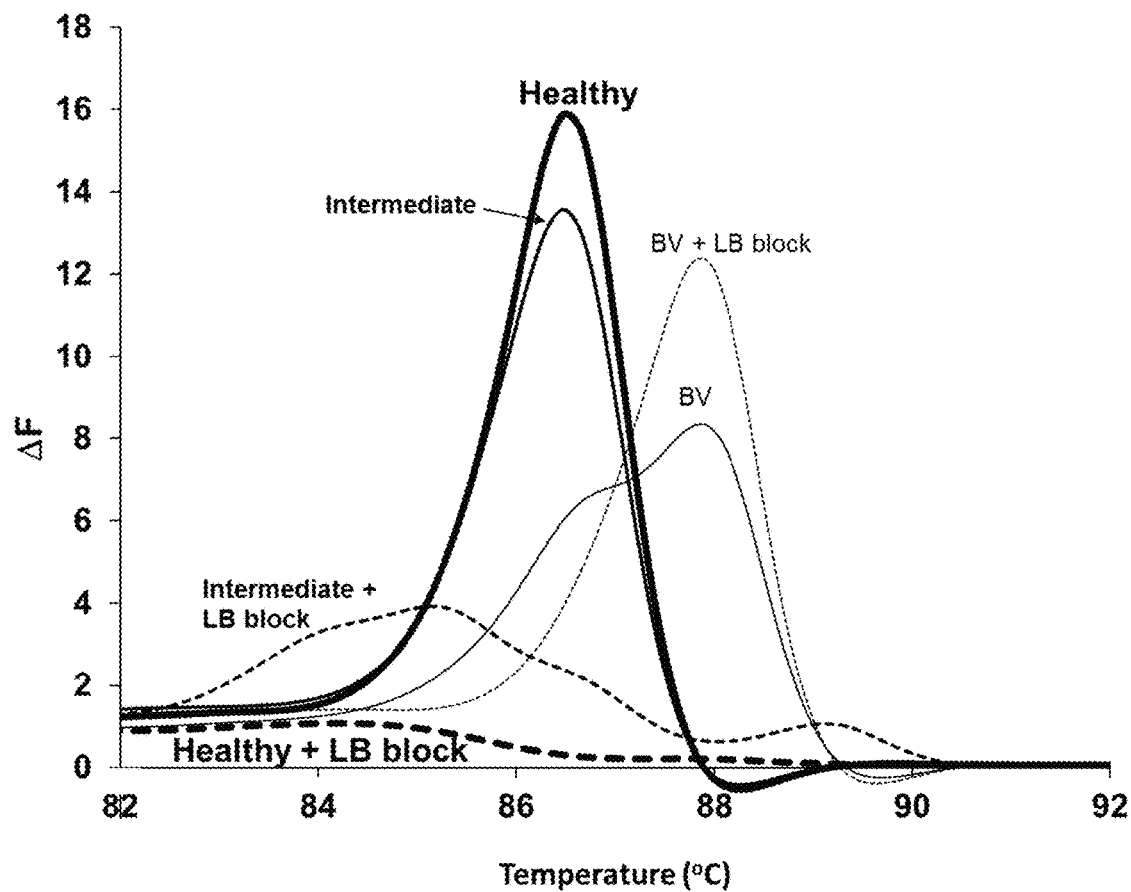
FIG. 16. Melt curve analysis of vaginal samples±LB-blocker. Healthy vaginal samples are mostly LB, with typical Tm ~86.5° C. depending on the species (black, solid). In the presence of LB-blockers, which inhibit amplification of LB but permit it for other species, these samples generate very little product and no melt curve (black, dash). A sample from an asymptomatic patient who is not quite healthy (BV-2 no & LB-blocked) may show non-LB species after blocking. Samples from BV patients, mostly non-LB, melt at varying temperatures depending on the dominant species, and show no blocking (BV-1 no & LB-blocked) or selective blocking of a subpopulation of LB (left shoulder of solid (BV-2 no block).

In addition to ΔCq, melt curve analysis of the amplicon generated both with and without LB-blocker, provide additional information, particularly about non-LB subgroups. Vaginal LB species can be identified as a group by their Tm peak between 84.3° C. and 87.1° C., coupled with their signature ΔCq with LB-blockers. Relative to LB peaks, BV-associated anaerobes appear as peaks shifted as follows: *Gardnerella vaginalis*, BVAB2, and *Dialister* shift +2-2.3° C. (BV-2 no block FIG. 16), *Atopobium vaginae*+2.5° C., BVAB1 −1° C., *Leptotrichia amnionii* −2-2.5° C. *Prevotella, Mycoplasma, Streptococcus*, and *Enterococcus* spp. have melts in the range of LB spp but do not show Cq shifts. When these species are relatively higher in titer, but not dominant, they appear as shoulders or $2^{nd}$ peaks with the LB-derived peaks (FIG. 16). In samples in which they are relatively low, they only appear with LB-blocking. In acute BV samples, they become the dominant or sole peak, regardless of LB-blocking. The presence of any non-LB melt peak can be considered to be more important than the temperature/species of that peak.

Analyses using LbRC can be performed in 96 well plate platforms with minimal interference by environmental contaminants, requires no hands-on manipulation once the qPCR is running, and provides automated categorical calling of the output data. LbRC enables testing and implementation of individualized treatment alternatives, to prevent or delay recurrence. It also makes feasible the detection of vaginal samples, in a series from remission to recurrence, which first show conversion from LB dominance, well before symptomatic recurrence. This will enable detection of species that cause this conversion, which in turn may allow new approaches to therapy.

A key advantage in measuring vaginal health by ratios of LB to non-LB populations is that it anticipates that the detailed composition of individuals with BV is variable. To demonstrate this, the levels of false positives and negatives that would have been called using PCR detection or qPCR quantification of BV-associated species in vaginal samples of healthy versus acute BV patients were calculated (compositions were determined by NGS).

The results show that other assays have high rates of false negatives or positives, compared to the % LB metric, which is just one of the parameters tapped in LbRC. Using the LbRC strategy also avoids the problem that diversity of target species, e.g. those in the Clostridia group like BVAB1,-2,-3, is greater than anticipated in the design of specific primers, so that targets in individuals with even high titers of similar species which mismatch to these primers will be invisible or under-counted.

Figure 17:
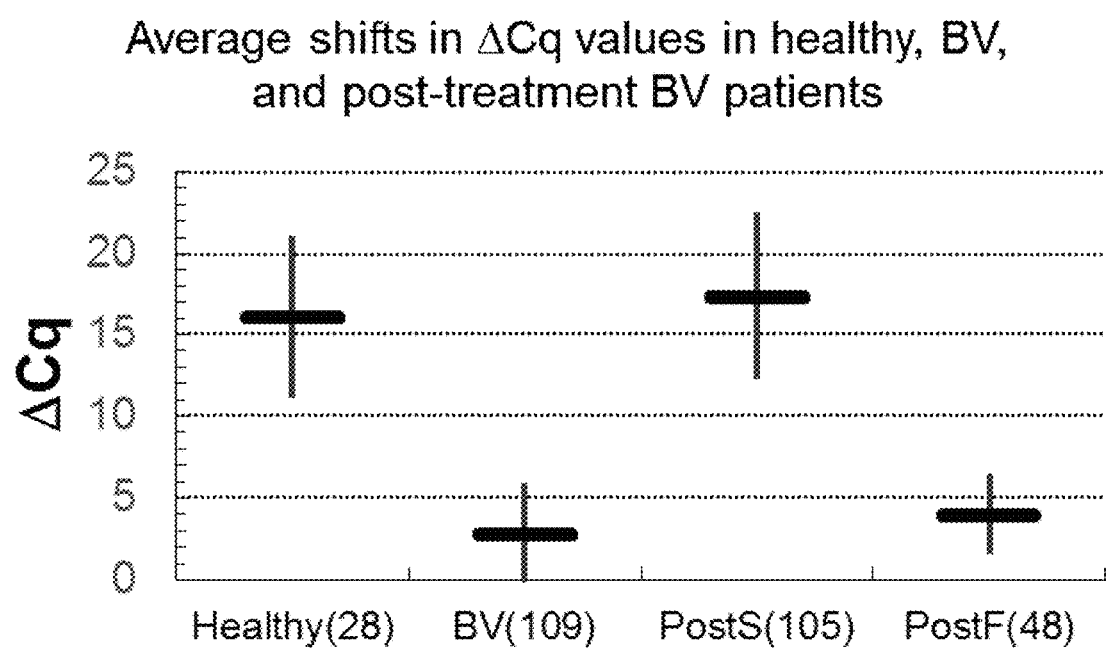
FIG. 17. ΔCq values are diagnostic of acute BV and can monitor the success (S) or failure (F) of treatment. Values (horizontal bars) are averaged over three independent studies spanning five years, of the indicated number of samples in parentheses. Vertical bars indicate the standard deviations.

LbRC has high specificity and sensitivity in classifying samples from known acute BV and healthy patients. ΔCq correctly identified 94% of BV samples and 100% of healthy samples, generating excellent performance metrics. The 6 false negatives may have resulted from the poor "gold" Nugent score standard; these 6 were flagged as moderately atypical from melt curve analysis. FIG. 17 shows that the average ΔCq values for healthy women with no history of BV is ~16. This value drops to an average of ~3 among patients with acute, typically recurrent BV.

Predictive value of LbRC. To a great extent, the problem in treating BV is recurrence; up to 68% of patients recur within one year, notwithstanding that therapy initially restores the patient to normal Nugent and Amsel scores. The described analyses show that the initial visit, after therapy for BV, is critical in patient outcome. After therapy, ΔCq values group these patients fall into two fairly distinct groups (FIG. 17). In the Post-therapy, putatively successful group (PostS), the ΔCq value is about the same as in healthy women, whereas the putatively failed PostF group overlaps the acute BV group. These distinct categories suggest ΔCq is an evaluation of how effective the therapy was, among individual patients. In contrast, almost all patients in both post-therapy groups are normal by Amsel and Nugent criteria.

A set of criteria in addition to ΔCq, to automatically "call" samples as "cured" or "at risk for recurrence" has also been developed (referred to as "combined scores" herein). Combined scores are based primarily on the ΔCq score with a determination of whether there are non-LB melt curves (FIG. 16) present without blocking (higher relative titers) versus only with blocking (lower relative titers).

Figure 18:
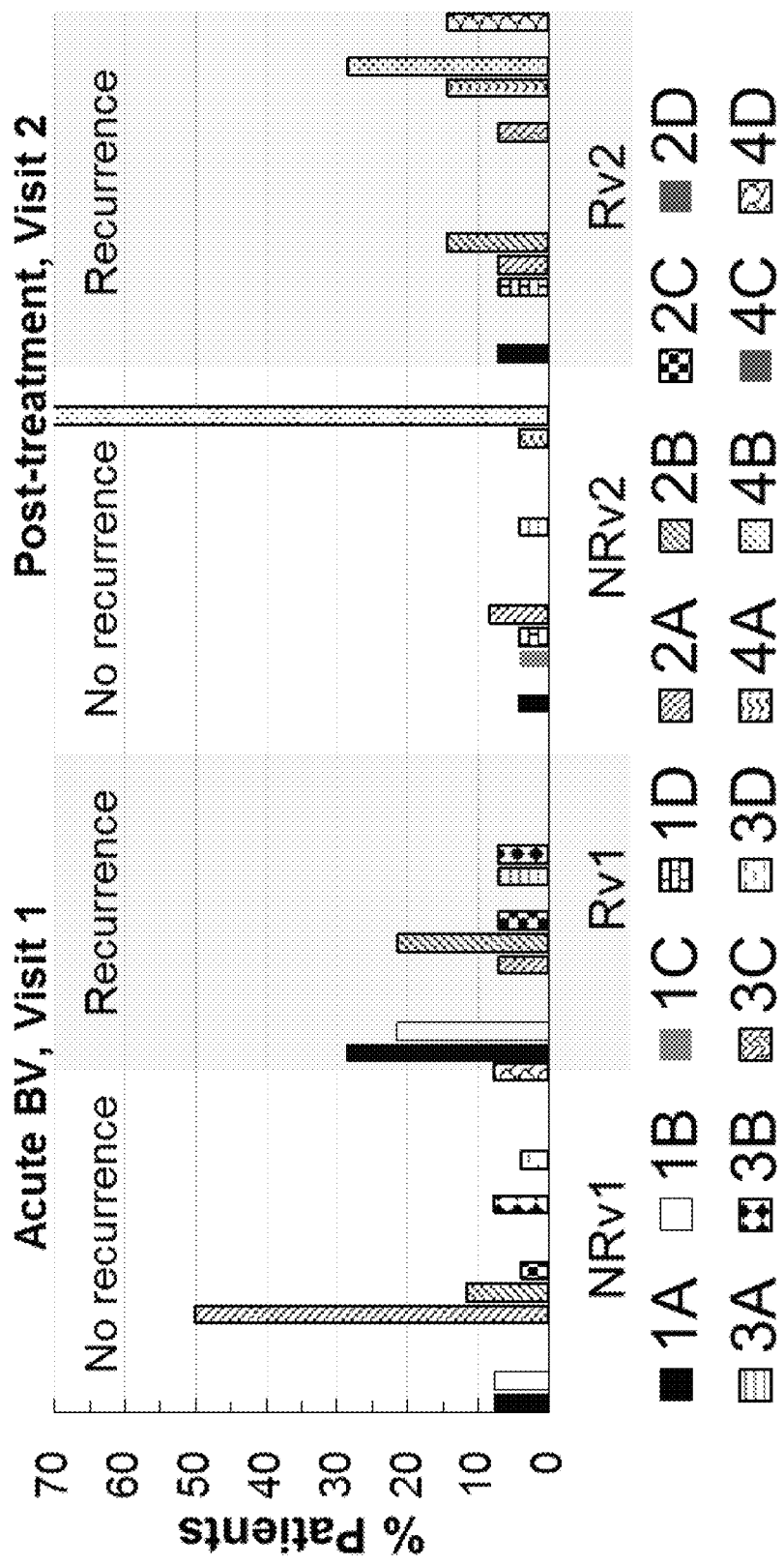
FIG. 18. Prevalence of Combined Scores among BV patients who were non-recurrent (NR) versus eventually recurrent (R), at visits 1 (v1, acute BV) and 2 (v2, post-treatment (PT), normal Nugent and Amsel).

The data shown in FIG. 18 suggests that specific combined scores are strongly associated successful outcomes. Visit 1 (acute BV by Nugent and Amsel) and Visit 2 (post-therapy) samples from 41 patients with histories for recurrent BV were tested. Of these, 26 did not recur and were checked monthly for 3 months, whereas 15 recurred within this time frame. Data show that a score of 2A at visit 1 (BV) was strongly associated with long-term non-recurrence. This score reflects a more moderate level of LB during acute BV, co-dominant with non-LB species (still, however, 0-3 by Nugent scoring). Non-recurrence in the immediate post-therapy visit 2 was strongly associated with combined score 4B, which reflects the highest level of LB with no detectable non-LB even with blocking.

Example 4

Figure 19:
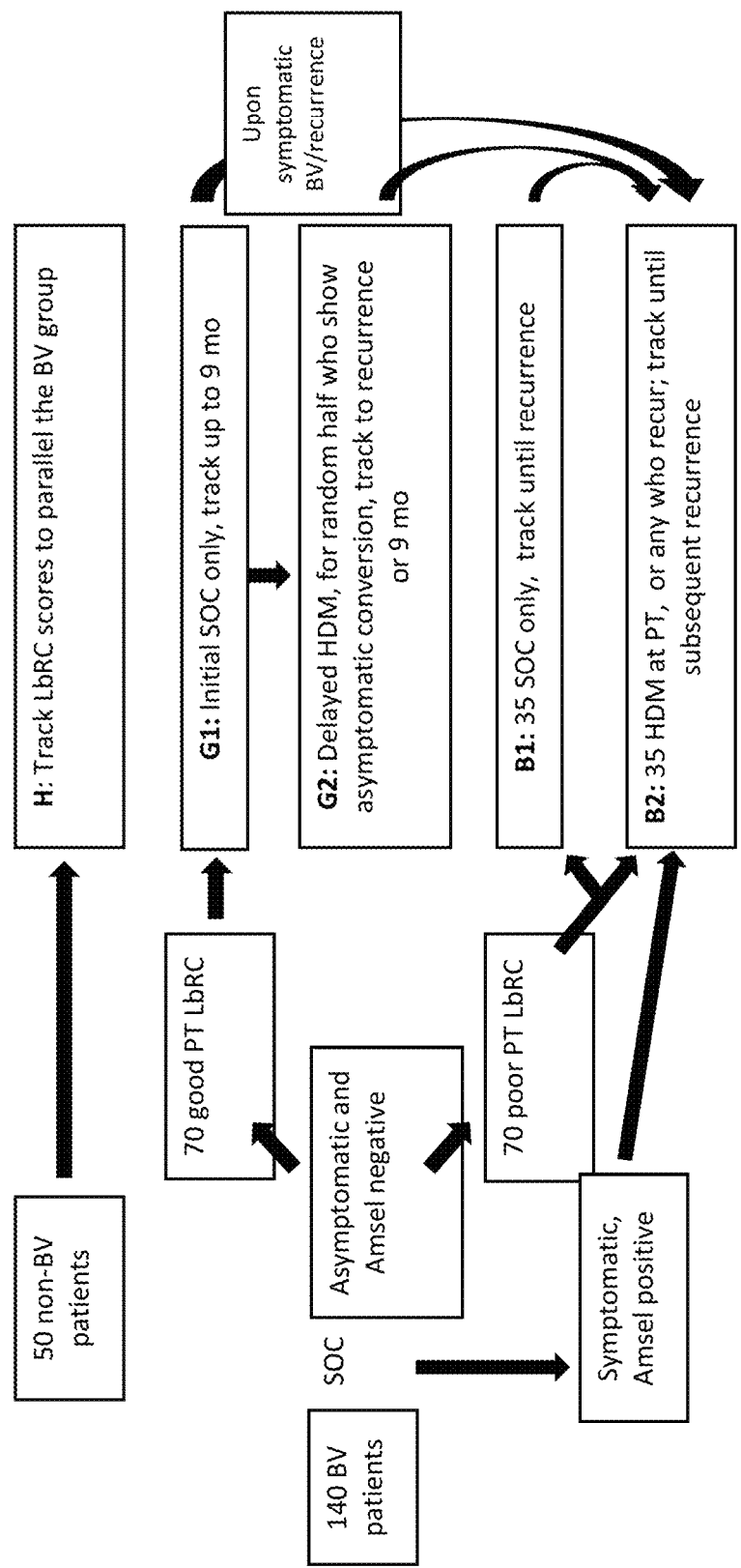
FIG. 19. Prognostics/individualized therapy strategy. Enrollment of BV patients will be based on patient history in the DMC Vaginitis Clinic, 130 per year at 75% recurrence after standard of care (SOC) treatment. Preliminary data indicates 70% non-recurrence among patients with good PT LbRC scores, and 70% recurrence among those with poor PT scores. HDM=high dose metronidazole, 750 mg suppository (Embil).

This Example describes a randomized, prospective study that will enroll at least 50 healthy women and 140 women with acute to recurrent BV (FIG. 19). The first goal of this study is to further validate the systems and methods disclosed herein as a reliable diagnostic of BV, by determining sensitivities and specificities relative to Nugent scores and Amsel criteria of healthy women and BV patients. The second goal is to confirm that empirically determined "poor" LbRC scores of BV patients after treatment are indicators of recurrence, and that preemptive action, based on this score, with more intensive treatment, delays or eliminates recurrence in these patients.

A standard of care (SOC) treatment for BV is oral metronidazole 500 mg twice a day for 7 days. This treatment will be used for all enrollees with BV as the initial treatment. Patients will be evaluated each visit by LbRC scores; a low or poor score indicates that notable levels of non-lactobacilli are present. BV Patients with clinical cures and good LbRC scores will simply be monitored on a monthly basis with no further treatment (Group G1). It is expected that some of these patients will eventually recur, and that LbRC scores will drop two weeks prior resulting in conversion. Half of these (Group G2) will be randomly treated with higher dose metronidazole regimen, HDM, (7) to confirm that the LbRC "warning" prevents recurrence.

Patients who are "cured" by Amsel criteria and Nugent score but not by LbRC will be randomly divided into 2 groups per pre-randomization code. One (B1 Group) will be monitored monthly for up to 9 months for recurrence, with no further treatment in that interval. Another group (B2) will receive a previously tested high dose metronidazole 500 mg vaginal suppository treatment (HDM), and will be monitored for long term recurrence for up to 9 months. The Lab will notify the nurse as to which study number subject needs to be retreated with HDM. The nurse will contact the subject to come in for the medication and instructions on its use. All subjects will be asked to obtain daily vaginal samples, which will be stored at room temperature and returned at the next visit where more supplies will be obtained to continue taking daily specimens for as long as the subject is enrolled and willing to do so.

Fifty non-BV subjects with no history of "vaginitis" in the past year will be enrolled as a control group and seen monthly to monitor the LbRC in the vaginal secretions. All subjects will be asked to take daily dated vaginal samples and store them in supplied containers at room temperature and return the vaginal swabs at each monthly visit where they will receive more supplies for the next month of specimens.

Subjects who relapse with acute symptomatic BV, and randomly half of those who "convert" from a good LbRC score to a poor LbRC score without symptoms, will be offered to take the HDM vaginal suppositories for one time only. Should the subject relapse after taking the HDM vaginal suppositories, she will be dropped from the study and given a prescription for treatment of her BV. Should a subject return with a *trichomonas* infection she will be dropped from the study and treated with a prescription.

Tests at enrollment. All BV patient enrollees will be evaluated at the initial exam and scored for Amsel criteria at their visit for treatment of their vaginal symptoms. Women who score all 4 of the Amsel's criteria (vaginal pH >4.5; positive amine "Whiff" test; ≥20% clue cells; grayish/white adherent discharge, and no mixed infection with trichomoniasis, yeast, Herpes or cervicitis) and a Nugent score of 3 or less, will be diagnosed with BV and will be asked to participate. The swab used for the wet mount/clue cell determination will also be used to check pH and make the slide for gram stain and Nugent score.

Once consent and HIPAA forms are signed the subject will have replicate vaginal swabs taken. One will be processed for LbRC and targeted qPCR assays. The second will be tested using the BD Affirm VIII and gram stained for a Nugent scored. The third swab will be tested using commercial BV Blue kits.

Treatment at enrollment. If an enrollee is diagnosed with BV, she will receive the SOC treatment (oral metronidazole 500 mg twice a day for 7 days) and an appointment for a PT visit 3-7 days after treatment. She will receive supplies and instructions for daily self-swabs during this interval.

Visit 2. At this PT visit, all subjects will be asked if she is symptomatic for any vaginal/vulvar symptoms. If she is symptomatic, she will have an examination and evaluated by Amsel criteria and microscopy for BV, yeast and *trichomonas*. Three extra vaginal swabs will be obtained for the same tests as the initial visit. If she still has BV (≥3 Amsel criteria), she will receive a complete vaginal examination, and placed into Group B2 to receive more aggressive treatment (HDM). If the subject is asymptomatic, she will provide two swabs to the research nurse who will evaluate her Amsel's criteria. If she has <3 of the Amsel's criteria (normal), she will be assigned to a Group based on LbRC scores (FIG. 20) which will be obtained within 7 days of sampling. These patients will be given supplies and instructions on taking a daily vaginal swab (except during heavy menses) and an appointment to return in one month with the obtained swabs. Subjects will be notified by telephone to come to pick up the HDM suppositories, or they may be mailed, if they are randomized into the treatment Group G2.

All subjects will be followed up to 9 months as long as they are willing to obtain the daily specimens, return monthly for evaluation and have not been dropped from the study. The study visits 3-11 will be as visit 2. Subjects who relapse with BV and have not yet been treated with the HDM suppositories, will be offered treatment with the HDM suppositories and may remain in the study for a total of 9 months if desired. Women who develop a symptomatic vaginal yeast infection at any visit will have an examination and will be treated with a prescription for an anti-yeast medication. These women who have a vaginal yeast infection will remain in the study. Daily swabs will not be taken during heavy menses, but should be obtained if the subject is spotting.

Healthy control Group H. If a woman does not have a history of any vaginal infections or vaginal/cervical cancer within the past year, and is negative for 3 of the 4 Amsel's criteria, and wishes to enroll to obtain daily vaginal swab specimens, she will be placed into Group H. Once she has signed consent, she will provide the study nurse with 3 self obtained vaginal samples. One swab will be used for evaluation of Amsel's criteria and microscopic examination and the second swab will be used for LbRC testing and the third swab will be for the Affirm VPIII test. She will be given supplies and instructions for daily self-swabbing. She will return monthly for two self-swab evaluation of Amsel's criteria, Gram Stain and LbRC evaluation and to return the obtained swabs and pick up new supplies for as long as she is willing to do so, up to 9 months. As long as she does not experience any vaginal symptoms, she may continue in the study. If any subject does experience vaginal symptoms, she will return for an unscheduled visit within 2-3 days.

Group G1 patients. If a BV patient is not diagnosed with BV at her PT visit, and if her LbRC test result is "good" (hyperdominant for lactobacilli) she will be assigned to Group G1. She will not be given further treatment at the time. Instead, she will be given supplies and instructions for daily self-swabbing, and especially for the 3 sequential days after each menses. If she does not experience any symptoms, she will return every month for up to 9 months to return her previous month's swabs, and to provide two self-swabs on site, for wet mount, pH, Nugent, and amine tests and LbRC evaluation to confirm that she remains BV-negative. If she does experience symptoms, she will return for an unscheduled visit within 2-3 days and will have an examination to determine the cause of her symptoms and the necessity to retreat with HDM suppositories and be placed into Group B2 and continue in the study for up to 9 months if desired. She will be given supplies and instructions for self-swabbing each day during the treatment, and scheduled for a follow-up visit within 3-5 days of treatment. This follow-up visit will be handled as described for the initial PT visit. If she is BV-negative, she will get no further treatment at the time, but will be given samples and instructions for daily self-swabbing, especially the 3 sequential days after each menses, and will return every month for up to 9 months for an exam to confirm that she remains BV-negative.

Group G2 patients. Patients who are about to recur after treatment show poor LbRC scores weeks before becoming symptomatic. Randomly, half of Group G1 patients who convert will be placed into Group G2, and receive HDM therapy to determine if this prevents symptomatic recurrence. These patients will come in for an exam upon notification of this status to confirm conversion and to get Amsel's criteria and Nugent scores. They will then be followed as described for Group B2 patients below.

Group B1 patients. If a BV patient is not diagnosed with BV at her PT visit but her LbRC score is nevertheless not "good" (notable presence of non-lactobacilli), she will be randomly assigned to either Group B1 or eventually B2. If she is placed in B1, she will not be given further treatment at the time. Instead, she will be given supplies and instructions for daily self-swabbing, and especially for the 3 sequential days after each menses. If she does not experience any symptoms, she will return every month for up to 9 months for a self swab evaluation to confirm that she remains BV-negative. If she does experience symptoms, she will return for an unscheduled visit within 2-3 days for an examination to determine the cause of her symptoms and the necessity to retreat with HDM suppositories and placed into Group B2 and be continued into the study if desired. She will be given supplies and instructions for self-swabbing each day during the treatment, and scheduled for a follow-up visit within 3-5 days of treatment. This follow-up visit will be handled as described for the initial PT visit. If she is BV-negative, she will get no further treatment at the time, but will be given samples and instructions for daily self-swabbing, especially the 3 sequential days after each menses, and will return every month for up to 9 months for an exam to confirm that she remains BV-negative.

Group B2 patients. Half of the asymptomatic patients with poor LbRC scores at visit 2, and all patients who become symptomatic with BV during the study period, will be placed into Group B2. The patients will receive high dose metronidazole, HDM (750 mg suppositories, one per day for 7 days). The HDM suppositories will be supplied to the subjects without cost to them. Since the risk of metronidazole's interaction with alcohol may continue with the 7 day vaginal therapy, the use of alcohol is not recommended within 48 hours of taking metronidazole. They will be given supplies and instructions for self-swabbing during this period, just before inserting the nightly suppository. Within 3-7 days of the end of treatment, they will return to the clinic for Visit 3. If they are still symptomatic, they will be dropped from the study and given alternative therapy. If they have become asymptomatic, they will be followed by daily self-swabs and monthly visits as described for the other groups.

Unscheduled Visits. At this symptomatic unscheduled visit, subjects from any group will have the SOC vaginal examination and laboratory tests done to determine if any vaginitis is present, in addition, two extra vaginal swabs will be obtained, one for Gram stain and one for PCR analysis. If the subject has a yeast infection caused by the metronidazole, the subject may continue in the study and will be treated with a prescription for an antifungal medication. If the subject has a relapse of her BV infection and has not yet received the HDM suppositories, she will be transferred to Group B2 to receive HDM, and continue in the study with daily vaginal swab samples to be obtained and monthly visit for a self vaginal swab evaluation and to replenish her supplies. Duration of self swabs will be for a total of 9 months as long as the subject is willing. If she has a relapse of her BV at anytime after taking the HDM suppositories, she will be dropped from the study and treated with a prescription for an alternative medication.

Treatment Protocols for patients diagnosed with BV at the enrollment visit. All women diagnosed with BV with 4 out of 4 of the Amsel criteria will receive oral metronidazole 500 mg (14 tablets) to be taken twice a day for 7 days, once informed consent has been signed. In addition the extra swabs for the study will be taken after consent and HIPAA has been signed. Subjects will be asked to self-swab daily during this interval between enrollment and Visit 2.

Vaginal examinations. SOC vaginal examination for vaginitis at enrollment and subsequent scheduled and unscheduled visits consists of the following tests: visual examination of the vulva and vagina; speculum examination of the vagina and cervix; and vaginal secretion swabs obtained for wet mount and KOH microscopic examination, pH, amine test and yeast culture. In addition 2 extra swabs will be taken for LbRC and Gram Stain for the study.

Study swab reviews consist of the subject obtaining 2 vaginal swab samples (at the clinic) that will be evaluated for Amsel's criteria, trichomonas, Gram Stain and LbRC evaluation. This will determine if she is normal (and continues on in the study) or needs treatment for some form of vaginitis (where depending on the vaginitis found, may need to be dropped from the study).

Inclusion Criteria For BV Subjects: (140 subjects): premenopausal women over the age of 18 who have BV; who are willing to sign informed consent; subject is willing to refrain from using any vaginal medications, douches or spermicides except for the metronidazole suppositories that are given to her for the duration of the study; subject is willing to use condoms when sexually active and willing not to have sexual intercourse within 48 hours of any Study Visit; subject will refrain from alcohol for 24 hours prior to the first 7 days of the metronidazole treatment and for 48 hours after completion of this treatment; enrollees for the healthy Group H in the study must be premenopausal and have not experienced any vaginitis in the past year; have a self swab evaluation that is normal (no yeast, no clue cells, normal flora, no parabasal cells and no trichomonads); and willing to obtain daily samples and return monthly with the samples for a self swab evaluation and a replenishment of the daily swab supplies. Healthy women will continue for as long as they are willing up to 9 months. Healthy women will be asked to use supplied non-lubricated condoms, but will not be dropped from the study if they do not.

Exclusion Criteria: mixed vaginal infection at time of enrollment; pregnancy, nursing or planning on getting pregnant; subject on anticoagulation therapy, lithium therapy or Antabuse therapy; vaginal bleeding at time of enrollment; use of any vaginal antibiotics or antifungals in the previous 10 days, from enrollment.

Study EndPoints: Cure is defined as Gram Stain Nugent Score of 1-3 and resolution of clinical symptoms. Partial cure is defined as Asymptomatic and Gram Stain Nugent Score of 4-6. Failure is defined as Nugent Score of 7-10 on Gram Stain, regardless of presence or absence of symptoms. Normal is defined as Gram Stain Nugent Score of 1-3.

The results will demonstrate the efficacy of the systems and methods disclosed herein.

Example 5

Prognosis. Without being bound by theory, Example 5 will confirm that inadequate eradication of BV-associated species after therapy is a major cause of rapid recurrence, and 2, that sub-dominant species are responsible for the decline of LB at conversion, acting in concert with menses, facilitating the subsequent rise of dominant BV-associated aerobes. The aim of Example 5 is to correlate optimized output parameters of LbRC with time to recurrence and other clinical determinants in BV patients, provisionally focusing on post-treatment (PT) samples taken at the conclusion of therapy, and at conversion before symptomatic BV develops.

Figure 20:
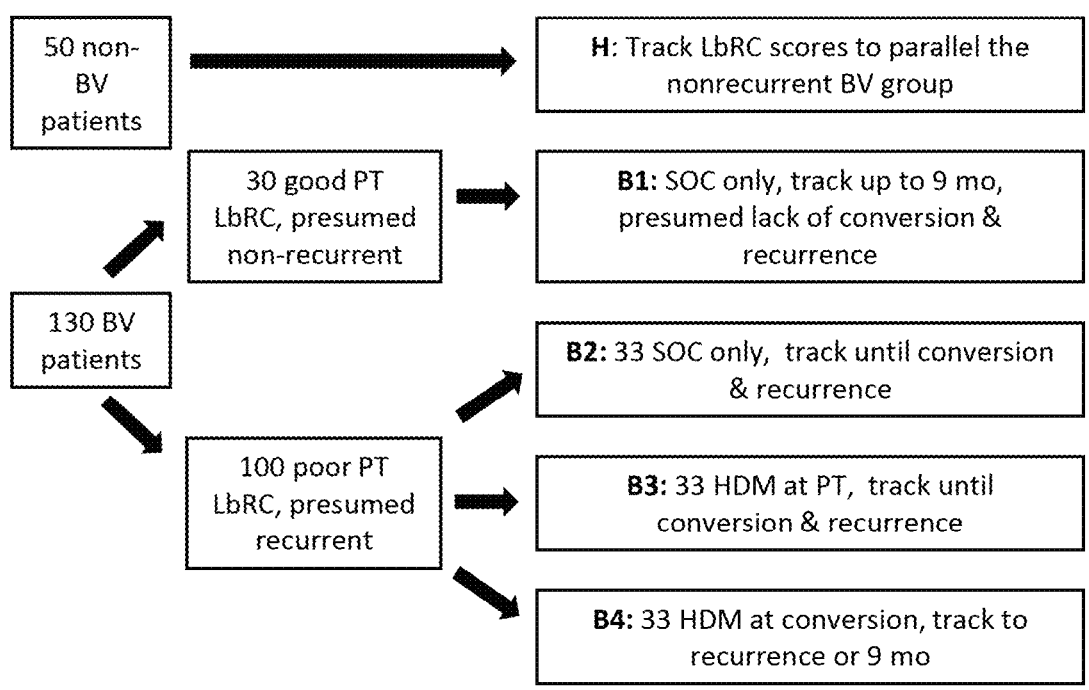
FIG. 20. Patient strategy. Enrollment of BV patients will be based on patient history in the DMC Vaginitis Clinic, 130 per year at 75% recurrence after SOC treatment. Preliminary data indicate 70% non-recurrence among patients with good PT LbRC scores, and 70% recurrence among those with poor PT scores. HDM=high dose metronidazole.

130 recurrent BV patients will be enrolled (FIG. 20). These patients will be treated at diagnosis (Nugent and Amsel) with SOC 500 mg oral metronidazole twice daily for 7 days, at seen again at day 10 (PT). LbRC analysis will be performed for diagnostic determinations as described elsewhere herein. It is anticipated (historically and from preliminary data) that 30 PT samples will have good scores indicative of non-recurrence (B1). The 100 patients with poor PT scores will be divided into 3 groups: B2 patients will get no further therapy until and unless BV recurs; B3 will get high dose metronidazole (HDM) therapy (750 mg metronidazole suppository daily for 7 days); B4 will get this therapy if and when they show conversion ($2^{nd}$-$4^{th}$ day of poor LbRC scores to define conversion, predicted to occur after menses). All BV patients will self-swab daily and bring stabilized swabs into their monthly clinic visits. Healthy patients will be sampled in the clinic twice to get Nugent and Amsel scores, and will self-swab in the same manner. B2 patients, the most likely to recur, will get a smaller number of Dacron swabs for use before/during menses, to suspend in Port-A-Cul medium, to preserve and maintain viable populations of anaerobes.

Previously described LbRC methods will be employed. An additional assay can also be performed. This assay, like LbRC requiring no manipulation post-qPCR, identifies the dominant or co-dominant species of LB (*L. iners, L. crispatus, L. jensenii*) by melt-curve analysis of an amplicon that spans the internal transcribed spacer between ribosomal RNA genes. Even though *L. iners* is common among healthy women, dominance of *L. iners* is a strong risk factor for BV. Indeed, RBV patients can be almost exclusively dominated by *L. iners*. Therefore, coupling the information that a patient's sample is predominantly *L. iners* with a poor LbRC score may increase predictive value. Alternatively, the simpler qPCR test for *L. iners* may be implemented, testing both acute BV and PT samples. Other add-on assays that might supplement the increase prognostic value of LbRC include a culture-independent virulence genotyping of *G. vaginalis*.

Statistics. The significance of the PT LbRC score (B1 vs. B2), and of intervention at PT (B2 vs. B3) or at conversion (B2 vs. B4) will be determined using Fisher's exact test for comparing categorical scores (% recurrence defined at discrete intervals), or using Wilcoxon signed-rank test in comparing time-to-recurrence, both performed using Stata Statistics software V.11. Time-to-recurrence in the various arms will be reported as Kaplan-Meier plots, and plots will be compared using the log-rank test.

The following results are anticipated: (i) a diagnostic odds ratio >10 for predicting recurrence at PT and at conversion, (ii) clear indications (P<0.05) that LbRC-directed intervention with more therapy improves outcome; (iii) a decrease in recurrence rates of 50%, and/or (iv) a doubling of the time-to-recurrence.

Causation. Without being bound by theory, it is believed that species present just before conversion facilitate the decline in LB and broad changes that define conversion, which then results in BV. LbRC will be used to identify pre-conversion samples in the B2 group, the most likely to convert. These samples, directly and pure cultures derived from them, will be assayed for their ability to antagonize LB species/strains, or to promote growth of BV-associated species, or to convert vaginal aliquots from healthy versus post-therapy BV patients, using agar-based assays and broth competition assays. LbRC enables high-throughput characterizations of the competition assays. The significance of positive findings is that converting species may be inadequately affected by standard BV therapies and thus drive recurrence, so their identification may enable targeted therapy.

Assay for "conversion abilities" of single colonies and pre-conversion vaginal samples to inhibit LB or promote BV-associated anaerobes. Without being bound by theory, it is believed that subdominant species or synergistic groups either rise in titer or induce expression of pathways just before conversion, which convert the vaginal microbiome from a healthy to a BV-promoting profile. In these assays, both single colonies isolated from pre-conversion samples (Portas identified by LbRC, mixtures of these, and patient-paired aliquots from pre-conversion versus control samples, will be grown in static broth cultures in anaerobic jars, or on plates using a serum-based media). A species (or mixture) contributing to conversion will create a zone of inhibition when spotted onto and co-incubated with vaginal LB lawns, but no zone on BV-associated anaerobe lawns. In broth (96 deep well plates), such a species will convert an initially high LB culture to low titer, relative to the competing species, readily assayed with LbRC. This conversion capability will be tested at both normal vaginal pH (4.2) and BV-associated pH (5.5), and in the presence and absence of blood. Conversions may depend on synergistic actions of multiple species, in which case single colonies will not convert, but the pre-conversion sample will convert. In this case, combinations of recovered species will be tested. These experiments are modelled on existing data in which β-hemolytic enterococci cultured from RBV samples, directly inhibited pure cultures of vaginal lactobacilli, in broth and plate assays, but did not inhibit *G. vaginalis*.

Collectively, the results will show that poor LbRC scores PT predict poor outcome (rapid recurrence) and good LbRC scores predict cure or longer-term non-recurrence, 2: that conversions precede and predict recurrent episodes of acute BV, and 3: that therapy directed by LbRC at these two events will improve outcome (delayed or no recurrence). The results will also demonstrate the importance of *L. iners, G. vaginalis, Prevotella, P. timonensis*, BVAB2, *Mycoplasma* sp., *E. faecalis* and/or *A. vaginae* in the conversion process.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability to accurately diagnose or predict a condition associated with a perturbed bacterial population within a microbiome, such as a vaginal microbiome.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents and/or patent applications (collectively "references") throughout this specification. Each of the cited references are individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

TABLE 1B

| Primer | Sequence | SEQ ID NO: |
|---|---|---|
| BU4F+ | CTCCTACGGGAGGCAGCA | 1 |
|  | CTCCTACGGGAGGCTGCA | 2 |
|  | CCCTACGGGGGGCAGCA | 3 |
|  | CACCTACGGGTGGCAGCA | 4 |
| BU6R+ | GACTACAGGGGTATCTAATCC | 5 |
|  | GACTACCAGGGGTATCTAATCC | 6 |
|  | GACTACCGGGGTATCTAATCC | 7 |
|  | GACTACCCGGGTATYTAATCCGG |  |
|  | GGACTACTAGGGTATCTAATCCT | 9 |
|  | GACTACCRGGGTATCTAAKCCTG | 10 |
| 1492R | ACCTTGTTACGACTT | 11 |
| 27F | GCCTTGCCAGCCCGCTCAGTCAGA GTTTGATCCTGGCTCAG | 12 |
| 338R | GCCTCCCTCGCGCCATCAGNNNN NNNCATGCTGCCTCCCGTAGGAGT | 13; the 8 Ns represent a barcode within primer 338R |
| 534R | CCTACGGGAGGCAGCAG | 14 |
| 338F | ACTCCTRCGGGAGGCAGCAG | 15 |
| 806R | GGACTACCVGGGTATCTAAT | 16 |

TABLE 1A

Percentage of RDP database entries with perfect complementarity to broad-spectrum primers used in vaginal studies

| Target | 8F+ | 27F | BU4F+ | 338F/R | 341F | BU6R+ | 534R | 806R | 1501 R1&2 | 1492R |
|---|---|---|---|---|---|---|---|---|---|---|
| Bacteria | 83 | 48 | 95 | 93 | 91 | 93 | 85 | 86 | 100 | 78 |
| Actinobacteria | 82 | 63 | 97 | 97 | 93 | 97 | 86 | 86 | 100 | 87 |
| Aquificae | 90 | 88 | 97 | 5 | 97 | 95 | 65 | 67 | 100 | 57 |
| Bacteroidetes | 81 | 24 | 96 | 96 | 5 | 96 | 96 | 95 | 100 | 84 |
| Caldiserica | 100 | 100 | 97 | 97 | 97 | 96 | 97 | 94 | n.a. | n.a. |
| Chlamydiae | 82 | 0 | 71 | 0 | 97 | 95 | 0 | 95 | 13 | 6 |
| Chlorobi | 70 | 53 | 95 | 94 | 1 | 96 | 1 | 96 | 100 | 95 |
| Chloroflexi | 78 | 55 | 84 | 77 | 95 | 32 | 60 | 96 | 87 | 28 |
| Chrysiogenetes | 100 | 100 | 91 | 91 | 77 | 100 | 17 | 32 | 100 | 100 |
| Deferribacteres | 100 | 67 | 99 | 98 | 91 | 96 | 100 | 100 | 100 | 93 |
| Deinococcus-Thermus | 83 | 64 | 97 | 97 | 99 | 97 | 99 | 93 | 84 | 2 |
| Dictyoglomi | n.a. | n.a. | 100 | 100 | 97 | 100 | 97 | 98 | n.a. | n.a. |
| Elusi-microbia | 75 | 25 | 94 | 93 | 100 | 94 | 0 | 100 | n.a. | n.a. |
| Fibrobacteres | 86 | 86 | 93 | 93 | 94 | 95 | 68 | 95 | 100 | 80 |
| Fusobacteria | 86 | 81 | 95 | 95 | 94 | 97 | 98 | 95 | 50 | 0 |
| Gemmatimonadetes | 55 | 41 | 98 | 98 | 95 | 91 | 97 | 98 | 100 | 88 |
| Lentisphaerae | 88 | 63 | 95 | 0 | 98 | 95 | 95 | 92 | 33 | 25 |
| Nitrospira | 35 | 16 | 97 | 97 | 0 | 95 | 84 | 93 | 100 | 89 |
| Planctomycetes | 63 | 42 | 41 | 1 | 97 | 94 | 53 | 95 | 100 | 84 |
| Proteobacteria | 85 | 40 | 98 | 97 | 1 | 94 | 44 | 91 | 100 | 81 |
| Spirochaetes | 80 | 40 | 91 | 91 | 98 | 91 | 96 | 94 | 100 | 83 |
| Synergistetes | 67 | 51 | 99 | 99 | 91 | 92 | 17 | 80 | 100 | 86 |
| Tenericutes | 90 | 83 | 95 | 95 | 99 | 92 | 81 | 93 | 9 | 0 |
| Thermodesulfobacteria | 67 | 0 | 96 | 96 | 95 | 99 | 80 | 76 | n.a. | n.a. |
| Thermotogae | 11 | 4 | 97 | 97 | 96 | 90 | 92 | 100 | 100 | 38 |
| BRC1 | 100 | 0 | 18 | 18 | 97 | 98 | 50 | 94 | n.a. | n.a. |
| OD1 | 50 | 50 | 46 | 0 | 18 | 21 | 89 | 98 | n.a. | n.a. |
| OP11 | n.a. | n.a. | 86 | 5 | 0 | 0 | 0 | 10 | n.a. | n.a. |
| SR1 | n.a. | n.a. | 97 | 95 | 0 | 97 | 31 | 0 | n.a. | n.a. |
| TM7 | 76 | 38 | 98 | 97 | 95 | 87 | 99 | 97 | 100 | 0 |
| WS3 | 50 | 0 | 95 | 95 | 97 | 97 | 0 | 80 | 100 | 80 |
| Armatimonadetes | 71 | 46 | 28 | 5 | 96 | 92 | 78 | 97 | 67 | 58 |
| Verrucomicrobia | 72 | 46 | 98 | 0 | 4 | 93 | 84 | 89 | 100 | 71 |
| Acidobacteria | 57 | 40 | 97 | 97 | 0 | 95 | 77 | 47 | 100 | 20 |
| Firmicutes | 84 | 61 | 96 | 96 | 97 | 97 | 94 | 95 | 100 | 90 |
| Cyanobacteria/Chloroplast | 69 | 60 | 93 | 93 | 96 | 91 | 94 | 95 | 100 | 95 |

Numbers are percentages of "good" quality reads >1200 bp on RDP Release 10, Update 29 (1), with perfect complementarity to each specified primer, except 27F (~8F) and 1492R/1501R1&2. Since these primers are near the ends of 16SrDNA, and not in most database entries, they were evaluated as % matches among only those entries containing bases in end positions. Comparisons are appropriate between columns within boxes; percentages in bold indicate phyla covered by primers in this study as well or better than published primers. Black highlights phyla that are largely excluded by the indicated primers. n.a. = not applicable since there were none or only 1 representative in the database. Primer 338 is used as both Forward or Reverse primer in the indicated studies.

TABLE 2

Primers useful for amplifying *Lactobacillus* and non-*Lactobacillus* species in vaginal samples.

| Name | Sequence | SEQ ID NO. |
|---|---|---|
| Forward Primer(s) | | |
| BU4L | CTCCTACGGGAGGCAGCA | 21 |
| LB-blocker3 | EEOFGCAGTAGGGAATCTZOOFZZT | 22 |
| LBB3p | GGCAGCAGTAGGGAATCTTCCAT | 23 |
| 8FM | AGAGTTTGATCMTGGCTCAG | 24 |
| 8F1 | AGAGTTTGATCCTGGCTTAG | 25 |
| 8F2 | AGGGTYCGATYCTGGCTCAG | 26 |
| 8F3 | AGAATTTGATCTTGGTTCAG | 27 |
| 8F4 | AGAGTTTGATCCTGGCTCAMG | 28 |
| 8FX | GASTTTGATYMTGGCTCAG | 29 |
| LB-L3 | GGAGGCAGCAGTAGGGAATCTTCCA | 30 |
| Actino-L8i | CIIIGACGGGTAGCCGGCC | 31 |
| Actino-L8g | CGGGGACGGGTAGCCGGCC | 32 |
| Corio-L3H | GGGTTGAGAGACCGACCGGCCTGA GAGGGCGATC | 33 |
| Mobil-135L | GGCTGCTAATACTGGATATTCAGGC | 35 |
| BrdF | TCCTACGGGAGGCAGTRA | 36 |
| Fuso-L5 | CCAGCAATTCTGTGTGCAC | 37 |
| Fuso-L6 | CCAGCAATTCTGTGTGTGT | 38 |
| Lachno-LM | GTAAAGCTCTATCAGMAGGGAAGA | 39 |
| BVAB2/3-L1 | 5'GCGAAAGCCTGACCCAGCA | 40 |
| ClosL-445a-1 | CSACGATGCGTAGCCGACCT | 41 |
| ClosL-445a-2 | CGACGATCAGTAGCCGACCT | 42 |
| ClosL-445a-3 | CAACGATCAGTAGCCGGTCT | 43 |
| Clos-XIIIF | GGGATAGCCACYGGAAACGG | 44 |
| Peptos-FL | GAGGAAGCCCCGGCTAACTAC | 45 |
| Mega+L444 | GCGAYGATCAGTAGCCGGTC | 46 |
| SSL455 | CRTAGCCGACCTGAGAGGG | 47 |
| SSL454 | ATAGCCGACCTGAGAGGG | 48 |
| BProL8-41-2 | AYTGACGYTCATGCACGAAA | 49 |
| GPro-L154a | GTAATGCCTAGGAATCTGCCTG | 50 |
| GPro-L154b | GTAATGCCTGGGAAATTGCCCG | 51 |
| GPro-L154c | GTAATGTCTGGGAAACTGCC | 52 |
| GPro-L154d | GTAATGCCTGGGAATCTGGCTT | 53 |
| GPro-L154e | GGGAYAACTTGGGGAAACTCAA | 54 |
| Myco-F1a | CGAAGGCGCCAACTTGGACTAT | 55 |
| Myco-F1b | GAAGGCGARAACTTAGRSCATT | 56 |
| Myco-F1c | GCGAAGGCAGCTTACTGGGTYTAT | 57 |
| Reverse Primer(s) | | |
| BU6R | GACTACCAGGGTATCTAATCC | 58 |
| LB-blocker4 | EZZOGCTACCCATGCTTTCGAGOO ZOZZT | 59 |
| LBB4p | GTTCGCTACCCATGCTTTCGAGCC TCT | 60 |
| 1501R | TACGGYTACCTTGTTACGACTT | 61 |
| 1501-1 | WACRGYTACCTTGTTACGAC | 62 |
| 1501-2 | TAYGGMTACCTTGTTACGAC | 63 |
| LB-R6 | GTTCGCTACCCATGCTTTCGAGCCTC | 64 |
| Actino-R3 | ACCTTCCTCCGAGTTRACC | 65 |
| Corio-R4H | GATTACTAGCAACTCCGACTT | 66 |
| Mobil-549R | CACCGCAGACCAACAGTTAAGCTGC | 67 |
| BrdRa | CCYRGGTAAGGTTCCTCGCGTATCA | 68 |
| BrdRb | CCYTGGTAAGGTTCCTCGCGTATCA | 69 |
| Fuso-R6 | CCCAGGCGGATYACTTATC | 70 |
| Lachno-R3 | CATTMTTGCGAACGTACTCC | 71 |
| BVAB2/3-R1 | GGGTCGATACCTCCTACASCT | 72 |
| Clos-R698 | GGCACRTAGTTAGCCGGGGCT | 73 |
| ClosXI-XIIR | GAGTTTCACACTTGCGTGCG | 74 |
| Clos-XIR | GAGTTTCATGCTTGCGCACG | 75 |
| Peptos-FR | GGTAACCYCCGACACCTARTACTC | 76 |
| Mega-R870 | GGAATTCCRCTTTCCTCTCCGATA | 77 |
| Staph-R955 | GATCCCCACGCTTTCGCACA | 78 |
| Strep-R860 | GGCACTRARYCCCGGAAAGG | 79 |
| BProR-1085-2 | CATCGATTAAWCCACATMA | 80 |
| GPro-R970a | GCGTTAGCTCCRGAAGCCAC | 81 |
| GPro-R970b | CACGTTAGCTWCGGGCACC | 82 |
| GPro-R970c | GTTAGCTGCGCCACTAAGA | 83 |
| GPro-R970d | CTGCGCCACTAAYCWCATTCATA | 84 |
| MycoRa | GCTCCATGTCRCCATATTGCTT | 85 |
| MycoRb | GCTTCATCTTACGATTTTGCAG | 86 |
| MycoRc | GTCACTTTTACAAGTTGGCTA | 87 |

TABLE 3A

| | | | | | Acute BV PBN-qPCR | | |
|---|---|---|---|---|---|---|---|
| | | Forward Name | Reverse Name | | | Acute BV PB-qPCR | |
| | Target | (mM) | (mM) | PCR Program** | Cells/sample | ID Uncloned | ID Clones |
| Broad | Broad-spectrum | BU4L (0.4) | BU6R (0.4) | 40X (30s 30s 30s @ 94° C. 58° C. 72° C.) | 5.4E+09 | n.a. | See Acute BV 16S-C&S |
| non-*Lacto-bacillus* | Blocked Broad-spectrum (*Lacto-bacillaceae*) | BU4L (0.1) LB blocker3 (0.7) LBB3p (2.5) | BU6R (0.1) LB blocker4 (0.7) LBB4p (2.5) | 45X (30s 30s 30s 30s @ 95° C. 74° C. 58° C. 72° C.) | n.a. | n.a. | n.a. |
| Broad for nested PCR | Broad-spectrum nested | 8FM (0.3) | 1501R (0.3) | 24X-40X (30s 30s 90s @ 94 C. 54 C. 72 C.) | n.a. | n.a. | n.a. |
| Broad for nested PCR (enhanced) | Broad-spectrum nested | 8F1 8F2 8F3 8F4 8FX (0.3) | 1501-1 1501-2 (0.3) | 24X-40X (30s 30s 90s @ 94 C. 54 C. 72 C.) | n.a. | n.a. | n.a |
| *Firmi-cute* | *Lacto-bacillaceae* | LB-L3 (0.3) | LB-R6 (0.3) | 40X (30s 60s @ 94° C. 4° C.) | 5.0E+08 | *Lactobacillus iners* | n.a. |
| *Actino-bacteria* | *Actino-bacteridae* | ActinoL8i 0.01 L8g (0.3) | ActinoR3 (0.3) | 40X (30s 30s 45s @ 94° C. 62° C. 72° C.) | 8.7E+08 | *Gardnerella vaginalis* | n.a. |

TABLE 3A-continued

Acute BV PBN-qPCR

| | Target | Forward Name (mM) | Reverse Name (mM) | PCR Program** | Acute BV PB-qPCR | | |
|---|---|---|---|---|---|---|---|
| | | | | | Cells/sample | ID Uncloned | ID Clones |
| | Corio-bacteridae | Corio-L3H (0.6) | Corio-R4H (0.6) | 40X (30s 90s @ 94° C. 2° C.) | 2.3E+07 | *Atopobium vaginae* | n.a. |
| | Mobi-luncus | Mobi135L (0.3) | Mobi549R (0.3) | 40X (30s 30s 30s @ 94° C. 62° C. 72° C.) | 2.6E+05 | *Mobiluncus curtisii* | n.a. |
| Bacter-oides | Bacter-oidaceae/uc Prevotellaceae | BrdF (0.3) | BrdRa BrdRb (0.3) | 40X (30s 30s 60s @ 94° C. 68° C. 72° C.) | 3.8E+07 | *Prevotella bivia* | n.a. |
| Fuso-bacteria | Fuso-bacterium | Fuso-L5,L6 (0.2) | Fuso-R6 (0.2) | 45X (30s 30s 30s @ 94° C. 61° C. 72° C.) | 4.5E+07 | *Leptotrichia amnionii* | n.a. |
| Firmi-cute | Lachno-spiracea uc & incertae sedis, Clostridium IVa, Roseburia | Lachno-LM (0.3) | Lachno-R3 (0.3) | 45X (30s 30s 45s @ 94° C. 64° C. 72° C.) | 6.3E+08 | ~uc Lachnospiraceae (~Shuttleworthia [0.93]) | 100% uc Lachnospiraceae (~Shuttleworthia [0.93]) (16 clones) |
| | uc Clostridiales (BVAB2&3 subset) | BYAB2/3-L1 (0.1) | BVAB2/3-R1 (0.1) | 40X (30s 75s @ 94° C. 8° C.) | 1.7E+04 | *Dialister* sp. | n.a. |
| | Cross-family Clostridia | ClosL445a (0.1) | ClosR698 (0.3) | 40X (30s 60s @ 94° C. 4° C.) | 3.9E+03 | mixed | 60% *Ruminococcus lactaris*, 30% *Gemelia* sp., 10% *Peptoniphilus* sp. (10 clones) |
| | Clostridiales Incertae Sedis XI | ClosXIF (0.3) | ClosXI-XIIR ClosXIR (0.3) | 45X (30s 30s 45s @ 94° C. 54° C. 72° C.) | 3.1E+08 | *Peptoniphilus lacrimalis* | n.a. |
| | Clostridiales Incertae Sedis XII | ClosXIIF (0.3) | ClosXI-XIIR (0.3) | 45X (30s 30s 45s @ 94° C. 54° C. 72° C.) | 9.7E+04 | *Anaerococcus* sp. | n.a. |
| | Pepto-Strepto-coccaceae** | PeptosFL (0.3) | PeptosFR (0.3) | 45X (30s 30s 30s @ 94° C. 58° C. 72° C.) | 5.2E+04 | mixed | 75% *Peptoniphilus lacrimalis*, 12.5% *Peptostreptococcus anaerobius*, 12.5% ~*P. lacrimalis* [0.96] (8 clones) |
| | Mega-sphaera/-Dialister/Veillonella | Mega+L444 (0.1) | MegaR870 (0.1) | 45X (30s 30s 30s @ 94° C. 66° C. 72° C.) | 1.2E+06 | mixed | 80% *Dialister micraerophilus*, 10% *Veillonella* sp., 10% uncultured bacterium (*Dialister invisus* [0.94]) (10 clones) |
| | Staphyl-ococcus | SSL455 (0.2) | StaphR955 (0.2) | 40X (30s 30s 30s @ 94° C. 66° C. 72° C.) | 9.0E+04 | mixed | 55% *S. epidermidis*, 33% *S. lugdunensis/hominis/epidermidis*, 11% uncultured *Aerococcus* sp. (*A. viridians* [0.96]) (9 clones) |
| | Strepto-coccus | SSL454 (0.2) | StrepR860 (0.2) | 45X (30s 30s 30s @ 94° C. 62° C. 72° C.) | 1.8E+05 | *S. anginosus* | n.a. |
| Proteo-bacteria | Alpha-Proteo-bacteria† | n.a.† | n.a.† | n.a.† | n.a.† | n.a.† | n.a.† |
| | Beta-Proteo-bacteria | BProL841-2 (1) | BProR1085-2 (1) | 45X (30s 30s 15s @ 94° C. 54° C. 72° C.) | 2.6E+04 | mixed | 28% *Burkholderia* sp., 28% *Neisseria* sp., 28% *Zoogloea* sp., 14% *Achromobacter/Bordetella* sp. (7 clones) |

TABLE 3A-continued

Acute BV PBN-qPCR

| | Target | Forward Name (mM) | Reverse Name (mM) | PCR Program** | Acute BV PB-qPCR | | |
|---|---|---|---|---|---|---|---|
| | | | | | Cells/sample | ID Uncloned | ID Clones |
| | Entero-bacteriales, Pasteurellales, Pseudo-monadaceae | GPro-L154a-e (0.9) | Gpro-R970a-d (0.9) | 40X (30s 30s 60s @ 94° C. 58° C. 72° C.) | 2.9E+03 | mixed | 85% Hemophilus parainfluenzae, 10% Pseudomonas extremaustralis, 5% novel sp. (~Pseudomonas fluorescens [0.92]) (20 clones) |
| | Epsilon-Proteo-bacteria† | n.a.† | n.a.† | n.a.† | n.a.† | n.a.† | n.a.† |
| Teneri-cute | Myco-plasmatales | MycoF1a MycoF1b MycoF1c 0.3) | MycoRa MycoRb MycoRc (0.3) | 40X (30s 30s 40s @ 94° C. 52° C. 72° C.) | 1.1E+06 | Urea-plasma urealyticum | n.a |

TABLE 3B

Post-tinidazole PC-qPCR

| | Target | Forward Name (mM) | Reverse Name (mM) | PCR Program** | Post-Tinidazole PB-qPCR | | |
|---|---|---|---|---|---|---|---|
| | | | | | Cells/ sample | ID Uncloned | ID Clones |
| Broad | Broad-spectrum | BU4L (0.4) | BU6R (0.4) | 40X (30s 30s 30s @ 94° C. 58° C. 72° C.) | 1.4E+10 | n.a. | See Post Tinidazole 16S-C&S |
| non-Lacto-bacillus | Blocked Broad-spectrum (Lacto-bacillaceae) | BU4L (0.1) LB blocker3 (0.7) LBB3p (2.5) | BU6R (0.1) LB blocker4 (0.7) LBB4p (2.5) | 45X (30s 30s 30s 30s @ 5° C. 74° C. 58° C. 72° C.) 40X (30s 20s 25s 30s @ 4° C. 74° C. 56° C. 72° C.) | n.a. | n.a. | n.a. |
| Broad for nested PCR | Broad-spectrum nested | 8FM (0.3) | 1501R (0.3) | 24X-40X (30s 30s 90s @ 94 C. 54 C. 72 C.) | n.a. | n.a. | n.a. |
| Broad for nested PCR (enhanced) | Broad-spectrum nested | 8F1 8F2 8F3 8F4 8FX (0.3) | 1501-1 1501-2 (0.3) | 24X-40X (30s 30s 90s @ 94 C. 54 C. 72 C.) | n.a. | n.a. | n.a. |
| Firmicute | Lacto-bacillaceae | LB-L3 (0.3) | LB-R6 (0.3) | 40X (30s 60s @ 94° C. 74° C.) | 8.4E+09 | L. iners | n.a. |
| Actino-bacteria | Actino-bacteridae | Actino L8i (0.01) L8g (0.3) | Actino R3 (0.3) | 40X (30s 30s 45s @ 94° C. 62° C. 72° C.) | 5.7E+04 | mixed | 64% Corynebacterium spp., 12% unnamed sp. (~Dietzia alimentaria [0.96]), 6% novel sp. (~C. lipophiloflavum [0.94]), 6% Propionibacterium sp., 6% Rothia mucilaginosa, 6% Propionimicrobium lymphophilum (17 clones) |
| | Corio-bacteridae | Corio-L3H (0.6) | Corio-R4H (0.6) | 40X (30s 90s @ 94° C. 72° C.) | 4.0E+04 | A. rimae | n.a. |
| | Mobi-luncus | Mobil135L (0.3) | Mobil549R (0.3) | 40X (30s 30s 30s @ 94° C. 62° C. 72° C.) | 0 | n.d. | n.d. |
| Bacter-oides | Bacteroid-aceae/uc Prevotel-laceae | BrdF (0.3) | BrdRa BrdRb (0.3) | 40X (30s 30s 60s @ 94° C. 68° C. 72° C.) | 4.7E+06 | Prevotella sp. | n.a. |
| Fuso-bacteria | Fuso-bacterium | Fuso-L5,L6 (0.2) | Fuso-R6 (0.2) | 45X (30s 30s 30s @ 94° C. 61° C. 72° C.) | 2.9E+02 | Leptotrichia sp. (L. hofstadii [0.95]) | Leptotrichia spp. (~L. hofstadii [0.95-0.97]) (8 clones) |

TABLE 3B-continued

| | | Post-tinidazole PC-qPCR | | | | Post-Tinidazole PB-qPCR | | |
|---|---|---|---|---|---|---|---|---|
| | | Forward | Reverse | | | | | |
| | Target | Name (mM) | Name (mM) | PCR Program** | Cells/ sample | ID Uncloned | ID Clones | |
| Firmi- cute | Lachno- spiracea uc & incertae- sedis, Clostridium IVa, Roseburia | Lachno-LM (0.3) | Lachno-R3 (0.3) | 45X (30s 30s 45s @ 94° C. 64° C. 72° C.) | 2.8E+05 | ~uc Lachnospiraceae | 36% uc bacteria (~Ruminococcus obeum [0.95]), 27% uc bacteria from gut metagenome, 18% uc bacteria (~Shuttleworthia [0.93]), 9% Ruminococcus sp. (11 clones) | |
| | uc Clostri- diales (BVAB2&3 subset) | BVAB2/3- L1 (0.1) | BVAB2/3- R1 (0.1) | 40X (30s 75s @ 94° C. 68° C.) | 0 | n.d. | n.d. | |
| | Cross- family Clostridia | ClosL445a (0.1) | ClosR895 (0.3) | 40X (30s 60s @ 94° C. 74° C.) | 3.9E+03 | mixed | 50% Nosocomiicoccus sp., 33% S. epidermidis, 17% E. faecalis (8 clones) | |
| | Clostri- diales Incertae Sedis XI | ClosXIF (0.3) | ClosXI-XIIR ClosXIR (0.3) | 45X (30s 30 s 45s @ 94° C. 54° C. 72° C.) | 0 | n.d. | n.d. | |
| | Clostri- diales Incertae Sedis XII | ClosXIIF (0.3) | ClosXI-XIIR (0.3) | 45X (30s 30s 45s @ 94° C. 54° C. 72° C.) | 5.5E+03 | Clostridiales bacterium | n.a. | |
| | Pepto- Strepto- coccaceae** | PeptosFL (0.3) | PeptosFR (0.3) | 45X (30s 30s 30s @ 94° C. 58° C. 72° C.) | 0 | n.d. | n.d. | |
| | Mega- sphaera/- Dialister/ Veillonella | Mega+L444 (0.1) | MegaR870 (0.1) | 45X (30s 30s 30s @ 94° C. 66° C. 72° C.) | 1.8E+03 | mixed | Veillonella sp. (2 clones) | |
| | Staphyl- ococcus | SSL455 (0.2) | StaphR955 (0.2) | 40X (30s 30s 30s @ 94° C. 66° C. 72° C.) | 1.0E+05 | mixed | 86% S. epidermidis, 7% S. lugdunensis/ hominis/epidermidis, 7% S. pettenkoferi/ epidermidis (15 clones) | |
| | Strepto- coccus | SSL454 (0.2) | StrepR860 (0.2) | 45X (30s 30s 30s @ 94° C. 62° C. 72° C.) | 8.1E+05 | S. agalactiae | S. agalactiae (9 clones) | |
| Proteo- bacteria | Alpha- Proteo- bacteria† | n.a.† | n.a.† | n.a.† | n.a.† | n.a.† | n.a.† | |
| | Beta- Proteo- bacteria | BProL841- 2 (1) | BProR1085-2 (1) | 45X (30s 30s 15s @ 94° C. 54° C. 72° C.) | 2.6E+04 | mixed | 30% Burkholderia sp., 20% Achromobacter/ Bordetella sp., 20% Neisseria sp., 20% Variovorax/Acidovorax, 10% unclassified Burkholderiales (10 clones) | |
| | Entero- bacteriales, Pasteur- ellales, Pseudo- mona- daceae | GPro-L154 a-e (0.9) | GPro-R970 a-d (0.9) | 40X (30s 30s 60s @ 94° C. 58° C. 72° C.) | 2.9E+03 | mixed | 75% uc Haemophilus/Aggregat- ibacter, 12.5% H. parainfluenzae, 6.3% P. extremaustralis, 6.3% novel species (~Serratia marcescens [0.95]) (16 clones) | |
| | Epsilon- Proteo- bacteria† | n.a.† | n.a.† | n.a.† | n.a.† | n.a.† | n.a.† | |
| Tener- icute | Myco- Plasma- tales | MycoF1a MycoF1b MycoF1c (0.3) | MycoRa MycoRb MycoRc (0.3) | 40X (30s 30s 40s @ 94° C. 52° C. 72° C.) | 8.3E+04 | U. urea- lyticum | n.a. | |

TABLE 3C

| | | Forward | Reverse | | AcuteBV 16S-C&S | |
|---|---|---|---|---|---|---|
| Target | | Name (mM) | Name (mM) | PCR Program** | Cells/ sample | ID Clones |
| Broad | Broad-spectrum | BU4L (0.4) | BU6R (0.4) | 40X (30s 30s 30s @ 94° C. 58° C. 72° C.) | 2.9E+09 | See below |
| non-Lactobacillus | Blocked Broad-spectrum (*Lactobacillaceae*) | BU4L (0.1) LB blocker3 (0.7) LBB3p (2.5) | BU6R (0.1) LB blocker4 (0.7) LBB4p (2.5) | 45X (30s 30s 30s 30s @ 95° C. 74° C. 58° C. 72° C.) 40X (30s 20s 25s 30s @ 94° C. 74° C. 56° C. 72° C.) | n.a. | n.a. |
| Broad for nested PCR | Broad-spectrum nested | 8FM (0.3) | 1501R (0.3) | 24X-40X (30s 30s 90s @ 94 C. 54 C. 72 C.) | n.a. | n.a. |
| Broad for nested PCR (enhanced) | Broad-spectrum nested | 8F1 8F2 8F3 8F4 8FX (0.3) | 1501-1 1501-2 (0.3) | 24X-40X (30s 30s 90s @ 94 C. 54 C. 72 C.) | n.a. | n.a. |
| *Firmicute* | *Lactobacillaceae* | LB-L3 (0.3) | LB-R6 (0.3) | 40X (30s 60s @ 94° C. 74° C.) | 2.2E+08 | *L. iners, L. gasseri, Aerococcus* |
| *Actinobacteria* | *Actinobacteridae* | ActinoL8i 0.01) L8g (0.3) | ActinoR3 (0.3 | 40X (30s 30s 45s @ 94° C. 62° C. 72° C.) | 9.7E+08 | *G. vaginalis* |
| | *Coriobacteridae* | Corio-L3H (0.6) | Corio-R4H (0.6) | 40X (30s 90s @ 94° C. 72° C.) | 6.8E+07 | *A. vaginae, Eggerthella* sp. |
| | *Mobiluncus* | Mobil135L (0.3) | Mobil549R (0.3) | 40X (30s 30s 30s @ 94° C. 62° C. 72° C.) | 0 | n.d. |
| *Bacteroides* | *Bacteroidaceae*/uc *Prevotellaceae* | BrdF (0.3) | BrdRa BrdRb (0.3) | 40X (30s 30s 60s @ 94° C. 68° C. 72° C.) | 1.0E+08 | *Prevotella bivia* |
| *Fusobacteria* | *Fusobacterium* | Fuso-L5,L6 (0.2) | Fuso-R6 (0.2) | 46X (30s 30s 30s @ 94° C. 61° C. 72° C.) | 1.4E+09 | *L. amnionii* |
| *Firmicute* | *Lachnospiracea* uc & incertae sedis, *Clostridium* IVa, *Roseburia* | Lachno-LM (0.3) | Lachno-R3 (0.3) | 45X (30s 30s 46s @ 94° C. 64° C. 72° C.) | 5.1E+07 | novel *Roseburia* sp. |
| | uc *Clostridiales* (BVAB2&3 subset) | BVAB2/3-L1 (0.1) | BVAB2/3-R1 (0.1) | 40X (30s 75s @ 94° C. 68° C.) | 0 | n.d. |
| | Cross-family *Clostridia* | ClosL445a (0.1) | ClosR698 (0.3) | 40X (30s 60s @ 94° C. 74° C.) | 0 | n.d. |
| | *Clostridiales* Incertae Sedis XI | ClosXIF (0.3) | ClosXI-XIIR ClosXIR (0.3) | 45X (30s 30s 45s @ 94° C. 54° C. 72° C.) | 3.4E+07 | *Peptoniphilis* sp. |
| | *Clostridiales* Incertae Sedis XII | ClosXIIF (0.3) | ClosXI-XIIR (0.3) | 45X (30s 30s 45s @ 94° C. 54° C. 72° C.) | 0 | n.d. |
| | *Peptostreptococcaceae*** | PeptosFL (0.3) | PeptosFR (0.3) | 45X (30s 30s 30s @ 94° C. 58° C. 72° C.) | 0 | n.d. |
| | *Megasphaera-/ Dialister/ Veillonella* | Mega+L444 (0.1) | MegaR870 (0.1) | 45X (30s 30s 30s @ 94° C. 66° C. 72° C.) | 1.7E+07 | *Dialister* sp. |
| | *Staphylococcus* | SSL455 (0.2) | StaphR955 (0.2) | 40X (30s 30s 30s @ 94° C. 66° C. 72° C.) | 0 | n.d. |
| | *Streptococcus* | SSL454 (0.2) | StrepR660 (0.2) | 45X (30s 30s 30s @ 94° C. 62° C. 72° C.) | 0 | n.d. |
| *Proteobacteria* | Alpha-Proteobacteria† | n.a.† | n.a.† | n.a.† | 0 | n.d. |
| | Beta-Proteobacteria | BProL841-2 (1) | BProR1085-2 (1) | 45X (30s 30s 15s @ 94° C. 54° C. 72° C.) | 1.7E+07 | *Janthinobacterium lividum* |
| | Enterobacteriales Pasteurellales, Pseudomonadaceae | GPro-L154a-e (0.9) | GPro-R970a-d (0.9) | 40X (30s 30s 60s @ 94° C. 58° C. 72° C.) | 0 | n.d. |
| | Epsilon-proteobacteria† | n.a.† | n.a.† | n.a.† | 0 | n.d. |

TABLE 3C-continued

Acute BV 16S-C&S

| Target | | Forward Name (mM) | Reverse Name (mM) | PCR Program** | AcuteBV 16S-C&S Cells/sample | ID Clones |
|---|---|---|---|---|---|---|
| Tenericute | Mycoplasmatales | MycoF1a MycoF1b MycoF1c (0.3) | MycoRa MycoRb MycoRc (0.3) | 40X (30s 30s 40s @ 94° C. 52° C. 72° C.) | 0 | n.d. |

TABLE 3D

Post tinidazole 16S-C&S

| Target | | Forward Name (mM) | Reverse Name (mM) | PCR Program** | Post Tinidazole 16S-C&S Cells/sample | ID Clones |
|---|---|---|---|---|---|---|
| Broad | Broad-spectrum | BU4L (0.4) | BU6R (0.4) | 40X (30s 30s 30s @ 94° C. 58° C. 72° C.) | 8.4E+09 | See Lactobacillaceae below |
| non-Lactobacillus | Blocked Broad-spectrum (Lactobacillaceae) | BU4L (0.1) LB blocker3 (0.7) LBB3p (2.5) | BU6R (0.1) LB blocker4 (0.7) LBB4p (2.5) | 45X (30s 30s 30s 30s @ 95° C. 74° C. 58° C. 72° C.) 40X (30s 20s 25s 30s @ 94° C. 74° C. 56° C. 72° C.) | | See non-Lactoballaceae phyla below |
| Broad for nested PCR | Broad-spectrum nested | 8FM (0.3) | 1501R (0.3) | 24X-40X (30s 30s 90s @ 94° C. 54 C. 72° C.) | n.a. | n.a. |
| Broad for nested PCR (enhanced) | Broad-spectrum nested | 8F1 8F2 8F3 8F4 8FX (0.3) | 1501-1 1501-2 (0.3) | 24X-40X (30s 30s 90s @ 94 C. 54 C. 72° C.) | n.a. | n.a. |
| Firmicute | Lactobacillaceae | LB-L3 (0.3) | LB-R6 (0.3) | 40X (30s 60s @ 94° C. 74° C.) | 8.4E+09 | L. iners 83%, L. jensenii 17%, novel Lactobacillus |
| Actinobacteria | Actinobacteridae | ActinoL8i (0.01) L8g (0.3) | ActinoR3 (0.3) | 40X (30s 30s 45s @ 94° C. 62° C. 72° C.) | 1.3E+06 | G. vaginalis, Propionibacterium acnes, Corynebacterium spp. (some novel), Actinomycetales sp., Brevibacterium sp. |
| | Coriobacteridae | Corio-L3H (0.6) | Corio-R4H (0.6) | 40X (30s 90s @ 94° C. 72° C.) | 0 | n.d. |
| | Mobiluncus | Mobil 135L (0.3) | Mobil 549R (0.3) | 40X (30s 30s 30s @ 94° C. 62° C. 72° C.) | 0 | n.d. |
| Bacteroides | Bacteroidaceae/uc Prevotellaceae | BrdF (0.3) | BrdRa BrdRb (0.3) | 40X (30s 30s 60s @ 94° C. 68° C. 72° C.) | 3.4E+04 | Bacteroides sp. |
| Fusobacteria | Fusobacterium | Fuso-L5,L6 (0.2) | Fuso-R6 (0.2) | 45X (30s 30s 30s @ 94° C. 61° C. 72° C.) | 0 | n.d. |
| Firmicute | Lachnospiracea uc & incertae sedis, Clostridium IVa, Roseburia | Lachno-LM (0.3) | Lachno-R3 (0.3) | 45X (30s 30s 45s @ 94° C. 64° C. 72° C.) | 0 | novel Ruminococcus sp. |

TABLE 3D-continued

Post tinidazole 16S-C&S

| | | Forward | Reverse | | Post Tinidazole 16S-C&S | |
|---|---|---|---|---|---|---|
| | Target | Name (mM) | Name (mM) | PCR Program** | Cells/ sample | ID Clones |
| | uc Clostridiales (BVAB2&3 subset) | BVAB2/3-L1 (0.1) | BVAB2/3-R1 (0.1) | 40X (30s 75s @ 94° C. 68° C.) | 0 | n.d. |
| | Cross-family Clostridia | Clos L445a (0.1) | Clos R698 (0.3) | 40X (30s 60s @ 94° C. 74° C.) | 0 | n.d. |
| | Clostridiales Incertae Sedis XI | Clos XIF (0.3) | ClosXI-XIIR ClosXIR (0.3) | 45X (30s 30s 45s @ 94° C. 54° C. 72° C.) | 0 | n.d. |
| | Clostridiales Incertae Sedis XII | Clos XIIF (0.3) | Clos XI-XIIR (0.3) | 45X (30s 30s 45s @ 94° C. 54° C. 72° C.) | 0 | n.d. |
| | Pepto-Strepto-coccaceae** | Peptos FL (0.3) | Peptos FR (0.3) | 45X (30s 30s 30s @ 94° C. 58° C. 72° C.) | 0 | n.d. |
| | Mega-sphaera/-Dialister/ Veillonella | Mega+L444 (0.1) | MegaR870 (0.1) | 45X (30s 30s 30s @ 94° C. 66° C. 72° C.) | 0 | n.d. |
| | Staphyl-ococcus | SSL455 (0.2) | StaphR955 (0.2) | 40X (30s 30s 30s @ 94° C. 66° C. 72° C.) | 0 | n.d. |
| | Strepto-coccus | SSL454 (0.2) | StrepR860 (0.2) | 45X (30s 30s 30s @ 94° C. 62° C. 72° C.) | 0 | n.d. |
| Proteo-bacteria | Alpha-Proteo-bacteria† | n.a.† | n.a.† | n.a.† | 3.4E+04 | Methylobacterium aminovorans |
| | Beta-Proteo-bacteria | BProL841-2 (1) | BProR1085-2 (1) | 45X (30s 30s 15s @ 94° C. 54° C. 72° C.) | 3.4E+04 | Janthinobacterium lividum |
| | Entero-bacteriales, Pasteurellales, Pseudo-monadaceae | GPro-L154a-e (0.9) | GPro-R970a-d (0.9) | 40X (30s 30s 60s @ 94° C. 58° C. 72° C.) | 3.4E+05 | Escherichia coli, Aggregatibacter sp., Pseudomonas fluorescens, Pseudomonas pseudoalcaligenes |
| | Epsilon-Proteo-bacteria† | n.a.† | n.a.† | n.a.† | 3.4E+04 | Arcobacter cryaerophilus |
| Tenericute | Myco-plasmatales | MycoF1a MycoF1b MycoF1c | MycoRa MycoRb MycoRc (0.3) | 40X (30s 30s 40s @ 94° C. 52° C. 72° C.) | 0 | n.d. |

TABLE 3E

In silicose performance

| | | In silico performance | | | | |
|---|---|---|---|---|---|---|
| | Target | Target hits | Total hits | Specificity % | Total target number | Target coverage (%) |
| Broad non-Lactobacillus | Broad-spectrum | 1003253 | | | 1052808 | 95 |
| | Blocked Broad-spectrum (Lactobacillaceae) | 9752 | 9784 | 99.7 | 13094 | 74.5 |
| | | 10684 | 10690 | 99.9 | 13094 | 81.6 |
| Broad for nested PCR | Broad-spectrum nested | 7612 | 7612 | 100 | 16646 | 45.7 |
| Broad for nested PCR (enhanced) | Broad-spectrum nested | Table 1S | Table 1S | n.a.† | Table 1S | Table 1S |
| Firmicute | Lactobacillaceae | 8431 | 8534 | 99 | 13094 | 64 |
| Actinobacteria | Actinobacteridae | 138463 | 139346 | 99 | 155995 | 89 |
| | Coriobacteridae | 1468 | 1468 | 100 | 2089 | 70 |
| | Mobiluncus | 49 | 49 | 100 | 53 | 92 |
| Bacteroides | Bacteroidaceae/uc Prevotellaceae | 107239 | 107261 | 100 | 268258 | 40 |

TABLE 3E-continued

In silicose performance

| | | \multicolumn{5}{c}{In silico performance} | | | | |
|---|---|---|---|---|---|---|
| | Target | Target hits | Total hits | Specificity % | Total target number | Target coverage (%) |
| *Fusobacteria* | *Fusobacterium* | 4163 | 4163 | 100 | 4514 | 92 |
| *Firmicute* | *Lachnospiracea* uc & incertae sedis, *Clostridium* IVa *Roseburia* | 31293 | 31624 | 99 | 46002 | 68 |
| | uo *Clostridiales* (BVAB2&3 subset) | 315 | 393 | 80 | 315 | 100 |
| | Cross-family *Clostridia* | 59237 | 62122 | 95 | 59237 | 100 |
| | *Clostridiales* Incertae Sedis XI | 2846 | 3016 | 94 | 8637 | 33 |
| | *Clostridiales* Incertae Sedis XII | 110 | 204 | 54 | 495 | 22 |
| | *Peptostreptococcaceae*** | 1428 | 1428 | 100 | 3902 | 37 |
| | *Megasphaera/Dialister/Veillonella* | 3240 | 3263 | 99 | 3240 | 100 |
| | *Staphylococcus* | 102342 | 102517 | 100 | 115420 | 89 |
| | *Streptococcus* | 42087 | 42091 | 100 | 44407 | 95 |
| *Proteobacteria* | *Alphaproteobacteria*† | n.a.† | n.a.† | n.a.† | n.a.† | n.a.† |
| | *Betaproteobacteria* | 50312 | 50588 | 99 | 66548 | 76 |
| | *Enterobacteriales, Pasteurellales, Pseudomonadaceae* | 33257 | 33260 | 100 | 58219 | 57 |
| | *Epsilonproteobacteria*† | n.a.† | n.a.† | n.a.† | n.a.† | n.a.† |
| *Tenericute* | *Mycoplasmatales* | 269 | 269 | 100 | 736 | 37 |

TABLE 4

Richness and diversity parameters

| Sample | Taxonomic diversity (OTUs) | | Good's Coverage | | Shannon-Weiner Index | | Chao1 (std. dev.) | |
|---|---|---|---|---|---|---|---|---|
| | Broad Spectrum | PB-qPCR+ | Broad Spectrum | PB-qPCR+ | Broad Spectrum | PB-qPCR+ | Broad Spectrum | PB-qPCR+ |
| Acute BV | 13 | 30 | 93.6 | 100 | 1.4 | 1.5 | 19(5) | 53 |
| Blocked post-tinidazele | 22 | 33 | 88.4 | 100 | 1.7 | 0.01 | 135(60) | 52 |
| Unblocked post-tinidazole | 2 | | 100 | | 0.5 | | na | |

OTU: operational taxonomic unit, here, sequences <3% divergent. Good's coverage = 100 × (1 − (#OTUs/total sequences))
(1). The Shannon-Weiner index = −âpi(in pi), pi = proportion of sequences of each OTU
(2). Chao1 nonparametric estimator for broad-spectrum libraries was calculated online with FastGroup II tools http://fastgroup.sdsu.edu/cal....tools.htm
(3). Chao1 = S(obs) + (a2/2b)
(4) was used to estimate diversity in the PB-qPCR+ data by assigning single hits as the lowest titer OTUs (<104), two hit as the next highest titer OTUs (<1e5), where the high titer groups were >1e11.

What is claimed is:

1. A kit for assessing health of a vaginal microbiome comprising:
    a first set of primers comprising forward primers and reverse primers that support amplification of total bacterial DNA present in the vaginal microbiome, wherein at least one forward primer in the first set of primers comprises SEQ ID NO: 1, SEQ ID NO: 2, SEQ ID NO: 3, and/or SEQ ID NO: 4, and at least one reverse primer in the first set of primers comprises SEQ ID NO: 5, SEQ ID NO: 6, SEQ ID NO: 7, SEQ ID NO: 8, SEQ ID NO: 9, SEQ ID NO: 10, and/or SEQ ID NO: 58; and
    a second set of primers comprising at least one forward blocking primer and at least one reverse blocking primer, wherein the at least one forward blocking primer in the second set of primers partially overlaps the binding site of a forward primer in the first set of primers, wherein the at least one reverse blocking primer in the second set of primers partially overlaps the binding site of a reverse primer in the first set of primers, wherein the 3' end of each of the at least one forward blocking primer and the at least one reverse blocking primer in the second set of primers comprises mismatches to sequences in the Lactobacillus (LB) genome, and wherein the kit is capable of detecting one or more non-LB species DNA at a titer below $1\times10^6$ cells/sample in an amplification reaction.

2. The kit of claim 1, wherein the melting temperatures of the forward and reverse blocking primers are at least 68° C.

3. The kit of claim 1, wherein the blocking primers are selected from LBblocker3, LBB3p, LBblocker4, and LBB4p.

4. The kit of claim 1, further comprising one or more primers selected from SEQ ID NO: 11, SEQ ID NO: 12, SEQ ID NO: 13, SEQ ID NO: 14, SEQ ID NO: 15, SEQ ID NO: 16, SEQ ID NO: 24, SEQ ID NO: 25, SEQ ID NO: 26, SEQ ID NO: 27, SEQ ID NO: 28, SEQ ID NO: 29, SEQ ID NO: 61, SEQ ID NO: 62, and SEQ ID NO: 63.

* * * * *

SEQUENCE LISTING

<160> NUMBER OF SEQ ID NOS: 96

<210> SEQ ID NO 1
<211> LENGTH: 18
<212> TYPE: DNA
<213> ORGANISM: Artificial Sequence
<220> FEATURE:
<223> OTHER INFORMATION: BU4F+ Primer

<400> SEQUENCE: 1
ctcctacggg aggcagca                                                       18

```
<210> SEQ ID NO 2
<211> LENGTH: 18
<212> TYPE: DNA
<213> ORGANISM: Artificial Sequence
<220> FEATURE:
<223> OTHER INFORMATION: BU4F+ Primer

<400> SEQUENCE: 2
ctcctacggg aggctgca                                                 18

<210> SEQ ID NO 3
<211> LENGTH: 17
<212> TYPE: DNA
<213> ORGANISM: Artificial Sequence
<220> FEATURE:
<223> OTHER INFORMATION: BU4F+ Primer

<400> SEQUENCE: 3
ccctacgggg ggcagca                                                  17

<210> SEQ ID NO 4
<211> LENGTH: 18
<212> TYPE: DNA
<213> ORGANISM: Artificial Sequence
<220> FEATURE:
<223> OTHER INFORMATION: BU4F+ Primer

<400> SEQUENCE: 4
cacctacggg tggcagca                                                 18

<210> SEQ ID NO 5
<211> LENGTH: 21
<212> TYPE: DNA
<213> ORGANISM: Artificial Sequence
<220> FEATURE:
<223> OTHER INFORMATION: BU6R+ Primer

<400> SEQUENCE: 5
gactacaggg gtatctaatc c                                             21

<210> SEQ ID NO 6
<211> LENGTH: 22
<212> TYPE: DNA
<213> ORGANISM: Artificial Sequence
<220> FEATURE:
<223> OTHER INFORMATION: BU6R+ Primer

<400> SEQUENCE: 6
gactaccagg ggtatctaat cc                                            22

<210> SEQ ID NO 7
<211> LENGTH: 21
<212> TYPE: DNA
<213> ORGANISM: Artificial Sequence
<220> FEATURE:
<223> OTHER INFORMATION: BU6R+ Primer

<400> SEQUENCE: 7
gactaccggg gtatctaatc c                                             21

<210> SEQ ID NO 8
<211> LENGTH: 23
<212> TYPE: DNA
<213> ORGANISM: Artificial Sequence
<220> FEATURE:
<223> OTHER INFORMATION: BU6R+ Primer
```

```
<220> FEATURE:
<221> NAME/KEY: misc_feature
<222> LOCATION: (15)..(15)
<223> OTHER INFORMATION: N is C or T

<400> SEQUENCE: 8
gactacccgg gtatntaatc cgg                                              23

<210> SEQ ID NO 9
<211> LENGTH: 23
<212> TYPE: DNA
<213> ORGANISM: Artificial Sequence
<220> FEATURE:
<223> OTHER INFORMATION: BU6R+ Primer

<400> SEQUENCE: 9
ggactactag ggtatctaat cct                                              23

<210> SEQ ID NO 10
<211> LENGTH: 23
<212> TYPE: DNA
<213> ORGANISM: Artificial Sequence
<220> FEATURE:
<223> OTHER INFORMATION: BU6R+ Primer
<220> FEATURE:
<221> NAME/KEY: misc_feature
<222> LOCATION: (8)..(8)
<223> OTHER INFORMATION: N is A or G
<220> FEATURE:
<221> NAME/KEY: misc_feature
<222> LOCATION: (19)..(19)
<223> OTHER INFORMATION: N is T or G

<400> SEQUENCE: 10
gactaccngg gtatctaanc ctg                                              23

<210> SEQ ID NO 11
<211> LENGTH: 15
<212> TYPE: DNA
<213> ORGANISM: Artificial Sequence
<220> FEATURE:
<223> OTHER INFORMATION: 1492R Primer

<400> SEQUENCE: 11
accttgttac gactt                                                       15

<210> SEQ ID NO 12
<211> LENGTH: 41
<212> TYPE: DNA
<213> ORGANISM: Artificial Sequence
<220> FEATURE:
<223> OTHER INFORMATION: 27F Primer

<400> SEQUENCE: 12
gccttgccag cccgctcagt cagagtttga tcctggctca g                          41

<210> SEQ ID NO 13
<211> LENGTH: 48
<212> TYPE: DNA
<213> ORGANISM: Artificial Sequence
<220> FEATURE:
<223> OTHER INFORMATION: 338R Primer
<220> FEATURE:
<221> NAME/KEY: misc_feature
<222> LOCATION: (20)..(27)
<223> OTHER INFORMATION: N is A, C, G, or T
```

<400> SEQUENCE: 13
gcctccctcg cgccatcagn nnnnnnncat gctgcctccc gtaggagt          48

<210> SEQ ID NO 14
<211> LENGTH: 17
<212> TYPE: DNA
<213> ORGANISM: Artificial Sequence
<220> FEATURE:
<223> OTHER INFORMATION: 534R Primer

<400> SEQUENCE: 14
cctacgggag gcagcag          17

<210> SEQ ID NO 15
<211> LENGTH: 20
<212> TYPE: DNA
<213> ORGANISM: Artificial Sequence
<220> FEATURE:
<223> OTHER INFORMATION: 338F Primer
<220> FEATURE:
<221> NAME/KEY: misc_feature
<222> LOCATION: (7)..(7)
<223> OTHER INFORMATION: N is A or G

<400> SEQUENCE: 15
actcctncgg gaggcagcag          20

<210> SEQ ID NO 16
<211> LENGTH: 20
<212> TYPE: DNA
<213> ORGANISM: Artificial Sequence
<220> FEATURE:
<223> OTHER INFORMATION: 806R Primer
<220> FEATURE:
<221> NAME/KEY: misc_feature
<222> LOCATION: (9)..(9)
<223> OTHER INFORMATION: N is A, C, or G

<400> SEQUENCE: 16
ggactaccng ggtatctaat          20

<210> SEQ ID NO 17
<211> LENGTH: 23
<212> TYPE: DNA
<213> ORGANISM: Artificial Sequence
<220> FEATURE:
<223> OTHER INFORMATION: pUC Universal Primer

<400> SEQUENCE: 17
cccagtcacg acgttgtaaa acg          23

<210> SEQ ID NO 18
<211> LENGTH: 23
<212> TYPE: DNA
<213> ORGANISM: Artificial Sequence
<220> FEATURE:
<223> OTHER INFORMATION: pUC Reverse Primer

<400> SEQUENCE: 18
agcggataac aatttcacac agg          23

<210> SEQ ID NO 19
<211> LENGTH: 21
<212> TYPE: DNA
<213> ORGANISM: Artificial Sequence
<220> FEATURE:
<223> OTHER INFORMATION: LucF3 Primer

<400> SEQUENCE: 19
gcttactggg acgaagacga a                                              21

<210> SEQ ID NO 20
<211> LENGTH: 20
<212> TYPE: DNA
<213> ORGANISM: Artificial Sequence
<220> FEATURE:
<223> OTHER INFORMATION: LucR3 Primer

<400> SEQUENCE: 20
gcggttgtta cttgactggc                                                20

<210> SEQ ID NO 21
<211> LENGTH: 18
<212> TYPE: DNA
<213> ORGANISM: Artificial Sequence
<220> FEATURE:
<223> OTHER INFORMATION: BU4L Primer

<400> SEQUENCE: 21
ctcctacggg aggcagca                                                  18

<210> SEQ ID NO 22
<211> LENGTH: 25
<212> TYPE: DNA
<213> ORGANISM: Artificial Sequence
<220> FEATURE:
<223> OTHER INFORMATION: LB-blocker3 Primer
<220> FEATURE:
<221> NAME/KEY: misc_feature
<222> LOCATION: (1)..(2)
<223> OTHER INFORMATION: N is G-Phosphorothioate
<220> FEATURE:
<221> NAME/KEY: misc_feature
<222> LOCATION: (3)..(3)
<223> OTHER INFORMATION: N is C-Phosphorothioate
<220> FEATURE:
<221> NAME/KEY: misc_feature
<222> LOCATION: (4)..(4)
<223> OTHER INFORMATION: N is A-Phosphorothioate
<220> FEATURE:
<221> NAME/KEY: misc_feature
<222> LOCATION: (19)..(19)
<223> OTHER INFORMATION: N is T-Phosphorothioate
<220> FEATURE:
<221> NAME/KEY: misc_feature
<222> LOCATION: (20)..(21)
<223> OTHER INFORMATION: N is C-Phosphorothioate
<220> FEATURE:
<221> NAME/KEY: misc_feature
<222> LOCATION: (22)..(22)
<223> OTHER INFORMATION: N is A-Phosphorothioate
<220> FEATURE:
<221> NAME/KEY: misc_feature
<222> LOCATION: (23)..(24)
<223> OTHER INFORMATION: N is T-Phosphorothioate

<400> SEQUENCE: 22
nnnngcagta gggaatctnn nnnnt                                          25

<210> SEQ ID NO 23
<211> LENGTH: 23
<212> TYPE: DNA
<213> ORGANISM: Artificial Sequence
<220> FEATURE:
<223> OTHER INFORMATION: LBB3p Primer

<400> SEQUENCE: 23
ggcagcagta gggaatcttc cat                                            23

```
<210> SEQ ID NO 24
<211> LENGTH: 20
<212> TYPE: DNA
<213> ORGANISM: Artificial Sequence
<220> FEATURE:
<223> OTHER INFORMATION: 8FM Primer
<220> FEATURE:
<221> NAME/KEY: misc_feature
<222> LOCATION: (12)..(12)
<223> OTHER INFORMATION: N is A or C

<400> SEQUENCE: 24
agagtttgat cntggctcag                                                 20

<210> SEQ ID NO 25
<211> LENGTH: 20
<212> TYPE: DNA
<213> ORGANISM: Artificial Sequence
<220> FEATURE:
<223> OTHER INFORMATION: 8F1 Primer

<400> SEQUENCE: 25
agagtttgat cctggcttag                                                 20

<210> SEQ ID NO 26
<211> LENGTH: 20
<212> TYPE: DNA
<213> ORGANISM: Artificial Sequence
<220> FEATURE:
<223> OTHER INFORMATION: 8F2 Primer
<220> FEATURE:
<221> NAME/KEY: misc_feature
<222> LOCATION: (6)..(6)
<223> OTHER INFORMATION: N is C or T
<220> FEATURE:
<221> NAME/KEY: misc_feature
<222> LOCATION: (11)..(11)
<223> OTHER INFORMATION: N is C or T

<400> SEQUENCE: 26
agggtncgat nctggctcag                                                 20

<210> SEQ ID NO 27
<211> LENGTH: 20
<212> TYPE: DNA
<213> ORGANISM: Artificial Sequence
<220> FEATURE:
<223> OTHER INFORMATION: 8F3 Primer

<400> SEQUENCE: 27
agaatttgat cttggttcag                                                 20

<210> SEQ ID NO 28
<211> LENGTH: 21
<212> TYPE: DNA
<213> ORGANISM: Artificial Sequence
<220> FEATURE:
<223> OTHER INFORMATION: 8F4 Primer
<220> FEATURE:
<221> NAME/KEY: misc_feature
<222> LOCATION: (20)..(20)
<223> OTHER INFORMATION: N is A or C

<400> SEQUENCE: 28
agagtttgat cctggctcan g                                               21
```

```
<210> SEQ ID NO 29
<211> LENGTH: 19
<212> TYPE: DNA
<213> ORGANISM: Artificial Sequence
<220> FEATURE:
<223> OTHER INFORMATION: 8FX Primer
<220> FEATURE:
<221> NAME/KEY: misc_feature
<222> LOCATION: (3)..(3)
<223> OTHER INFORMATION: N is C or G
<220> FEATURE:
<221> NAME/KEY: misc_feature
<222> LOCATION: (10)..(10)
<223> OTHER INFORMATION: N is C or T
<220> FEATURE:
<221> NAME/KEY: misc_feature
<222> LOCATION: (11)..(11)
<223> OTHER INFORMATION: N is A or C

<400> SEQUENCE: 29
gantttgatn ntggctcag                                           19

<210> SEQ ID NO 30
<211> LENGTH: 25
<212> TYPE: DNA
<213> ORGANISM: Artificial Sequence
<220> FEATURE:
<223> OTHER INFORMATION: LB-L3 Primer

<400> SEQUENCE: 30
ggaggcagca gtagggaatc ttcca                                    25

<210> SEQ ID NO 31
<211> LENGTH: 19
<212> TYPE: DNA
<213> ORGANISM: Artificial Sequence
<220> FEATURE:
<223> OTHER INFORMATION: Actino-L8i Primer
<220> FEATURE:
<221> NAME/KEY: misc_feature
<222> LOCATION: (2)..(4)
<223> OTHER INFORMATION: N is Inosine

<400> SEQUENCE: 31
cnnngacggg tagccggcc                                           19

<210> SEQ ID NO 32
<211> LENGTH: 19
<212> TYPE: DNA
<213> ORGANISM: Artificial Sequence
<220> FEATURE:
<223> OTHER INFORMATION: Actino-L8g Primer

<400> SEQUENCE: 32
cggggacggg tagccggcc                                           19

<210> SEQ ID NO 33
<211> LENGTH: 34
<212> TYPE: DNA
<213> ORGANISM: Artificial Sequence
<220> FEATURE:
<223> OTHER INFORMATION: Corio--L3H Primer

<400> SEQUENCE: 33
gggttgagag accgaccggc ctgagagggc gatc                          34
```

```
<210> SEQ ID NO 34
<211> LENGTH: 18
<212> TYPE: DNA
<213> ORGANISM: Artificial Sequence
<220> FEATURE:
<223> OTHER INFORMATION: GarNocL Primer

<400> SEQUENCE: 34
ttgtaggcgg ttcgtcgc                                                     18

<210> SEQ ID NO 35
<211> LENGTH: 25
<212> TYPE: DNA
<213> ORGANISM: Artificial Sequence
<220> FEATURE:
<223> OTHER INFORMATION: Mobil-135L Primer

<400> SEQUENCE: 35
ggctgctaat actggatatt caggc                                             25

<210> SEQ ID NO 36
<211> LENGTH: 21
<212> TYPE: DNA
<213> ORGANISM: Artificial Sequence
<220> FEATURE:
<223> OTHER INFORMATION: BrdF Primer
<220> FEATURE:
<221> NAME/KEY: misc_feature
<222> LOCATION: (20)..(20)
<223> OTHER INFORMATION: N is A or G

<400> SEQUENCE: 36
tcctacggga ggcagcagtn a                                                 21

<210> SEQ ID NO 37
<211> LENGTH: 19
<212> TYPE: DNA
<213> ORGANISM: Artificial Sequence
<220> FEATURE:
<223> OTHER INFORMATION: Fuso-L5 Primer

<400> SEQUENCE: 37
ccagcaattc tgtgtgcac                                                    19

<210> SEQ ID NO 38
<211> LENGTH: 19
<212> TYPE: DNA
<213> ORGANISM: Artificial Sequence
<220> FEATURE:
<223> OTHER INFORMATION: Fuso-L6 Primer

<400> SEQUENCE: 38
ccagcaattc tgtgtgtgt                                                    19

<210> SEQ ID NO 39
<211> LENGTH: 24
<212> TYPE: DNA
<213> ORGANISM: Artificial Sequence
<220> FEATURE:
<223> OTHER INFORMATION: Lachno-LM Primer
<220> FEATURE:
<221> NAME/KEY: misc_feature
<222> LOCATION: (16)..(16)
<223> OTHER INFORMATION: N is A or C

<400> SEQUENCE: 39
gtaaagctct atcagnaggg aaga                                              24
```

```
<210> SEQ ID NO 40
<211> LENGTH: 19
<212> TYPE: DNA
<213> ORGANISM: Artificial Sequence
<220> FEATURE:
<223> OTHER INFORMATION: BVAB2/3-L1 Primer

<400> SEQUENCE: 40
gcgaaagcct gacccagca                                               19

<210> SEQ ID NO 41
<211> LENGTH: 20
<212> TYPE: DNA
<213> ORGANISM: Artificial Sequence
<220> FEATURE:
<223> OTHER INFORMATION: ClosL-445a-1 Primer
<220> FEATURE:
<221> NAME/KEY: misc_feature
<222> LOCATION: (2)..(2)
<223> OTHER INFORMATION: N is C or G

<400> SEQUENCE: 41
cnacgatgcg tagccgacct                                              20

<210> SEQ ID NO 42
<211> LENGTH: 20
<212> TYPE: DNA
<213> ORGANISM: Artificial Sequence
<220> FEATURE:
<223> OTHER INFORMATION: ClosL-445a-2 Primer

<400> SEQUENCE: 42
cgacgatcag tagccgacct                                              20

<210> SEQ ID NO 43
<211> LENGTH: 20
<212> TYPE: DNA
<213> ORGANISM: Artificial Sequence
<220> FEATURE:
<223> OTHER INFORMATION: ClosL-445a-3 Primer

<400> SEQUENCE: 43
caacgatcag tagccggtct                                              20

<210> SEQ ID NO 44
<211> LENGTH: 20
<212> TYPE: DNA
<213> ORGANISM: Artificial Sequence
<220> FEATURE:
<223> OTHER INFORMATION: Clos-XIIF Primer
<220> FEATURE:
<221> NAME/KEY: misc_feature
<222> LOCATION: (12)..(12)
<223> OTHER INFORMATION: N is C or T

<400> SEQUENCE: 44
gggatagcca cnggaaacgg                                              20

<210> SEQ ID NO 45
<211> LENGTH: 21
<212> TYPE: DNA
<213> ORGANISM: Artificial Sequence
<220> FEATURE:
<223> OTHER INFORMATION: Peptos-FL Primer

<400> SEQUENCE: 45
gaggaagccc cggctaacta c                                            21
```

```
<210> SEQ ID NO 46
<211> LENGTH: 20
<212> TYPE: DNA
<213> ORGANISM: Artificial Sequence
<220> FEATURE:
<223> OTHER INFORMATION: Mega+L444 Primer
<220> FEATURE:
<221> NAME/KEY: misc_feature
<222> LOCATION: (5)..(5)
<223> OTHER INFORMATION: N is C or T

<400> SEQUENCE: 46
gcgangatca gtagccggtc                                               20

<210> SEQ ID NO 47
<211> LENGTH: 19
<212> TYPE: DNA
<213> ORGANISM: Artificial Sequence
<220> FEATURE:
<223> OTHER INFORMATION: SSL455 Primer
<220> FEATURE:
<221> NAME/KEY: misc_feature
<222> LOCATION: (2)..(2)
<223> OTHER INFORMATION: N is A or G

<400> SEQUENCE: 47
cntagccgac ctgagaggg                                                19

<210> SEQ ID NO 48
<211> LENGTH: 18
<212> TYPE: DNA
<213> ORGANISM: Artificial Sequence
<220> FEATURE:
<223> OTHER INFORMATION: SSL454 Primer

<400> SEQUENCE: 48
atagccgacc tgagaggg                                                 18

<210> SEQ ID NO 49
<211> LENGTH: 20
<212> TYPE: DNA
<213> ORGANISM: Artificial Sequence
<220> FEATURE:
<223> OTHER INFORMATION: BProL8-41-2 Primer
<220> FEATURE:
<221> NAME/KEY: misc_feature
<222> LOCATION: (2)..(2)
<223> OTHER INFORMATION: N is C or T
<220> FEATURE:
<221> NAME/KEY: misc_feature
<222> LOCATION: (8)..(8)
<223> OTHER INFORMATION: N is C or T

<400> SEQUENCE: 49
antgacgntc atgcacgaaa                                               20

<210> SEQ ID NO 50
<211> LENGTH: 22
<212> TYPE: DNA
<213> ORGANISM: Artificial Sequence
<220> FEATURE:
<223> OTHER INFORMATION: GPro-L154a Primer

<400> SEQUENCE: 50
gtaatgccta ggaatctgcc tg                                            22
```

```
<210> SEQ ID NO 51
<211> LENGTH: 22
<212> TYPE: DNA
<213> ORGANISM: Artificial Sequence
<220> FEATURE:
<223> OTHER INFORMATION: GPro-L154b Primer

<400> SEQUENCE: 51
gtaatgcctg ggaaattgcc cg                                              22

<210> SEQ ID NO 52
<211> LENGTH: 20
<212> TYPE: DNA
<213> ORGANISM: Artificial Sequence
<220> FEATURE:
<223> OTHER INFORMATION: GPro-L154c Primer

<400> SEQUENCE: 52
gtaatgtctg ggaaactgcc                                                 20

<210> SEQ ID NO 53
<211> LENGTH: 22
<212> TYPE: DNA
<213> ORGANISM: Artificial Sequence
<220> FEATURE:
<223> OTHER INFORMATION: GPro-L154d Primer

<400> SEQUENCE: 53
gtaatgcttg ggaatctggc tt                                              22

<210> SEQ ID NO 54
<211> LENGTH: 22
<212> TYPE: DNA
<213> ORGANISM: Artificial Sequence
<220> FEATURE:
<223> OTHER INFORMATION: GPro-L154e Primer
<220> FEATURE:
<221> NAME/KEY: misc_feature
<222> LOCATION: (5)..(5)
<223> OTHER INFORMATION: N is C or T

<400> SEQUENCE: 54
ggganaactt ggggaaactc aa                                              22

<210> SEQ ID NO 55
<211> LENGTH: 22
<212> TYPE: DNA
<213> ORGANISM: Artificial Sequence
<220> FEATURE:
<223> OTHER INFORMATION: Myco-F1a Primer

<400> SEQUENCE: 55
cgaaggcgcc aacttggact at                                              22

<210> SEQ ID NO 56
<211> LENGTH: 22
<212> TYPE: DNA
<213> ORGANISM: Artificial Sequence
<220> FEATURE:
<223> OTHER INFORMATION: Myco-F1b Primer
<220> FEATURE:
<221> NAME/KEY: misc_feature
<222> LOCATION: (9)..(9)
<223> OTHER INFORMATION: N is A or G
<220> FEATURE:
<221> NAME/KEY: misc_feature
<222> LOCATION: (17)..(17)
<223> OTHER INFORMATION: N is A or G
```

```
<220> FEATURE:
<221> NAME/KEY: misc_feature
<222> LOCATION: (18)..(18)
<223> OTHER INFORMATION: N is C or G

<400> SEQUENCE: 56
gaaggcgana acttagnnca tt                                              22

<210> SEQ ID NO 57
<211> LENGTH: 24
<212> TYPE: DNA
<213> ORGANISM: Artificial Sequence
<220> FEATURE:
<223> OTHER INFORMATION: Myco-F1c Primer
<220> FEATURE:
<221> NAME/KEY: misc_feature
<222> LOCATION: (21)..(21)
<223> OTHER INFORMATION: N is C or T

<400> SEQUENCE: 57
gcgaaggcag cttactgggt ntat                                            24

<210> SEQ ID NO 58
<211> LENGTH: 21
<212> TYPE: DNA
<213> ORGANISM: Artificial Sequence
<220> FEATURE:
<223> OTHER INFORMATION: BU6R Primer

<400> SEQUENCE: 58
gactaccagg gtatctaatc c                                               21

<210> SEQ ID NO 59
<211> LENGTH: 29
<212> TYPE: DNA
<213> ORGANISM: Artificial Sequence
<220> FEATURE:
<223> OTHER INFORMATION: LB-blocker4 Primer
<220> FEATURE:
<221> NAME/KEY: misc_feature
<222> LOCATION: (1)..(1)
<223> OTHER INFORMATION: N is G-Phosphorothioate
<220> FEATURE:
<221> NAME/KEY: misc_feature
<222> LOCATION: (2)..(3)
<223> OTHER INFORMATION: N is T-Phosphorothioate
<220> FEATURE:
<221> NAME/KEY: misc_feature
<222> LOCATION: (4)..(4)
<223> OTHER INFORMATION: N is C-Phosphorothioate
<220> FEATURE:
<221> NAME/KEY: misc_feature
<222> LOCATION: (23)..(24)
<223> OTHER INFORMATION: N is C-Phosphorothioate
<220> FEATURE:
<221> NAME/KEY: misc_feature
<222> LOCATION: (25)..(25)
<223> OTHER INFORMATION: N is T-Phosphorothioate
<220> FEATURE:
<221> NAME/KEY: misc_feature
<222> LOCATION: (26)..(26)
<223> OTHER INFORMATION: N is C-Phosphorothioate
<220> FEATURE:
<221> NAME/KEY: misc_feature
<222> LOCATION: (27)..(28)
<223> OTHER INFORMATION: N is T-Phosphorothioate

<400> SEQUENCE: 59
nnnngctacc catgctttcg agnnnnnnt                                       29
```

```
<210> SEQ ID NO 60
<211> LENGTH: 27
<212> TYPE: DNA
<213> ORGANISM: Artificial Sequence
<220> FEATURE:
<223> OTHER INFORMATION: LBB4p Primer

<400> SEQUENCE: 60
gttcgctacc catgctttcg agcctct                                            27

<210> SEQ ID NO 61
<211> LENGTH: 22
<212> TYPE: DNA
<213> ORGANISM: Artificial Sequence
<220> FEATURE:
<223> OTHER INFORMATION: 1501R Primer
<220> FEATURE:
<221> NAME/KEY: misc_feature
<222> LOCATION: (6)..(6)
<223> OTHER INFORMATION: N is C or T

<400> SEQUENCE: 61
tacggntacc ttgttacgac tt                                                 22

<210> SEQ ID NO 62
<211> LENGTH: 20
<212> TYPE: DNA
<213> ORGANISM: Artificial Sequence
<220> FEATURE:
<223> OTHER INFORMATION: 1501-1 Primer
<220> FEATURE:
<221> NAME/KEY: misc_feature
<222> LOCATION: (1)..(1)
<223> OTHER INFORMATION: N is A or T
<220> FEATURE:
<221> NAME/KEY: misc_feature
<222> LOCATION: (4)..(4)
<223> OTHER INFORMATION: N is A or G
<220> FEATURE:
<221> NAME/KEY: misc_feature
<222> LOCATION: (6)..(6)
<223> OTHER INFORMATION: N is C or T

<400> SEQUENCE: 62
nacngntacc ttgttacgac                                                    20

<210> SEQ ID NO 63
<211> LENGTH: 20
<212> TYPE: DNA
<213> ORGANISM: Artificial Sequence
<220> FEATURE:
<223> OTHER INFORMATION: 1501-2 Primer
<220> FEATURE:
<221> NAME/KEY: misc_feature
<222> LOCATION: (3)..(3)
<223> OTHER INFORMATION: N is C or T
<220> FEATURE:
<221> NAME/KEY: misc_feature
<222> LOCATION: (6)..(6)
<223> OTHER INFORMATION: N is A or C

<400> SEQUENCE: 63
tanggntacc ttgttacgac                                                    20

<210> SEQ ID NO 64
<211> LENGTH: 26
<212> TYPE: DNA
<213> ORGANISM: Artificial Sequence
<220> FEATURE:
<223> OTHER INFORMATION: LB-R6 Primer
```

<400> SEQUENCE: 64
gttcgctacc catgctttcg agcctc                                              26

<210> SEQ ID NO 65
<211> LENGTH: 19
<212> TYPE: DNA
<213> ORGANISM: Artificial Sequence
<220> FEATURE:
<223> OTHER INFORMATION: Actino-R3 Primer
<220> FEATURE:
<221> NAME/KEY: misc_feature
<222> LOCATION: (16)..(16)
<223> OTHER INFORMATION: N is A or G

<400> SEQUENCE: 65
accttcctcc gagttnacc                                                      19

<210> SEQ ID NO 66
<211> LENGTH: 21
<212> TYPE: DNA
<213> ORGANISM: Artificial Sequence
<220> FEATURE:
<223> OTHER INFORMATION: Corio-R4H Primer

<400> SEQUENCE: 66
gattactagc aactccgact t                                                   21

<210> SEQ ID NO 67
<211> LENGTH: 25
<212> TYPE: DNA
<213> ORGANISM: Artificial Sequence
<220> FEATURE:
<223> OTHER INFORMATION: Mobil-549R Primer

<400> SEQUENCE: 67
caccgcagac caacagttaa gctgc                                               25

<210> SEQ ID NO 68
<211> LENGTH: 25
<212> TYPE: DNA
<213> ORGANISM: Artificial Sequence
<220> FEATURE:
<223> OTHER INFORMATION: BrdRa Primer
<220> FEATURE:
<221> NAME/KEY: misc_feature
<222> LOCATION: (3)..(3)
<223> OTHER INFORMATION: N is C or T
<220> FEATURE:
<221> NAME/KEY: misc_feature
<222> LOCATION: (4)..(4)
<223> OTHER INFORMATION: N is A or G

<400> SEQUENCE: 68
ccnnggtaag gttcctcgcg tatca                                               25

<210> SEQ ID NO 69
<211> LENGTH: 25
<212> TYPE: DNA
<213> ORGANISM: Artificial Sequence
<220> FEATURE:
<223> OTHER INFORMATION: BrdRb Primer
<220> FEATURE:
<221> NAME/KEY: misc_feature
<222> LOCATION: (3)..(3)
<223> OTHER INFORMATION: N is C or T

<400> SEQUENCE: 69
ccntggtaag gttcctcgcg tatca                                               25

```
<210> SEQ ID NO 70
<211> LENGTH: 19
<212> TYPE: DNA
<213> ORGANISM: Artificial Sequence
<220> FEATURE:
<223> OTHER INFORMATION: Fuso-R6 Primer
<220> FEATURE:
<221> NAME/KEY: misc_feature
<222> LOCATION: (12)..(12)
<223> OTHER INFORMATION: N is C or T

<400> SEQUENCE: 70
cccaggcgga tnacttatc                                                19

<210> SEQ ID NO 71
<211> LENGTH: 20
<212> TYPE: DNA
<213> ORGANISM: Artificial Sequence
<220> FEATURE:
<223> OTHER INFORMATION: Lachno-R3 Primer
<220> FEATURE:
<221> NAME/KEY: misc_feature
<222> LOCATION: (5)..(5)
<223> OTHER INFORMATION: N is A or C

<400> SEQUENCE: 71
cattnttgcg aacgtactcc                                               20

<210> SEQ ID NO 72
<211> LENGTH: 21
<212> TYPE: DNA
<213> ORGANISM: Artificial Sequence
<220> FEATURE:
<223> OTHER INFORMATION: BVAB2/3-R1 Primer
<220> FEATURE:
<221> NAME/KEY: misc_feature
<222> LOCATION: (19)..(19)
<223> OTHER INFORMATION: N is C or G

<400> SEQUENCE: 72
gggtcgatac ctcctacanc t                                             21

<210> SEQ ID NO 73
<211> LENGTH: 21
<212> TYPE: DNA
<213> ORGANISM: Artificial Sequence
<220> FEATURE:
<223> OTHER INFORMATION: Clos-R698 Primer
<220> FEATURE:
<221> NAME/KEY: misc_feature
<222> LOCATION: (6)..(6)
<223> OTHER INFORMATION: N is A or G

<400> SEQUENCE: 73
ggcacntagt tagccggggc t                                             21

<210> SEQ ID NO 74
<211> LENGTH: 20
<212> TYPE: DNA
<213> ORGANISM: Artificial Sequence
<220> FEATURE:
<223> OTHER INFORMATION: ClosXI-XIIR Primer

<400> SEQUENCE: 74
gagtttcaca cttgcgtgcg                                               20
```

```
<210> SEQ ID NO 75
<211> LENGTH: 20
<212> TYPE: DNA
<213> ORGANISM: Artificial Sequence
<220> FEATURE:
<223> OTHER INFORMATION: Clos-XIR Primer

<400> SEQUENCE: 75
gagtttcatg cttgcgcacg                                            20

<210> SEQ ID NO 76
<211> LENGTH: 24
<212> TYPE: DNA
<213> ORGANISM: Artificial Sequence
<220> FEATURE:
<223> OTHER INFORMATION: Peptos-FR Primer
<220> FEATURE:
<221> NAME/KEY: misc_feature
<222> LOCATION: (8)..(8)
<223> OTHER INFORMATION: N is C or T
<220> FEATURE:
<221> NAME/KEY: misc_feature
<222> LOCATION: (19)..(19)
<223> OTHER INFORMATION: N is A or G

<400> SEQUENCE: 76
ggtaaccncc gacacctant actc                                       24

<210> SEQ ID NO 77
<211> LENGTH: 24
<212> TYPE: DNA
<213> ORGANISM: Artificial Sequence
<220> FEATURE:
<223> OTHER INFORMATION: Mega-R870 Primer
<220> FEATURE:
<221> NAME/KEY: misc_feature
<222> LOCATION: (9)..(9)
<223> OTHER INFORMATION: N is A or G

<400> SEQUENCE: 77
ggaattccnc tttcctctcc gata                                       24

<210> SEQ ID NO 78
<211> LENGTH: 20
<212> TYPE: DNA
<213> ORGANISM: Artificial Sequence
<220> FEATURE:
<223> OTHER INFORMATION: Staph-R955 Primer

<400> SEQUENCE: 78
gatccccacg ctttcgcaca                                            20

<210> SEQ ID NO 79
<211> LENGTH: 20
<212> TYPE: DNA
<213> ORGANISM: Artificial Sequence
<220> FEATURE:
<223> OTHER INFORMATION: Strep-R860 Primer
<220> FEATURE:
<221> NAME/KEY: misc_feature
<222> LOCATION: (7)..(7)
<223> OTHER INFORMATION: N is A or G
<220> FEATURE:
<221> NAME/KEY: misc_feature
<222> LOCATION: (9)..(9)
<223> OTHER INFORMATION: N is A or G
<220> FEATURE:
<221> NAME/KEY: misc_feature
<222> LOCATION: (10)..(10)
<223> OTHER INFORMATION: N is C or T
```

<400> SEQUENCE: 79
ggcactnann cccggaaagg                                              20

<210> SEQ ID NO 80
<211> LENGTH: 20
<212> TYPE: DNA
<213> ORGANISM: Artificial Sequence
<220> FEATURE:
<223> OTHER INFORMATION: BProR-1085-2 Primer
<220> FEATURE:
<221> NAME/KEY: misc_feature
<222> LOCATION: (12)..(12)
<223> OTHER INFORMATION: N is A or T
<220> FEATURE:
<221> NAME/KEY: misc_feature
<222> LOCATION: (19)..(19)
<223> OTHER INFORMATION: N is A or C

<400> SEQUENCE: 80
catcgaatta anccacatna                                              20

<210> SEQ ID NO 81
<211> LENGTH: 20
<212> TYPE: DNA
<213> ORGANISM: Artificial Sequence
<220> FEATURE:
<223> OTHER INFORMATION: GPro-R970a Primer
<220> FEATURE:
<221> NAME/KEY: misc_feature
<222> LOCATION: (12)..(12)
<223> OTHER INFORMATION: N is A or G

<400> SEQUENCE: 81
gcgttagctc cngaagccac                                              20

<210> SEQ ID NO 82
<211> LENGTH: 19
<212> TYPE: DNA
<213> ORGANISM: Artificial Sequence
<220> FEATURE:
<223> OTHER INFORMATION: GPro-R970b Primer
<220> FEATURE:
<221> NAME/KEY: misc_feature
<222> LOCATION: (11)..(11)
<223> OTHER INFORMATION: N is A or T

<400> SEQUENCE: 82
cacgttagct ncgggcacc                                               19

<210> SEQ ID NO 83
<211> LENGTH: 19
<212> TYPE: DNA
<213> ORGANISM: Artificial Sequence
<220> FEATURE:
<223> OTHER INFORMATION: GPro-R970c Primer

<400> SEQUENCE: 83
gttagctgcg ccactaaga                                               19

<210> SEQ ID NO 84
<211> LENGTH: 23
<212> TYPE: DNA
<213> ORGANISM: Artificial Sequence
<220> FEATURE:
<223> OTHER INFORMATION: GPro-R970d Primer
<220> FEATURE:
<221> NAME/KEY: misc_feature
<222> LOCATION: (13)..(13)
<223> OTHER INFORMATION: N is C or T

```
<220> FEATURE:
<221> NAME/KEY: misc_feature
<222> LOCATION: (15)..(15)
<223> OTHER INFORMATION: N is A or T

<400> SEQUENCE: 84
ctgcgccact aancncattc ata                                              23

<210> SEQ ID NO 85
<211> LENGTH: 22
<212> TYPE: DNA
<213> ORGANISM: Artificial Sequence
<220> FEATURE:
<223> OTHER INFORMATION: MycoRa Primer
<220> FEATURE:
<221> NAME/KEY: misc_feature
<222> LOCATION: (11)..(11)
<223> OTHER INFORMATION: N is A or G

<400> SEQUENCE: 85
gctccatgtc nccatattgc tt                                               22

<210> SEQ ID NO 86
<211> LENGTH: 22
<212> TYPE: DNA
<213> ORGANISM: Artificial Sequence
<220> FEATURE:
<223> OTHER INFORMATION: MycoRb Primer

<400> SEQUENCE: 86
gcttcatctt acgatttgc ag                                                22

<210> SEQ ID NO 87
<211> LENGTH: 22
<212> TYPE: DNA
<213> ORGANISM: Artificial Sequence
<220> FEATURE:
<223> OTHER INFORMATION: MycoRc Primer

<400> SEQUENCE: 87
gctcactttt acaagttggc ta                                               22

<210> SEQ ID NO 88
<211> LENGTH: 23
<212> TYPE: DNA
<213> ORGANISM: Artificial Sequence
<220> FEATURE:
<223> OTHER INFORMATION: pUC-F Primer

<400> SEQUENCE: 88
cccagtcacg acgttgtaaa acg                                              23

<210> SEQ ID NO 89
<211> LENGTH: 23
<212> TYPE: DNA
<213> ORGANISM: Artificial Sequence
<220> FEATURE:
<223> OTHER INFORMATION: pUC-R Primer

<400> SEQUENCE: 89
agcggataac aatttcacac agg                                              23

<210> SEQ ID NO 90
<211> LENGTH: 24
<212> TYPE: DNA
<213> ORGANISM: Artificial Sequence
```

```
<220> FEATURE:
<223> OTHER INFORMATION: LachnoL3 Primer
<220> FEATURE:
<221> NAME/KEY: misc_feature
<222> LOCATION: (16)..(16)
<223> OTHER INFORMATION: N is A or C

<400> SEQUENCE: 90
gtaaagctct atcagnaggg aaga                                              24

<210> SEQ ID NO 91
<211> LENGTH: 20
<212> TYPE: DNA
<213> ORGANISM: Artificial Sequence
<220> FEATURE:
<223> OTHER INFORMATION: LachnoR1229 Primer
<220> FEATURE:
<221> NAME/KEY: misc_feature
<222> LOCATION: (2)..(2)
<223> OTHER INFORMATION: N is A or C

<400> SEQUENCE: 91
cnctttgttt acgccattgt                                                   20

<210> SEQ ID NO 92
<211> LENGTH: 18
<212> TYPE: DNA
<213> ORGANISM: Artificial Sequence
<220> FEATURE:
<223> OTHER INFORMATION: EntcL Primer

<400> SEQUENCE: 92
ggctcaaccg gggagggt                                                     18

<210> SEQ ID NO 93
<211> LENGTH: 24
<212> TYPE: DNA
<213> ORGANISM: Artificial Sequence
<220> FEATURE:
<223> OTHER INFORMATION: CylL-LF Primer

<400> SEQUENCE: 93
gtgtagttcc tagttttgaa gaac                                              24

<210> SEQ ID NO 94
<211> LENGTH: 19
<212> TYPE: DNA
<213> ORGANISM: Artificial Sequence
<220> FEATURE:
<223> OTHER INFORMATION: Actino16SR Primer

<400> SEQUENCE: 94
tcctccgagt tgaccccgg                                                    19

<210> SEQ ID NO 95
<211> LENGTH: 22
<212> TYPE: DNA
<213> ORGANISM: Artificial Sequence
<220> FEATURE:
<223> OTHER INFORMATION: EntcR Primer
<220> FEATURE:
<221> NAME/KEY: misc_feature
<222> LOCATION: (4)..(4)
<223> OTHER INFORMATION: N is A or G

<400> SEQUENCE: 95
cctncaatcc gaactgagag aa                                                22
```

```
<210> SEQ ID NO 96
<211> LENGTH: 22
<212> TYPE: DNA
<213> ORGANISM: Artificial Sequence
<220> FEATURE:
<223> OTHER INFORMATION: Cy1L-LR Primer

<400> SEQUENCE: 96
gacacaacta cagttactcc ag                                              22
```